US008232440B2

(12) United States Patent
Holtzapple et al.

(10) Patent No.: US 8,232,440 B2
(45) Date of Patent: Jul. 31, 2012

(54) ALTERNATIVE PATHS TO ALCOHOLS AND HYDROCARBONS FROM BIOMASS

(75) Inventors: Mark T. Holtzapple, College Station, TX (US); Cesar B. Granda, College Station, TX (US); Sebastian Taco-Vasquez, Bryan, TX (US); Michael Kyle Ross, Bryan, TX (US); Gary Luce, Spring, TX (US); John A. Spencer, Cypress, TX (US); Rae L. Spencer, Cypress, TX (US)

(73) Assignees: The Texas A&M University System, College Station, TX (US); Terrabon Mix-Alco, LLC, Houston, TX (US)

( * ) Notice: Subject to any disclaimer, the term of this patent is extended or adjusted under 35 U.S.C. 154(b) by 309 days.

(21) Appl. No.: 12/629,285

(22) Filed: Dec. 2, 2009

(65) Prior Publication Data
US 2010/0185021 A1 Jul. 22, 2010

Related U.S. Application Data

(60) Provisional application No. 61/119,250, filed on Dec. 2, 2008.

(51) Int. Cl.
*C01G 3/00* (2006.01)
(52) U.S. Cl. .................................................. 585/240
(58) Field of Classification Search .................. None
See application file for complete search history.

(56) References Cited

U.S. PATENT DOCUMENTS

| | | | |
|---|---|---|---|
| 3,894,107 A | 7/1975 | Butter et al. | |
| 4,128,727 A | 12/1978 | Leupold et al. | |
| 4,293,499 A | 10/1981 | Hughes | |
| 4,421,939 A | 12/1983 | Kiff et al. | |
| 5,693,296 A | 12/1997 | Holtzapple et al. | |
| 5,865,898 A | 2/1999 | Holtzapple et al. | |
| 5,962,307 A | 10/1999 | Holtzapple et al. | |
| 5,973,193 A | 10/1999 | Crane et al. | |
| 5,986,133 A | 11/1999 | Holtzapple et al. | |
| 6,043,392 A | 3/2000 | Holtzapple et al. | |
| 6,262,313 B1 | 7/2001 | Holtzapple et al. | |
| 6,395,926 B1 | 5/2002 | Holtzapple et al. | |
| 6,927,048 B2 | 8/2005 | Verser et al. | |
| 7,251,944 B2 | 8/2007 | Holtzapple et al. | |
| 7,328,591 B2 | 2/2008 | Holtzapple et al. | |
| 7,351,559 B2 | 4/2008 | Verser et al. | |
| 8,153,850 B2 | 4/2012 | Hall et al. | |
| 2003/0077771 A1 | 4/2003 | Verser et al. | |
| 2006/0024801 A1 | 2/2006 | Holtzapple et al. | |
| 2006/0188980 A1 | 8/2006 | Holtzapple et al. | |
| 2007/0014895 A1 | 1/2007 | Holtzapple et al. | |
| 2007/0299291 A1 | 12/2007 | Koivusalmi | |
| 2008/0176301 A1 | 7/2008 | Granda et al. | |
| 2008/0280338 A1 | 11/2008 | Hall et al. | |
| 2009/0114591 A1 | 5/2009 | Holtzapple et al. | |
| 2010/0185021 A1 | 7/2010 | Ross et al. | |

FOREIGN PATENT DOCUMENTS
WO 2008141204 A2 11/2008

OTHER PUBLICATIONS

International Preliminary Report on Patentability for PCT/US2009/066419 dated Jun. 6, 2011 (5 pages).
International Application No. PCT/US2009/066419 International Search Report dated Jul. 19, 2010, 9 pages.
Sen, B. et al. "Metal-Support Effects on Acetone Hydrogenation over Platinum Catalysts", Journal of Catalysis 113, 52-71 (1988).
Aramendia, M. et al. "Catalytic Application of Zeolites in the Methanol Conversion to Hydrocarbons", Chemistry Letters 2002 (2 pgs.).
van Druten et al. "Promotion Effects in the Hydrogenation of Propanal and Acetone Over Palladium", React.Kint.Catal.Lett. vol. 68, No. 1 15-23 (1999).
Yurieva, T.M. "Mechanisms for activation of hydrogen and hydrogenation of acetone to isopropanol and of carbon oxides to methanol over copper-containing oxide catalysts", Catalysis Today 51 (1999) 457-467.
Chang, Nan-Sheng et al., "Kinetic studies of ketone hydrogenation over Raney nickel catalyst", Chemical Engineering Science 55 (2000) 5721-5732.
Comelli, R.A. et al., "Transformation of C1-C4 Alcohols into Hydrocarbons on a Amorphous Silica-Alumina Catalyst", Applied Catalysis, 36, 299-306 (1988).
Minachev, Kh. M. et al., "Hydrogenation of Acetone on Cationic Forms of Zeolites", Russian Chemical Bulletin, vol. 23, 7 (1974) 1472-1475.
Ardah, E. G. R. et al., "Distillation of Acetate of Lime", Industrial and Engineering Chemistry, vol. 16, No. 11 (Nov. 1924) 1133-1139.
Hayashi, H. et al., "Conversion of Methanol into Hydrocarbons over Ammonium 12-Tungstophosphate", Journal of Catalysis, 83, 192-204 (1983).
Setiadi, Suprapto et al., "Conversion of Acetone and Aromatic Chemicals with HZSM-5", Journal of the Japan Institute of Energy, 82, 926-932 (2003).
Hutchings, Graham J. et al., "The Conversion of Methanol and Other O-Compounds to Hydrocarbons over Zeolite", Journal of Catalysis 147, 177-185 (1994).
Takahara, Isco et al., "Dehydration of ethanol into ethylene over solid acid catalysts," Catalysis letters 105(3-4), 249-252 (2005.
Mostafa, M. R. et al., "Conversion of ethanol and isopropanol on alumina, titania and alumina titania catalysts," Material Letters 12, 207-213 (1991).
Le Van Mao, R. et al, "Ethylene from ethanol over zeolite catalysts," Applied Catalysis 34, 163-179 (1987).

*Primary Examiner* — Brian J Davis
(74) *Attorney, Agent, or Firm* — Timothy S. Westby; Porter Hedges LLP

(57) ABSTRACT

A method of producing alcohols, hydrocarbons, or both from biomass by converting biomass into a carboxylic acid, reacting the carboxylic acid with an olefin to produce an ester and hydrogenolyzing the ester to produce alcohol. A method of producing hydrocarbons from biomass by converting at least a portion of the biomass into a carboxylic acid, a ketone, or an ammonium carboxylate salt, reacting at least one of a portion of the carboxylic acid, a portion of the ketone, or a portion of the ammonium carboxylate salt in an oligomerization reactor as at least part of a process that produces an oligomerization product and separating hydrocarbons from the oligomerization product.

32 Claims, 37 Drawing Sheets

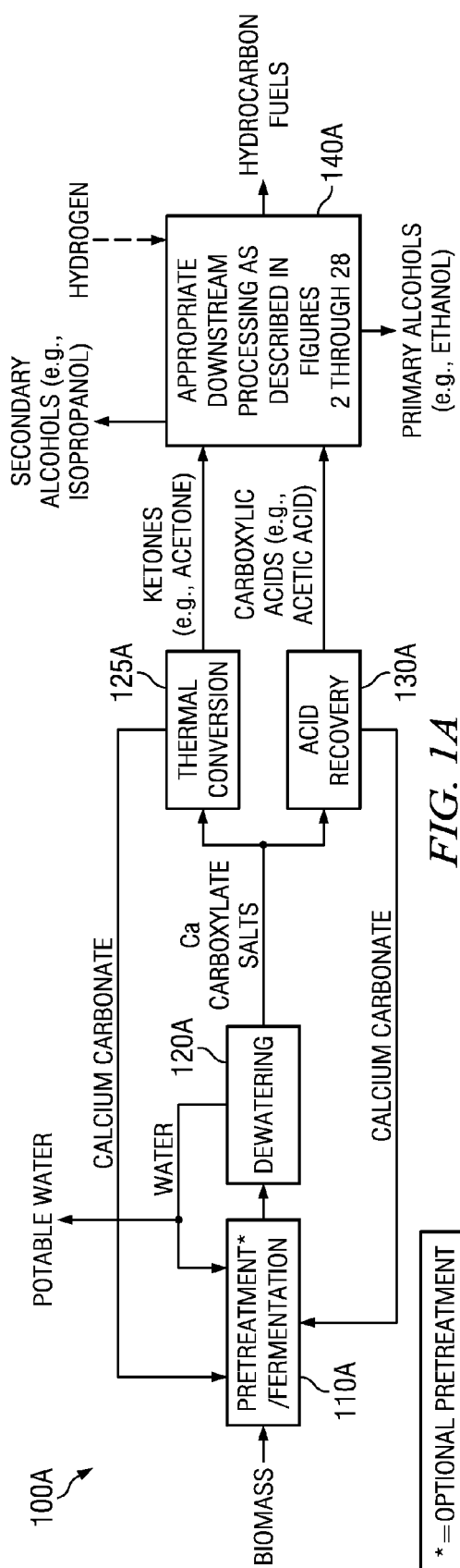
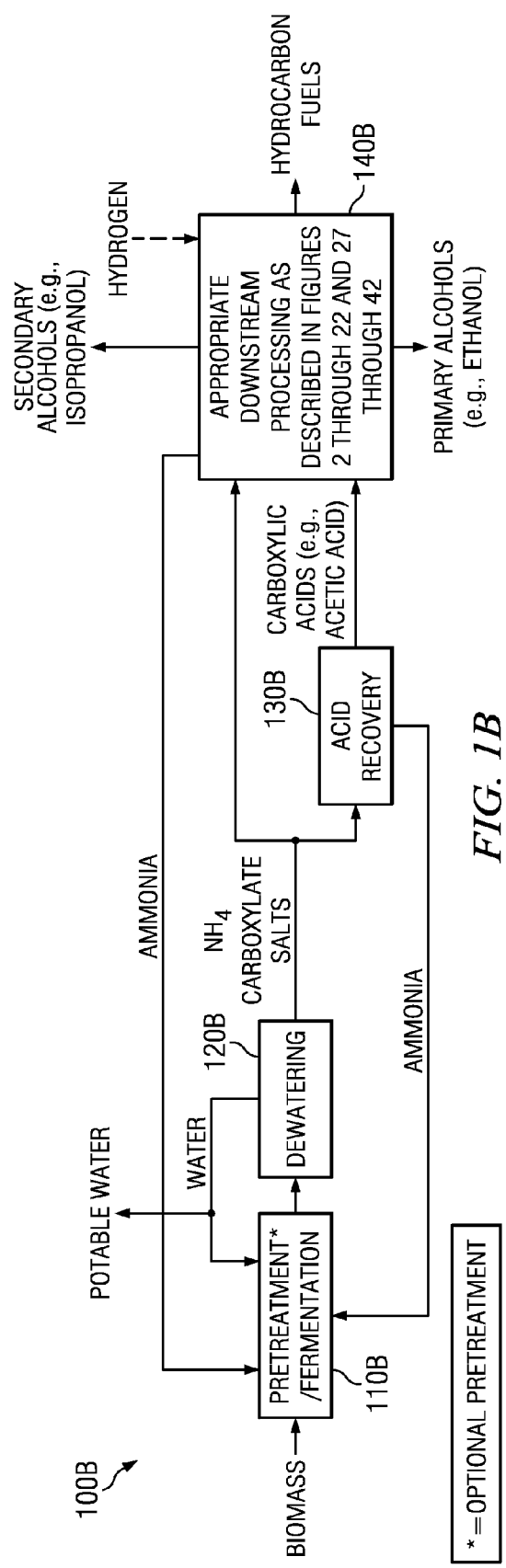
FIG. 1A
FIG. 1B

ALTERNATIVE PATHS TO ALCOHOLS AND HYDROCARBONS FROM BIOMASS

CROSS-REFERENCE TO RELATED APPLICATIONS

Pursuant to 35 U.S.C. §119(e), this application claims priority to U.S. Provisional Patent Application No. 61/119,250 which was filed Dec. 2, 2008 and which is hereby incorporated herein by reference.

STATEMENT REGARDING FEDERALLY SPONSORED RESEARCH OR DEVELOPMENT

Not Applicable.

BACKGROUND

1. Technical Field

This disclosure relates to biomass. More particularly, this disclosure relates to alternative paths to alcohols and hydrocarbons from biomass.

2. Background of the Invention

Biomass is biological material that can be converted into fuel. Biofuels may be produced from most biological, carbon sources. For example, biofuels may be produced from sources such as photosynthetic plants. Biofuels may be used in a wide variety of applications, such as for cooking, heating, and transportation.

There are many technologies that produce biofuels from biomass. For example, ethanol may be produced from lignocellulosic biomass. Enzymatic production of free sugars from biomass has been reported. The sugars are then directly fermented to ethanol. Also in the prior art is gasification of biomass to synthesis gas (CO and $H_2$), which is directly fermented to ethanol, or may be catalytically converted to mixed alcohols. Various technologies enzymatically produce free sugars from biomass, and the sugars are subsequently fermented to acetic acid using homoacetogens. The acetic acid may subsequently be hydrogenated to ethanol using the methods described in U.S. Pat. Nos. 6,927,048 and 7,351,559.

Routes to hydrocarbons include the following: alcohols produced by the above methods can be converted to hydrocarbons using a zeolite catalyst; synthesis gas produced by gasifying biomass can be converted to hydrocarbons by using a Fisher-Tropsch catalyst; sugars may be catalytically converted to hydrocarbons; and biomass may be converted to hydrocarbons by pyrolysis.

Although various technologies exist for producing biofuels from biomass, there is a need in the art for new, improved more efficient systems and processes for the production of alcohols and/or hydrocarbons from biomass.

SUMMARY

Herein disclosed is a method of producing alcohols, hydrocarbons, or both from biomass by converting biomass into a carboxylic acid, reacting the carboxylic acid with an olefin to produce an ester, and hydrogenolyzing the ester to produce alcohol. In embodiments, reacting the carboxylic acid with an olefin to produce an ester and hydrogenolyzing the ester to produce an alcohol are carried out in the same reactor. In embodiments, reacting the carboxylic acid with an olefin to produce an ester and hydrogenolyzing the ester to produce an alcohol are carried out with one catalyst. In embodiments, the method further comprises dehydrating at least a portion of the alcohol to produce an olefin feed, at least a portion of the olefin feed providing the olefin that reacts with the carboxylic acid to produce the ester. In embodiments, reacting the carboxylic acid with an olefin to produce an ester and hydrogenolyzing the ester to produce an alcohol are carried out in the same reactor. In embodiments, reacting the carboxylic acid with an olefin to produce an ester and hydrogenolyzing the ester to produce an alcohol are carried out with one catalyst. The method may further comprise oligomerizing at least another portion of the alcohol to produce hydrocarbons. The method may further comprise oligomerizing at least another portion of the olefin feed to produce hydrocarbons.

In embodiments, the method further comprises oligomerizing at least a portion of the alcohol to produce an olefin feed, at least a portion of the olefin feed providing the olefin that reacts with the carboxylic acid to produce the ester. The method may further comprise oligomerizing at least a portion of the alcohol to produce hydrocarbons. In embodiments, reacting the carboxylic acid with an olefin to produce an ester and hydrogenolyzing the ester to produce an alcohol are carried out in the same reactor. In embodiments, reacting the carboxylic acid with an olefin to produce an ester and hydrogenolyzing the ester to produce an alcohol are carried out with one catalyst. Such method may further comprise oligomerizing at least another portion of the alcohol to produce an olefin feed, at least a portion of the olefin feed providing the olefin that reacts with the carboxylic acid to produce the ester.

In embodiments, converting the biomass into a carboxylic acid further comprises fermenting the biomass to yield a liquid fermentation broth comprising water and carboxylate salts, dewatering the liquid fermentation broth to separate the water from the carboxylate salts, and converting the carboxylate salts into carboxylic acids.

In embodiments, the method further comprises converting the alcohol into a hydrocarbon. In such embodiments, reacting the carboxylic acid with an olefin to produce an ester and hydrogenolyzing the ester to produce an alcohol may be carried out in the same reactor. In such embodiments, reacting the carboxylic acid with an olefin to produce an ester and hydrogenolyzing the ester to produce an alcohol may be carried out with one catalyst. Converting the alcohol into a hydrocarbon can comprise an oligomerization process. In embodiments, converting the alcohol into a hydrocarbon comprises oligomerizing at least a portion of the alcohol to produce the hydrocarbon. In embodiments, converting the alcohol into a hydrocarbon comprises dehydrating at least a portion of the alcohol to produce an olefin feed, and oligomerizing at least a portion of the olefin feed to produce the hydrocarbon.

Also disclosed is a method of producing hydrocarbons from biomass by converting at least a portion of the biomass into a carboxylic acid, a ketone, or an ammonium carboxylate salt, reacting at least one of a portion of the carboxylic acid, a portion of the ketone, or a portion of the ammonium carboxylate salt in an oligomerization reactor as at least part of a process that produces an oligomerization product, and separating hydrocarbons from the oligomerization product. In embodiments, the method further comprises converting another portion of the carboxylic acid, another portion of the ketone, or another portion of the ammonium carboxylate salt to alcohol, and providing at least a portion of the alcohol to the oligomerization reactor for the process that produces the oligomerization product. Converting the another portion of the carboxylic acid into alcohol may comprise reacting the another portion of the carboxylic acid with an olefin to produce an ester; and hydrogenolyzing the ester to produce the alcohol. Reacting at least one of the portion of the carboxylic acid, the portion of the ketone, or the portion of the ammonium carboxylate salt in the oligomerization reactor as at least part of the process that produces the oligomerization product and converting the another portion of the carboxylic acid, the another portion of the ketone, or the another portion of the ammonium carboxylate salt to alcohol can be carried out in the oligomerization reactor. Reacting at least one of the portion of the carboxylic acid, the portion of the ketone, or the portion of the ammonium carboxylate salt in the oligomerization reactor as at least part of the process that produces the oligomerization product and converting the another portion of the carboxylic acid, the another portion of the ketone, or the another portion of the ammonium carboxylate salt to alcohol may be carried out with one catalyst.

The method may further comprise separating a recycle stream from the oligomerization product, processing the recycle stream in a reformer to produce hydrogen, and providing a least a portion of the produced hydrogen for the process of converting the another portion of the carboxylic acid, the another portion of the ketone, or the another portion of the ammonium carboxylate salt to alcohol. In embodiments wherein at least a portion of the biomass is converted to the ammonium carboxylate salt, the method may further comprise separating ammonia from the recycle stream prior to processing the recycle stream in a reformer to produce hydrogen. In embodiments, the method further comprises separating olefins from the recycle stream prior to processing the recycle stream in a reformer to produce hydrogen, and providing the olefins to the oligomerization reactor for the process that produces the oligomerization product. In embodiments, at least a portion of the biomass is converted to an ammonium carboxylate salt, and the method further comprises separating ammonia from the recycle stream prior to processing the recycle stream in a reformer to produce hydrogen.

In embodiments, the method further comprises separating a recycle stream from the oligomerization product, separating olefins from the recycle stream, and providing the olefins to the oligomerization reactor for the process that produces the oligomerization product.

In embodiments, at least a portion of the biomass is converted into a carboxylic acid. Converting at least a portion of the biomass into a carboxylic acid may comprise fermenting the biomass to produce a calcium carboxylate salt or an ammonium carboxylate salt, and converting the calcium carboxylate salt or the ammonium carboxylate salt to carboxylic acid using an acid recovery process.

In embodiments, at least a portion of the biomass is converted into a ketone. Converting at least a portion of the biomass into a ketone may comprise fermenting the biomass to produce a calcium carboxylate salt, and thermally converting the calcium carboxylate salt into the ketone. In embodiments, converting at least a portion of the biomass into a ketone comprises fermenting the biomass to produce a calcium carboxylate salt or an ammonium carboxylate salt, converting the calcium carboxylate salt or the ammonium carboxylate salt to carboxylic acid using an acid recovery process, and catalytically converting carboxylic acid into ketone. In embodiments, the method further comprises converting another portion of the ketone into alcohol by hydrogenating the another portion of the ketone.

In embodiments, converting at least a portion of the biomass into a ketone comprises fermenting the biomass to produce a calcium carboxylate salt, and producing hot ketone vapors and calcium carbonate in a ketone reactor operated with a sweep gas. The sweep gas can be reactive, condensable or both. In embodiments, the sweep gas comprises hydrogen. In embodiments, the sweep gas comprises steam.

In embodiments, at least a portion of the biomass is converted into the ammonium carboxylate salt. Such a method may further comprise converting another portion of the ammonium carboxylate salt to alcohol, and providing the alcohol to the oligomerization reactor for the process that produces the oligomerization product, wherein converting the another portion of the ammonium carboxylate salt into alcohol comprises converting the another portion of the ammonium carboxylate salt into a second carboxylic acid, reacting the second carboxylic acid with an olefin to produce an ester, and hydrogenolyzing the ester to produce the alcohol. In embodiments wherein at least a portion of the biomass is converted into the ammonium carboxylate salt, the method may further comprise separating ammonia from the ammonium carboxylate salt prior to reacting the portion of the ammonium carboxylate salt in the oligomerization reactor as at least part of the process that produces the oligomerization product.

In embodiments, converting at least a portion of the biomass into a carboxylic acid, a ketone, or an ammonium carboxylate salt comprises a fermentation process in a fermenter, and the method further comprises separating a gaseous recycle stream from the oligomerization product and providing at least a portion of the gaseous recycle stream to the fermenter. The method may further comprise converting another portion of the carboxylic acid, another portion of the ketone, or another portion of the ammonium carboxylate salt to alcohol, and providing the alcohol to the oligomerization reactor. In some such embodiments, at least a portion of the biomass is converted into a carboxylic acid. In some such embodiments, at least a portion of the biomass is converted into a ketone. In some such embodiments, at least a portion of the biomass is converted into an ammonium carboxylate salt. Such a method may further comprise separating ammonia from the gaseous recycle stream prior to providing the at least a portion of the gaseous recycle stream to the fermenter.

In embodiments, reacting at least one of the portion of the carboxylic acid, the portion of the ketone, or the portion of the ammonium carboxylate salt in the oligomerization reactor as at least part of the process that produces the oligomerization product and converting the another portion of the carboxylic acid, the another portion of the ketone, or the another portion of the ammonium carboxylate salt to alcohol are carried out in the oligomerization reactor. Reacting at least one of the portion of the carboxylic acid, the portion of the ketone, or the portion of the ammonium carboxylate salt in the oligomerization reactor as at least part of the process that produces the oligomerization product and converting the another portion of the carboxylic acid, the another portion of the ketone, or the another portion of the ammonium carboxylate salt to alcohol can be carried out with one catalyst.

In embodiments, the method further comprises separating fermenter gases exiting the fermenter, processing the fermenter gases in a reformer to produce hydrogen, and providing a least a portion of the produced hydrogen for the process of converting the another portion of the carboxylic acid, the another portion of the ketone, or the another portion of the ammonium carboxylate salt to alcohol.

Although specific advantages are enumerated herein, various embodiments may include all, some, or none of the enumerated advantages. Additionally, other technical advantages may become readily apparent to one of ordinary skill in the art after review of the following figures and description.

BRIEF DESCRIPTION OF THE DRAWINGS

For a more complete understanding of example embodiments of the present invention and its advantages, reference is now made to the following description, taken in conjunction with the accompanying drawings, in which:

FIGS. 1A and 1B are block diagrams of calcium and ammonia-based biomass conversion systems respectively, according to embodiments;

DETAILED DESCRIPTION

Figure 2:
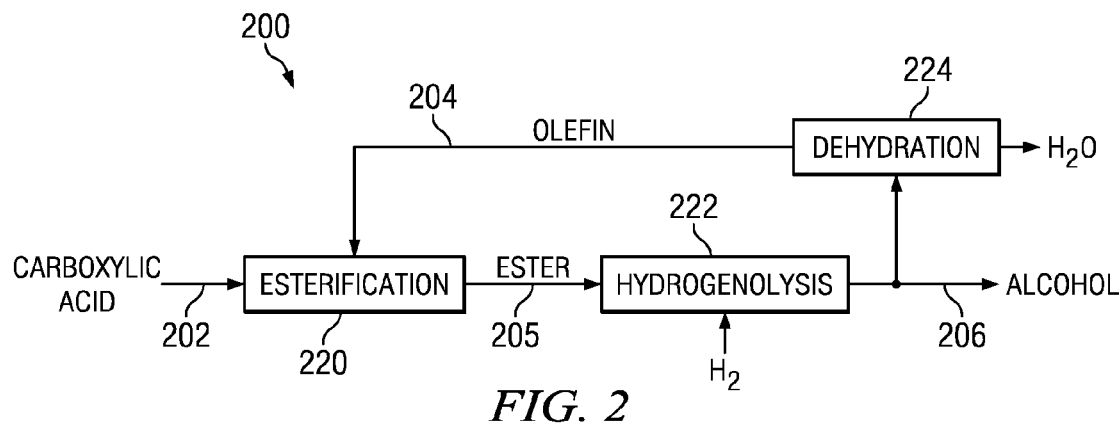
FIG. 2 is a block diagram showing conversion of carboxylic acids to alcohols, according to an embodiment.

Herein disclosed are systems and methods of producing alcohols and/or hydrocarbons from biomass. In accordance with an embodiment of this disclosure, a method of producing alcohols or hydrocarbons from biomass includes converting biomass into a carboxylic acid. The carboxylic acid is reacted with an olefin to produce an ester. The ester is hydrogenolyzed to produce alcohol. The alcohol can then be oligomerized to produce hydrocarbons.

Certain embodiments of this disclosure may provide technical advantages. For example, a technical advantage of one embodiment may include the capability to convert biomass-derived compounds (i.e., carboxylate salts, carboxylic acids, or ketones) to fuels (alcohols, hydrocarbons). Other technical advantages of other embodiments may include a route to ethanol from biomass, prior to hydrogenolysis, reacting carboxylic acids with an olefin rather than with an alcohol (as is more commonly done), thereby avoiding or minimizing the formation of water in the reaction. Yet other technical advantages of other embodiments may include a route to ethanol from biomass, reacting carboxylic acids with an olefin in the presence of hydrogen in the same reactor and with the same catalyst, thus producing alcohols in one step rather than two and avoiding or minimizing the formation of water in the reaction. Yet other technical advantages of other embodiments may include adding hydrogen to the reaction of ketones or carboxylic acids for producing hydrocarbons. Yet other technical advantages of other embodiments may include a direct conversion into hydrocarbons of ammonium carboxylate salts, which have been generated by fermentation of biomass, with and without the addition of hydrogen.

It should be understood at the outset that, although example implementations of embodiments are illustrated below, the systems and methods of this disclosure may be implemented using any number of techniques, whether currently known or not. The present invention should in no way be limited to the example implementations, drawings, and techniques illustrated below. Additionally, the drawings are not necessarily drawn to scale and may not illustrate obvious pieces of equipment such as valves and instrumentation.

Routes to alcohols and hydrocarbons, according to teachings of certain embodiments will be described below. Examples of catalysts and operating conditions that may be utilized in various embodiments are presented in Tables I-V below.

TABLE I

Esterification of Carboxylic Acids and Olefin

| Catalyst | Temperature (° C.) | Pressure (kPa) | Reference |
|---|---|---|---|
| solid acid catalysts (MCM-22, MCM-49, MCM-56, ZSM-5, zeolite-Beta) | 50 to 300 200 to 250 (preferable) | 450 to 21,000 2200 to 11,000 (preferable) | U.S. Pat. No. 5,973,193 |

TABLE II

Hydrogenolysis of Ester

| Catalyst | Temperature (° C.) | Pressure (kPa) | Reference |
|---|---|---|---|
| Copper chromite | >200 | >4,100 | widely used in industry (e.g., for making detergent alcohols from fatty acids) |
| Reduced CuO—ZnO catalyst | ~150 | <2,400 | World Patent WO 82/03854 |

TABLE III

Dehydration of Alcohol to Olefin

| Catalyst | Temperature (° C.) | Pressure (kPa) | Reference |
|---|---|---|---|
| ZSM-5 zeolite | 20-760 | | U.S. Pat. No. 4,011,278 |
| Molecular sieve catalyst composition comprises a molecular sieve selected from the group consisting of: SAPO-5, SAPO-8, SAPO-11, SAPO-16, SAPO-17, SAPO-18, SAPO-20, SAPO-31, SAPO-34, SAPO-35, SAPO-36, SAPO-37, SAPO-40, SAPO-41, SAPO-42, SAPO-44, SAPO-47, SAPO-56, AEI/CHA intergrowths, metal containing forms thereof, intergrown forms thereof, and mixtures thereof | 200-1000 350-550 (preferable) | 0.1 to 5,000 20 to 500 (preferable) | USPTO Patent Application 20060149109 |
| Solid acid catalysts (e.g., zeolites, silica-alumina) | 180-300 | ~100 | a. |
| γ-$Al_2O_3$ catalyst | 410-440 | | b. |
| HZSM-5 zeolite modified with Fe, Mn and Co | Various temperatures (optimal 220° C.) | | c. |
| Alumina, titania, and alumina-titania hydrogels catalysts | <400 | | d. |
| High-silica zeolite, high-silica zeolite with Fe | <400 | | e. |
| ZSM-5 zeolite modified with Zn and Mn | 400 | | f. |
| Clinoptilolite zeolite modified by contact with NaOH and HCl | 350 | | South African Patent ZA 8907621 |
| HZSM-5 zeolite modified by Mg, Ca, Ba and Sr. | <300 | | g. | a. Isao Takahara, Masahiro Saito, Megumu Inaba, Kazuhisa Murata, "Dehydration of ethanol into ethylene over solid acid catalysts," Catalysis letters 105(3-4), 249-252 (2005).
b. Li, Ying; Chen, Xiao Chun; Sun, Wei; Liu, Shi Wei; Hou, Wei, "Experimental study of the catalytic dehydration of ethanol to ethylene on a γ-$Al_2O_3$ catalyst," Ziran Kexueban 34(5), 449-452 (2007).
c. Hu, Yaochi; Huang, He; Shi, Haifeng; Hu, Yi; Yan, Jie; Chen, Li, "Catalytic dehydration of ethanol to ethylene using transition metal modified HZSM-5," Huaxue Yu Shengwu Gongcheng 24(2), 19-21 (2007).
d. Mostafa, M. R., Youssef, A. M., Hassan, S. M., "Conversion of ethanol and isopropanol on alumina, titania and alumina titania catalysts," Material Letters 12, 207-213 (1991).
e. Cursetji, R. M.; Singh, A. N.; Deo, A. V., "Ethylene from ethyl alcohol on high silica zeolite catalyst," Chemical Age of India 37(6), 407-410 (1986).
f. Le Van Mao, R., Levesque, P., McLaughlin, G., Dao, L. H., "Ethylene from ethanol over zeolite catalysts," Applied Catalysis 34, 163-179 (1987).
g. Huang, X, Hu, Y., Li, H., Huang, H., Hu, Y., "Study on dehydration of ethanol to ethylene catalyzed by alkaline-earth metal modified HZSM-5," Huaxue Shiji 29(12), 705-707 (2007).

TABLE IV

Oligomerization of Alcohols, Carboxylic Acids, or Ketones to Hydrocarbons

| Catalyst | Temperature (° C.) | Pressure (kPa) | Reference |
|---|---|---|---|
| H-ZSM-5 (Si/Al ratio >12) | 260-540 | Atmospheric to 20,700 | U.S. Pat. No. 3,894,106 |
| ZSM-5, ZSM-11, ZSM-12, ZSM-21, TEA Mordenite (Si/Al ratio >12) H form | 260-540 | | U.S. Pat. No. 3,894,107 |
| Alumina, silica-alumina, acid activated clay, sodium-poisoned H-ZSM-5 zeolite, H-ZSM-5 zeolite (Si/Al >30) | 380-540 | | U.S. Pat. No. 3,928,483 |
| ZSM-5, ZSM-11, ZSM-12, ZSM-23, ZSM-35, ZSM-38, ZSM-48 (Si/Al ratio >12), H form | 290-540 | | U.S. Pat. No. 4,359,595 |
| Ruthenium supported in catalytically active amount composited with titania or titania-containing support | 150-350 | 1,100-5,520 | U.S. Pat. No. 4,513,161 |
| Silica-alumina, Y zeolite, mordenite, binary oxides, beta zeolites, zeolite L, MAZ, alumina-expanded bentonite clay, USY, REY, ZSM-5, FER, GME, MTW, erionite and crystalline silicon-aluminum phosphate molecular sieves, crystalline borosilicates | 300-500 | Atmospheric to 3,500 | U.S. Pat. No. 5,191,142 |

TABLE IV-continued

Oligomerization of Alcohols, Carboxylic Acids, or Ketones to Hydrocarbons

| Catalyst | Temperature (° C.) | Pressure (kPa) | Reference |
|---|---|---|---|
| Beta zeolite (Si/Al ratio 12.5, 37.5, 75), mordenite (MOR) (Si/Al ratio 45), ultra stable Y (USY) zeolite (Si/Al ratio 30), ferrierite (Si/Al ratio 27.5), faujasite | 200-500 | | a. |
| H-ZSM-5 zeolite | | | b. |
| Beta, H-ZSM-5, Y zeolites | 300-400 | | c. |
| H-ZSM-5 (Si/Al ratio 25) zeolites | 300-500 | 130 | d. |
| Heteropolyacid compounds of molybdenum and tungsten and ammonium 12-tungstophosphate | 300-400 | | e. |
| Amorphous silica-alumina (Si/Al ratio 11.3) | 310-450 | Atmospheric | f. |
| ZSM-5 zeolite | | | g. |
| Triflic acid (TFA or trifluoromethane sulfonic acid) bearing ZSM-5 zeolite | 200-210 | | h. | a. Aramendía, M. A., Borau, V., Jiménez, C., Marinas, J. M., Roldán, R., "Catalytic application of zeolites in methanol conversion to hydrocarbons," Chemistry Letters 31(7), 672-673 (2002).
b. Udrea, I., Udrea, M., Frunza, L., Angelescu, E., Onu, P., Ginju, D., "Conversion of C1-C4 alcohols to hydrocarbons over ZSM-5 type zeolites," Heterogeneous Catalysis $6^{th}$ (Pt.2) (1987).
c. Hutchins, G. J., Johnston, P., Lee, D. F., Warwick, A., Williams, C. D., Wilkinson, M., "The conversion of methanol and other O-compounds to hydrocarbons over zeolite β," Journal of catalysis 147, 117-185 (1994).
d. Setiadi, S., Kojima, T., Tsutsui, T, "Conversion of acetone to aromatic chemicals with HZSM-5," Journal of the Japan Institute of Energy 82(12), 926-932 (2003).
e. Hayashi, H., Moffat, J. B., "Conversion of methanol into hydrocarbons over ammonium 12-tungstophosphate," Journal of Catalysis 83, 192-204 (1983).
f. Comelli, R. A., Figoli, N. S., "Transformation of C1-C4 alcohols into hydrocarbons on an amorphous silica-alumina catalyst," Applied Catalysis 36, 299-306 (1988).
g. Costa, E.; Aguado, J.; Ovejero, G.; Canizares, P., "Synthesis of hydrocarbons starting from fermentation products," Revista de la Real Academia de Ciencias Exactas, Fisicas y Naturales de Madrid 79(3), 453-456 (1985).
h. Le Van Mao, R., Huang, L., "The bioacids/bioacetone-to-hydrocarbons (BATH) process," Chemical Industries 46 (novel prod. methods ethylene), 425-442 (1992).

TABLE V

Hydrogenation of Ketones

| Catalyst | Temperature (° C.) | Pressure (kPa) | Reference |
|---|---|---|---|
| Raney nickel | ~130 | ~1,500 | a. |
| Zeolites A, X, Y and mordenite (MOR) in forms of Na, Ca, NH$_4$, Ce and rare-earth elements (REE) | 200-450 | 3,040 | b. |
| Platinum catalysts (Pt/TiO$_2$, Pt/η-Al$_2$O$_3$, Pt/SiO$_2$, Pt powder, and Pt/Au) | 30-90, >90 | 100 | c. |
| Palladium | 100-250 | atmospheric | c., d. |
| Copper Chromite | 20-300 | | e. |
| Copper oxide-chromium oxide catalyst | 60-200 | 200-1100 | Japan Patent JP 03041038 |
| Supported ruthenium catalyst (support: silica, alumina, carbon, kieselguhr, and calcium carbonate) | 75-180 | 350-6900 | U.S. Pat. No. 5,495,055 | a. Chang, N., Aldrett, S., Holtzapple, M. T., Davison, R. R., "Kinetic studies of ketone hydrogenation over Raney nickel catalyst," Chemical Engineering Science 55(23), 5721-5732 (2000).
b. Minachev, Kh. M., Garanin, V. I., Kharlamov, V. V., Kapustin, M. A., "Hydrogenation of acetone on cationic forms of zeolites," Russian Chemical Bulletin 23(7), 1472-1475 (1974).
c. Sen, B., Vannice, M. A., "Metal-support on acetone hydrogenation over platinum catalysts," Journal of Catalysis 113, 52-71 (1988).
d. van Druten, G. M. R., Ponec, V, "Promotion effects in the hydrogenation of propanal and acetone over palladium," React. Kinet. Catal. Lett. 68(1), 15-23 (1999).
e. Yurieva, T. M., "Mechanisms for activation of hydrogen and hydrogenation of acetone to isopropanol and of carbon oxides to methanol over copper-containing oxide catalysts," Catalysis Today 51, 457-467 (1999).

When referring to particular product streams herein, it should be understood that, although the primary product and products are described, other products may exist in the product stream. As one non-limiting example, described in more detail below, a stream of water may contain alcohol.

FIGS. 1A and 1B show block diagrams of embodiments of complete biomass conversion with two options depending of what buffering system is chosen for the fermentation. FIG. 1A shows a calcium-based system 100A, and FIG. 1B shows an ammonia-based system 100B.

According to FIGS. 1A and 1B, pretreatment and fermentation of biomass occurs at Step 110A/110B. Pretreatment is optional depending on whether the biomass is sufficiently digestible "as is." Pretreatment may be performed as known in the art, for example, by using lime pretreatment as described in, but not limited to, U.S. Pat. Nos. 5,693,296 and 5,865,898, and U.S. Patent App. Nos. 60/423,288 and 60/985,059. The digestible biomass may then be directly fermented to carboxylate salts. Such fermentation to carboxylate salts may be performed, for example, as described in, but not limited to, U.S. Pat. No. 5,962,307 and U.S. patent application Ser. Nos. 11/298,983 and 11/456,653. Depending on the buffering system utilized, the carboxylate salts produced in embodiments are calcium or ammonium salts. From the fermentation, a liquid fermentation broth may be obtained, which is mostly water and carboxylate salts. For further treatment, the carboxylate salts may be dewatered at Step 120A/120B. Dewatering may be performed, for example, using processes or systems described in, but not limited to, U.S. Pat. Nos. 5,986,133, 7,251,944, and 7,328,591, and U.S. Pat. App. No. 60/985,059. Teachings of certain embodiments recognize that dewatering may produce concentrated carboxylate salts. In some embodiments, the water produced by step 120A/120B may be used as an input at step 110A/110B.

In calcium-based system 100A, the calcium carboxylate salts may undergo thermal conversion into ketones at step 125A. Systems and processes for effecting such thermal conversion into ketones are described, for example, in U.S. Pat. Nos. 6,043,392 and 6,262,313. In addition, carboxylic acids may be recovered from the salts at step 130A. Recovery of carboxylic acids may be effected via "acid springing," for example, as described in, but not limited to, U.S. Pat. No. 6,395,926. The resulting carboxylic acids or ketones may then be sent downstream to be processed at step 140A, as described in FIGS. 2-24, 27 and 28. Alternatively or additionally, the formation of ketones using, for example, thermal conversion as described in FIGS. 1A and 25 (Step 125A) may be integrated with the appropriate downstream processing as described in FIGS. 18-24, using a sweep gas as described in FIG. 26. Ketones/ketone vapors may also be generated by passing carboxylic acids through a catalytic bed of, for example, zirconium oxide.

In the ammonia-based system 100B, the carboxylic acids may be recovered from the ammonium carboxylate salts at step 130B. Recovery of carboxylic acids may be effected via "acid springing," for example, as described in, but not limited to, U.S. patent application Ser. No. 11/456,653. The resulting carboxylic acids may be sent downstream to be processed at step 140B, as described in FIGS. 2-22, 27 and 28. Alternatively or additionally, the ammonium carboxylate salts may be sent directly downstream to be processed as described in FIGS. 29-42.

In both the calcium-based system 100A and the ammonia-based system 100B, hydrogen may be added to step 140A/140B as needed. The hydrogen may be generated off-site and delivered (e.g., via pipeline or other suitable device), or it may be generated on site from gasification of the undigested fermentation residue, from steam reforming of natural gas, from the waste hydrocarbon gases generated in the conversion, or from other suitable methods. In addition, some hydrogen is produced in the fermentation step 110A/110B that may be recovered in a manner similar as described in, but not limited to, U.S. patent application Ser. No. 11/948,506. Teachings of certain embodiments recognize that highly-pure hydrogen may not be required.

FIG. 2 shows a block diagram of a system 200 for converting carboxylic acids to alcohols, according to an embodiment. Carboxylic acids 202 are esterified by reacting with olefins 204 in an esterification reactor 220. The resulting esters 205 are hydrogenolyzed to alcohols 206 in a separate hydrogenolysis reactor 222. A portion of alcohol product 206 may be dehydrated to form olefins 204 in a dehydration reactor 224; the remaining alcohol 206 may be harvested as product. If desired, the alcohol products 206 exiting the hydrogenolysis reactor 222 can be separated by distillation. The higher alcohols can be dehydrated to form higher olefins (propylene and above). Teachings of certain embodiments recognize that using olefins instead of primary alcohols may enable the esterification reactor 220 to produce ester without producing water.

Figure 3:
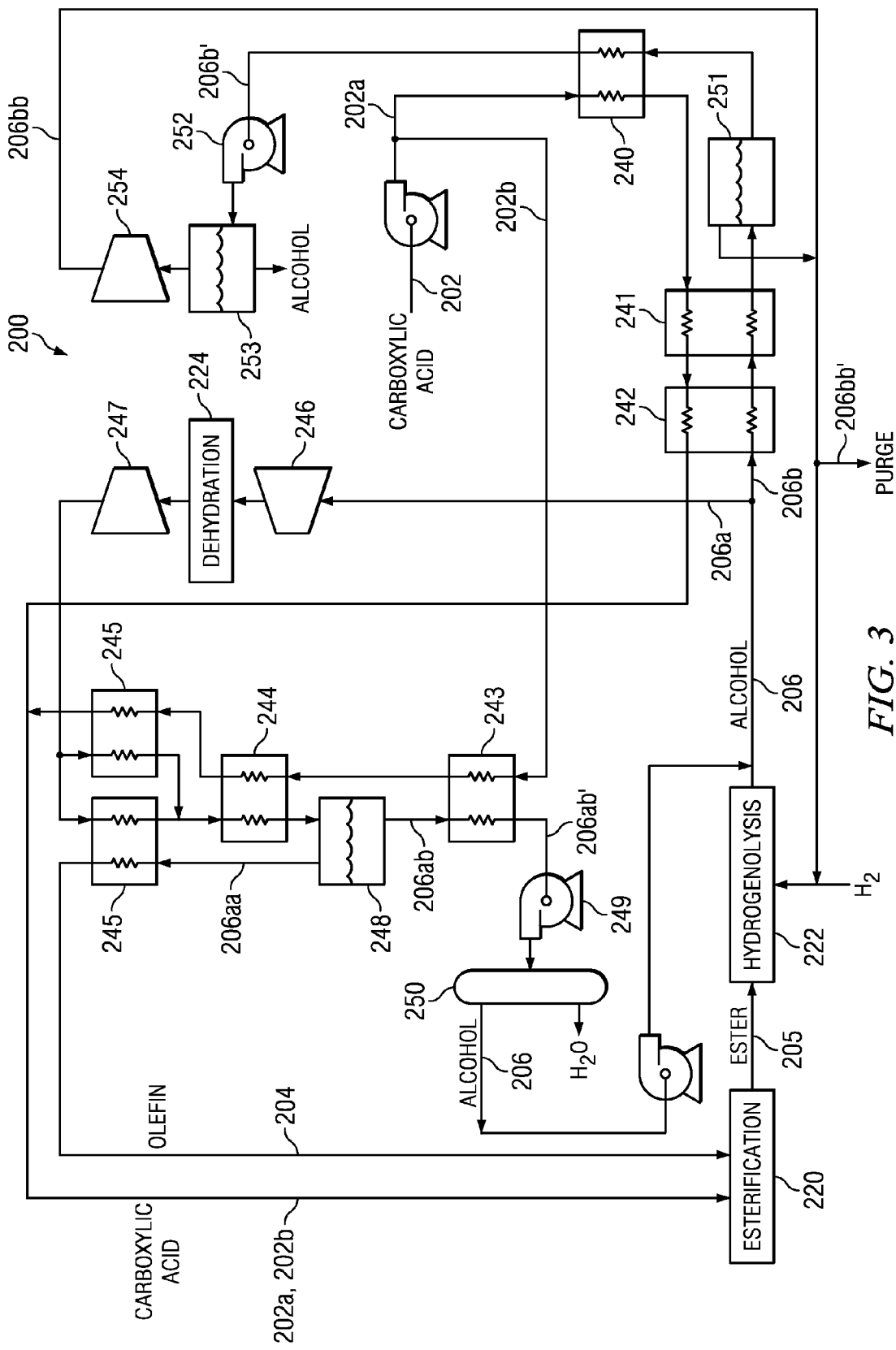
FIG. 3 is a block diagram showing details of a conversion of carboxylic acids to alcohols, according to an embodiment.

FIG. 3 shows a detailed description of system 200 for converting carboxylic acids to alcohols, according to an embodiment. In this embodiment, the carboxylic acid stream 202 is split into two portions 202a and 202b. Stream 202a is sent to sensible heat exchanger 240, latent heat exchanger 241, and sensible heat exchanger 242, such that the stream 202a becomes superheated vapor. Stream 202b is sent to sensible heat exchanger 243, latent heat exchanger 244, and sensible heat exchanger 245, such that the stream 202b becomes superheated vapor. The superheated carboxylic acid vapor streams 202a and 202b react with olefins 204 in esterification reactor 220 to form esters 205. In some embodiments, esterification reactor 220 has its own temperature control system. Esters 205 react with hydrogen in a hydrogenolysis reactor 222 to produce alcohols 206. In some embodiments, hydrogenolysis reactor 222 has its own temperature control system.

Alcohol product stream 206 is split into two streams 206a and 206b. Stream 206a enters expander 246, where the pressure is reduced. The low-pressure alcohol enters dehydration reactor 224. Teachings of certain embodiments recognize that lowering the pressure in expander 246 may improve dehydration performance because dehydration tends to occur at lower pressure. In some embodiments, dehydration reactor 224 has its own temperature control system. Stream 206a (comprising olefins 206aa and water 206ab) exiting dehydration reactor 224 may then be compressed in compressor 247 and enter sensible heat exchanger 245 and latent heat exchanger 244, which cools the stream and allows water 206ab to condense. Olefin 206aa and water 206ab may then be separated in tank 248. Olefin 206aa is heated in sensible heat exchanger 245 so it can enter esterification reactor 220 as all or part of the olefin 204. The water 206ab exiting tank 248 is cooled in sensible heat exchanger 243. In some embodiments, water 206ab may flow through a turbine 249 as part of a high-pressure liquid 206ab' to recover expansion energy. The liquid 206ab' has primarily water, but it may also have some alcohols because the dehydration reaction in dehydration reactor 224 is reversible. The alcohols in liquid 206ab' are recovered by distillation in column 250 and returned to the alcohol stream 206.

Stream 206b, which represents the portion of the alcohol that is recovered as product, is cooled through sensible heat exchanger 242, latent heat exchanger 241, and sensible heat exchanger 240. The gas space in tank 251 may contain hydrogen, which may be then recycled to hydrogenolysis reactor 222. In some embodiments, the stream 206b may flow through a turbine 252 as part of a high-pressure liquid 206b' to recover expansion energy. The gas space in tank 253 may contain hydrogen, which is compressed using compressor 254. A portion thereof may be returned via line 206bb to hydrogenolysis reactor 222.

Recycle stream 206bb may contain non-hydrogen gases, which may be purged via line 206bb' in certain embodiments to prevent accumulation within the system. The purged gases in line 206bb' may be sent to a separator to recover the hydrogen, or they may be burned for process heat. Esterification reactor 220 and/or hydrogenolysis reactor 222 can operate at a higher pressure (~2000 to 4000 kPa), whereas dehydration reactor 224 operates at a lower pressure (~20 to 500 kPa), according to certain embodiments. In the illustrated embodiment, expander 246 recovers energy from the pressure reduction and allows it to supplement the energy used by compressor 247.

Figure 4:
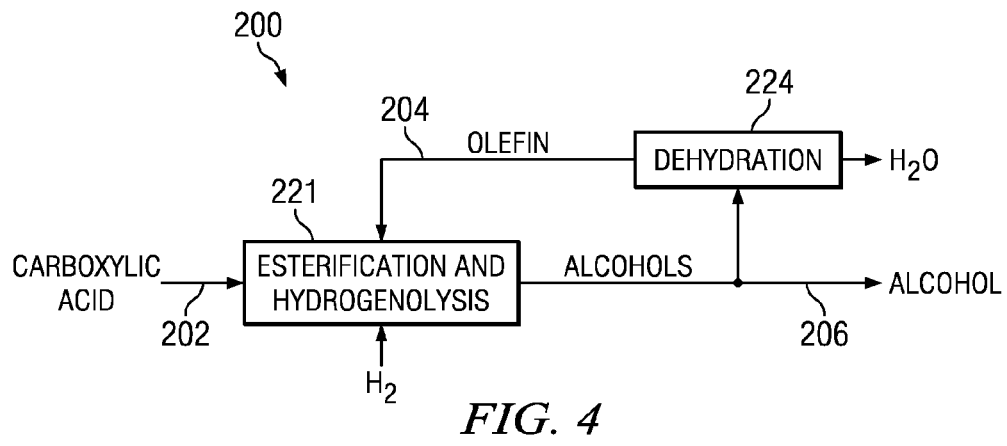
FIG. 4 is a block diagram showing conversion of carboxylic acids to alcohols in one single reactor, according to an embodiment.
Figure 5:
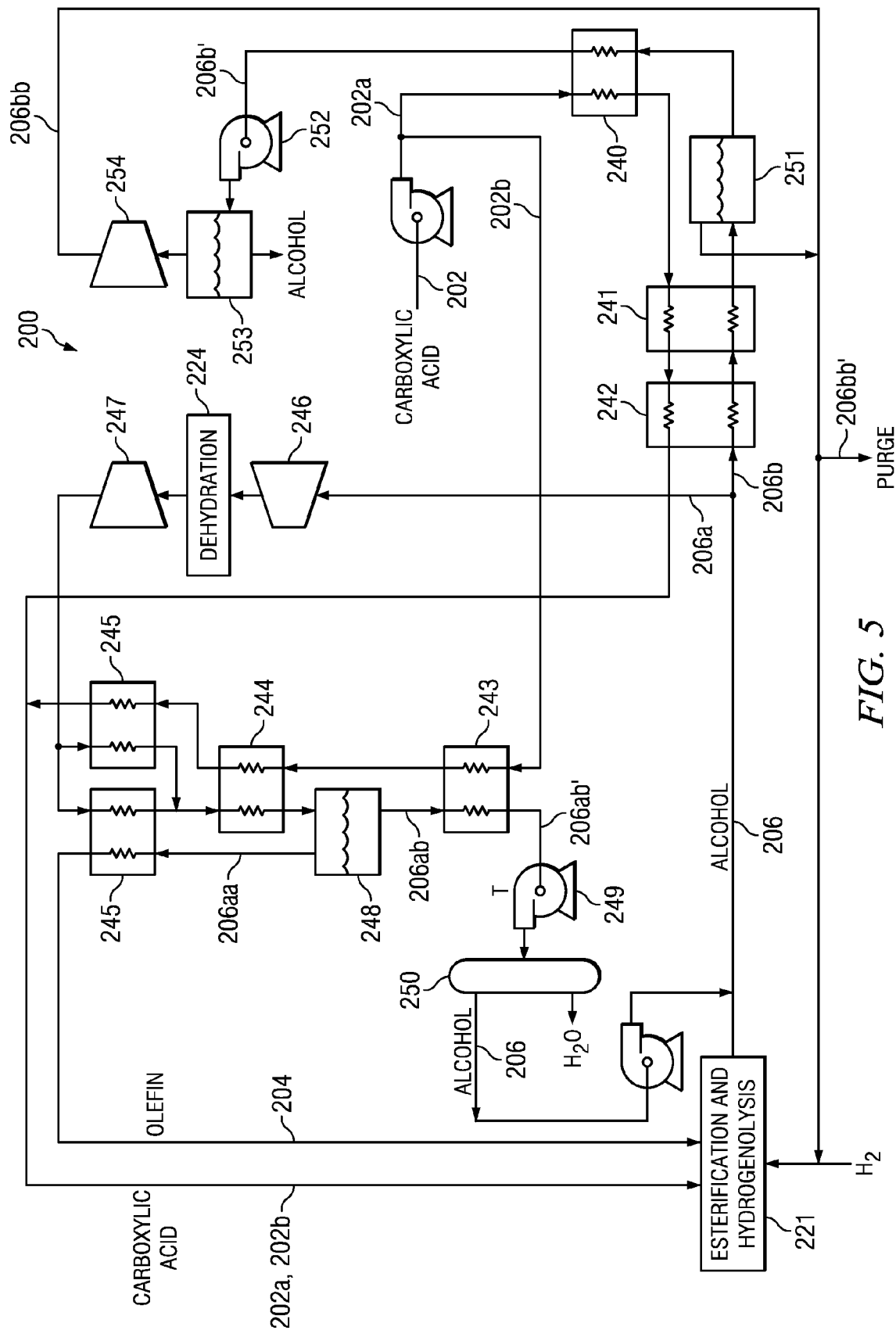
FIG. 5 is a block diagram showing details of a conversion of carboxylic acids to alcohols in one single reactor, according to an embodiment.

Certain catalysts, such as zeolites, exhibit both hydrogenation activity (e.g., but not limited to, Minachev, Kh. M., Garanin, V. I., Kharlamov, V. V., Kapustin, M. A., "Hydrogenation of acetone on cationic forms of zeolites," *Russian Chemical Bulletin* 23(7), 1472-1475 (1974)) and they also promote the reaction of olefins and carboxylic acids to produce esters (e.g., but not necessarily limited to, U.S. Pat. No. 5,973,193). Therefore, according to teachings of certain embodiments, both the hydrogenation and esterification for making alcohols may be performed in one single reactor. FIG. 4 shows a simplified diagram of system 200 with the conversion of carboxylic acids to alcohols occurring in one single reactor 221, according to an embodiment. FIG. 5 shows the detailed system 200 described in FIG. 3, but with the esterification reactor 220 and hydrogenolysis reactor 222 combined into one single reactor 221.

Figure 6:
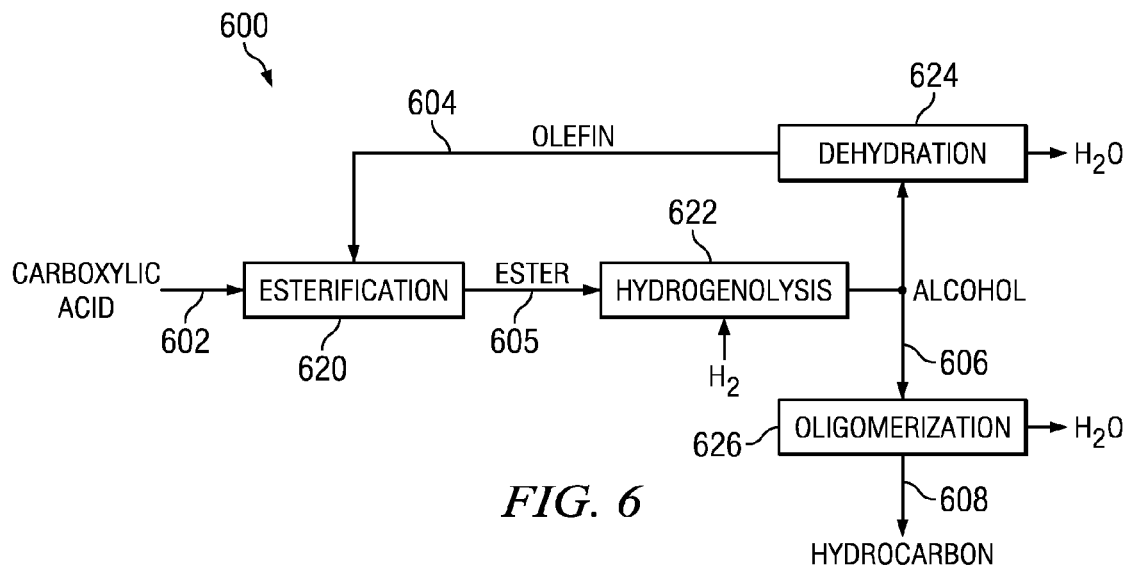
FIG. 6 is a block diagram showing conversion of carboxylic acids to hydrocarbons via olefin and alcohol (Option A), according to an embodiment.

FIG. 6 shows a block diagram of a system 600 ("Option A") for converting carboxylic acids to hydrocarbons, according to an embodiment. Carboxylic acids 602 react with olefins 604 in an esterification reactor 620 to form esters 605. The esters 605 react with hydrogen in a hydrogenolysis reactor 622 to form alcohol 606. A portion of the alcohol stream 606 is sent to the dehydration reactor 624 to produce olefins 604 and water. The remaining portion of the alcohol stream 606 is sent to the oligomerization reactor 626, where it forms hydrocarbons 608 and water.

Figure 7:
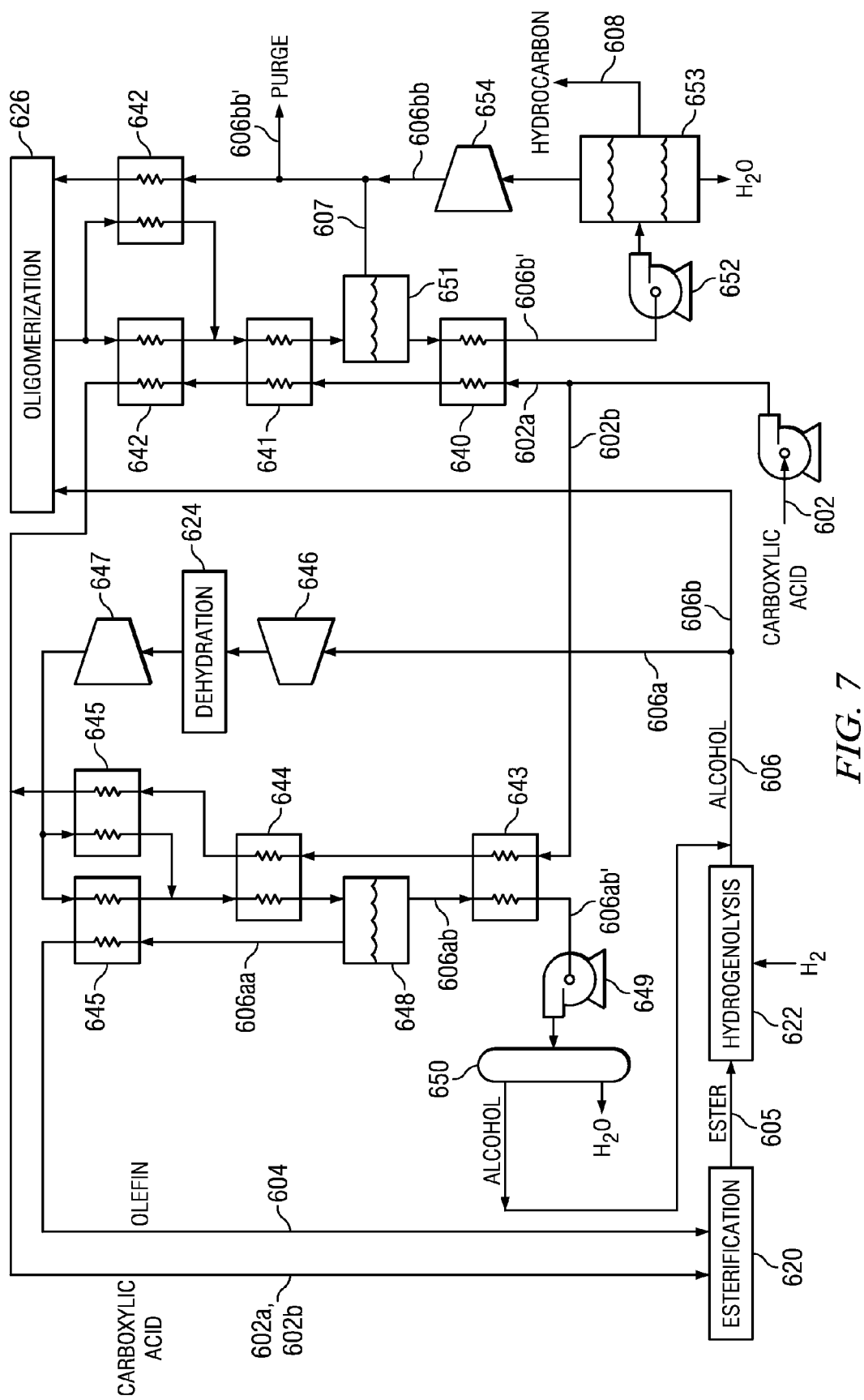
FIG. 7 is a block diagram showing details of a conversion of carboxylic acids to hydrocarbons via olefin and alcohol (Option A), according to an embodiment.
Figure 8:
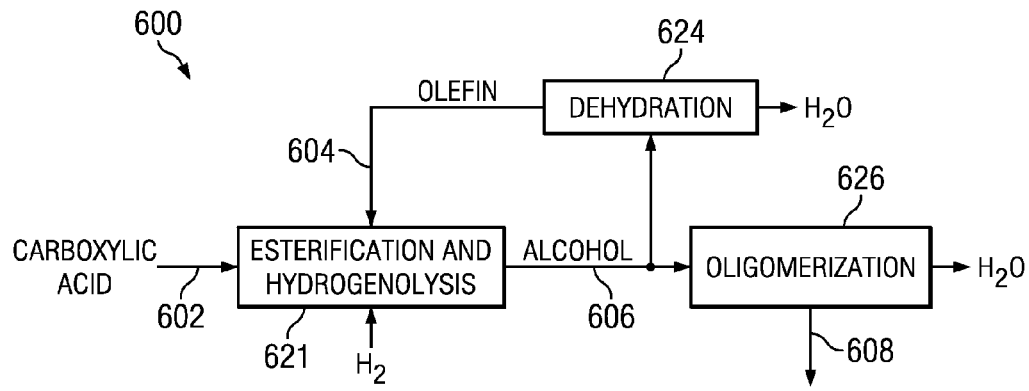
FIG. 8 is a block diagram showing conversion of carboxylic acids to hydrocarbons via olefin and alcohol with the alcohol produced in one single reactor (Option A), according to an embodiment.

FIG. 7 shows a detailed description of Option A according to one embodiment. Carboxylic acid stream 602 is split into two portions, 602a and 602b. Stream 602a is sent to sensible heat exchanger 640, latent heat exchanger 641, and sensible heat exchanger 642, such that the stream 602a becomes superheated vapor. Stream 602b is sent to sensible heat exchanger 643, latent heat exchanger 644, and sensible heat exchanger 645, such that the stream 602b becomes superheated vapor. The superheated carboxylic acids 602a and 602b react with olefins 604 in esterification reactor 620. In some embodiments, esterification reactor 620 has its own temperature control system. Esters 605 react with hydrogen in a hydrogenolysis reactor 622 to produce alcohol 606. In some embodiments, hydrogenolysis reactor 622 has its own temperature control system.

Alcohol product stream 606 is split into two streams 606a and 606b. Stream 606a enters expander 646, where the pressure is reduced. The low-pressure alcohol enters dehydration reactor 624. In some embodiments, dehydration reactor 624 has its own temperature control system. Stream 606a exiting dehydration reactor 624 (comprising olefins 606aa and water 606ab) may then be compressed in compressor 647 and enter sensible heat exchanger 645 and latent heat exchanger 644, which cools the stream and allows water 606ab to condense. Olefin 606aa and the water 606ab are separated in tank 648. Olefin 606aa is heated in sensible heat exchanger 645 so it can enter esterification reactor 620 as part of the olefin 604. Water 606ab exiting tank 648 is cooled in sensible heat exchanger 643. In some embodiments, the water 606ab may flow through a turbine 649 as part of a high-pressure liquid 606ab'. The liquid 606ab' comprises primarily water, but it may also comprise some alcohol because the dehydration reaction in dehydration reactor 624 is reversible. The alcohols in liquid 606ab' are recovered by distillation in column 650 and are returned to the alcohol stream 606.

The stream 606b is sent to the oligomerization reactor 626. In some embodiments, oligomerization reactor 626 has its own temperature control system. The product exiting oligomerization reactor 626 is cooled through sensible heat exchanger 642, latent heat exchanger 641, and sensible heat exchanger 640. Tank 651 may contain unreacted species (e.g., low-molecular-weight olefins), which may be returned via 607 to oligomerization reactor 626. In embodiments, stream 606b may flow through a turbine 652 as part of a high-pressure liquid 606b' to recover expansion energy. Tank 653 may contain unreacted species, which are compressed using compressor 654 and returned via 606bb to oligomerization reactor 626. Hydrocarbons are removed from tank 653 via 608.

Recycle streams 607 and/or 606bb may contain non-reactive gases, which may be purged via line 606bb' to prevent accumulation within the system. The purged gases may be sent to a separator to recover the reactive components, or they may be burned for process heat. Esterification reactor 620, hydrogenolysis reactor 622, and/or oligomerization reactor 626 can operate at a higher pressure (~3000 kPa), whereas dehydration reactor 624 can operate at a lower pressure (~20 to 500 kPa), according to certain embodiments. In the illustrated embodiment, expander 646 recovers energy from the pressure reduction and allows it to supplement the energy used by compressor 647.

As with FIGS. 4 and 5, FIGS. 8 and 9 show the same configuration as in FIGS. 6 and 7, but using only one reactor 621 to perform the esterification and hydrogenolysis.

Figure 10:
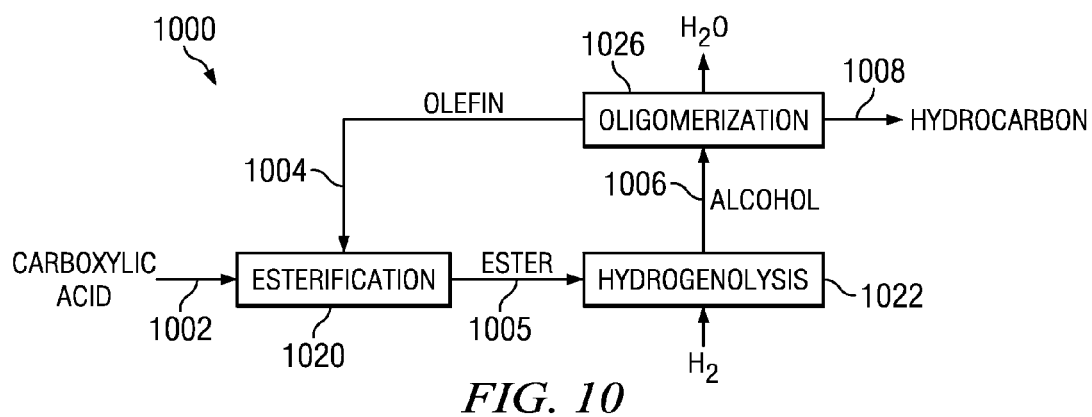
FIG. 10 is a block diagram showing conversion of carboxylic acids to hydrocarbons via olefin and alcohol (Option B), according to an embodiment.

FIG. 10 shows a block diagram of a system 1000 ("Option B") for converting carboxylic acids to hydrocarbons, according to another embodiment. Carboxylic acids 1002 react with olefins 1004 in an esterification reactor 1020 to form esters 1005. Esters 1005 are hydrogenolyzed to alcohols 1006 in a hydrogenolysis reactor 1022. The alcohol stream 1006 is sent to an oligomerization reactor 1026. In some embodiments, oligomerization reactor 1026 operates with a residence time that is short enough to form significant amounts of unreacted intermediates (olefins), which are separated from the final products, hydrocarbons 1008 and water. In the illustrated embodiment, the olefins 1004 are fed back to the esterification reactor 1020.

Figure 11:
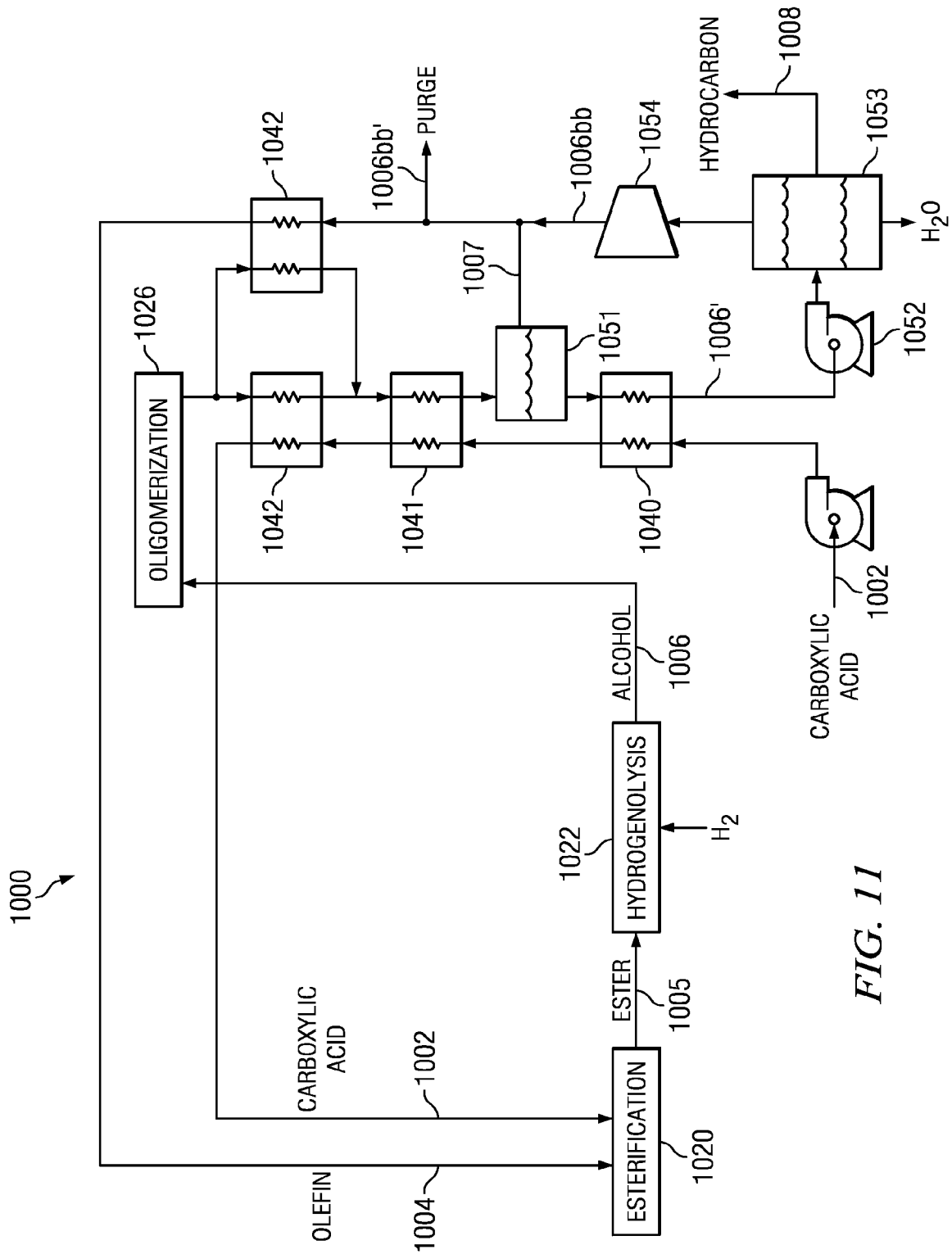
FIG. 11 is a block diagram showing details of a conversion of carboxylic acids to hydrocarbons via olefin and alcohol (Option B), according to an embodiment.

FIG. 11 shows a detailed description of Option B, according to another embodiment. Carboxylic acid stream 1002 is sent to sensible heat exchanger 1040, latent heat exchanger 1041, and sensible heat exchanger 1042, such that the carboxylic acid stream 1002 becomes superheated vapor. The superheated carboxylic acids 1002 react with olefins 1004 in the esterification reactor 1020 to produce esters 1005. In some embodiments, esterification reactor 1020 has its own temperature control system. Esters 1005 are sent to hydrogenolysis reactor 1022 to produce alcohols 1006. In some embodiments, hydrogenolysis reactor 1022 has its own temperature control system.

Alcohol stream 1006 is sent to oligomerization reactor 1026. In some embodiments, oligomerization reactor 1026 has its own temperature control system. The product exiting the oligomerization reactor is cooled through sensible heat exchanger 1042, latent heat exchanger 1041, and sensible heat exchanger 1040. In some embodiments, the stream 1006 may flow through a turbine 1052 as part of a high-pressure liquid 1006' to recover expansion energy. In embodiments, the residence time in oligomerization reactor 1026 is short enough that there is a significant amount of unreacted species (e.g., low-molecular-weight olefins) in the gas space of tank 1051, which may then be supplied to the esterification reactor 1020. Similarly, tank 1053 may contain unreacted species 1007, which may be compressed using compressor 1054 and sent to esterification reactor 1020. Hydrocarbons 1008 are removed from tank 1053.

The recycle stream 1007 and/or 1006bb may contain non-reactive gases, which may be purged 1006bb' to prevent accumulation within the system. The purged gases may be sent to a separator to recover the reactive components, or they may be burned for process heat. In certain embodiments, esterification reactor 1020, hydrogenolysis reactor 1022, and oligomerization reactor 1026 can operate at a higher pressure (3000 kPa).

Figure 12:
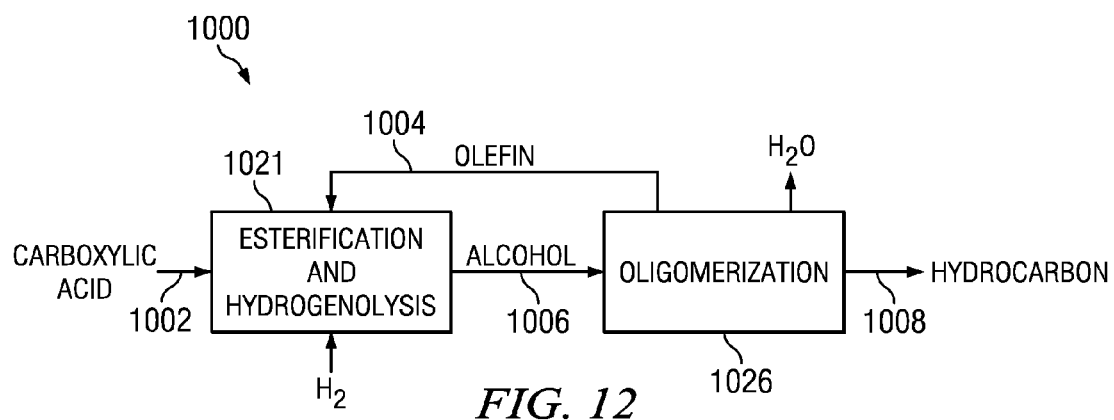
FIG. 12 is a block diagram showing conversion of carboxylic acids to hydrocarbons via olefin and alcohol with the alcohol produced in one single reactor (Option B), according to an embodiment.
Figure 9:
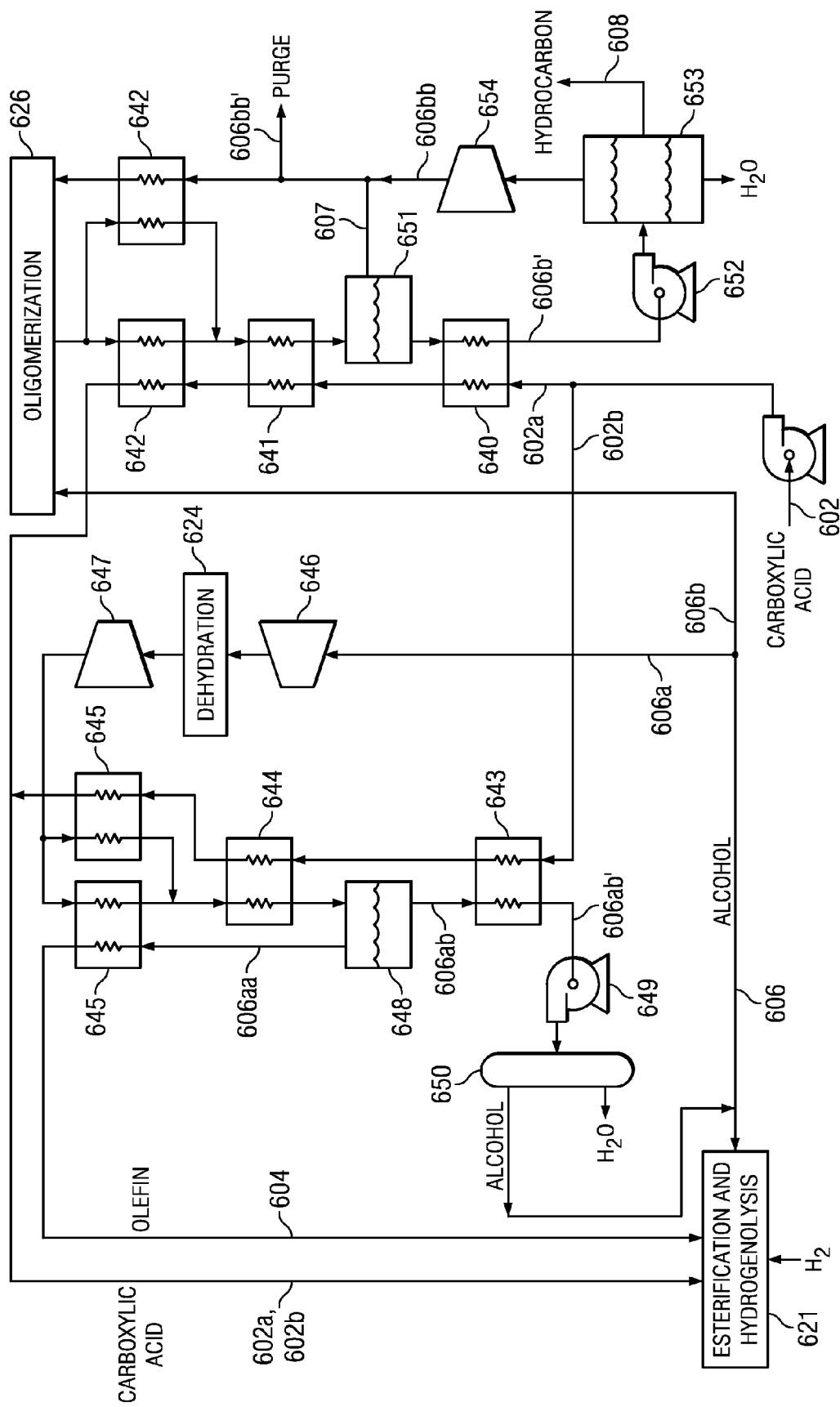
FIG. 9 is a block diagram showing details of a conversion of carboxylic acids to hydrocarbons via olefin and alcohol with the alcohol produced in one single reactor (Option A), according to an embodiment.
Figure 13:
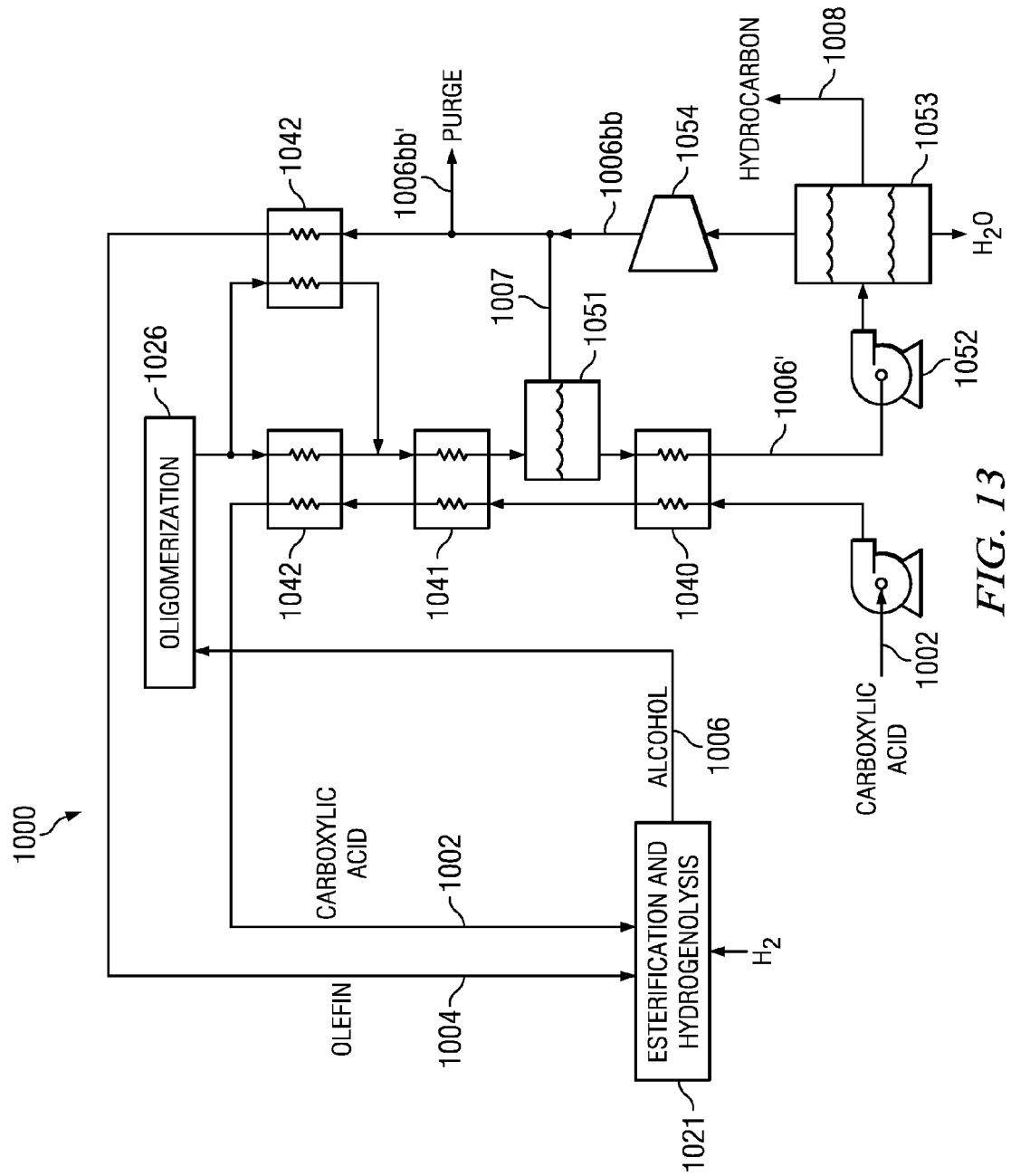
FIG. 13 is a block diagram showing details of a conversion of carboxylic acids to hydrocarbons via olefin and alcohol with the alcohol produced in one single reactor (Option B), according to an embodiment.

FIGS. 12 and 13 show the same configurations as in FIGS. 10 and 11 but using only one single reactor 1021 to perform the esterification and hydrogenolysis.

Figure 14:
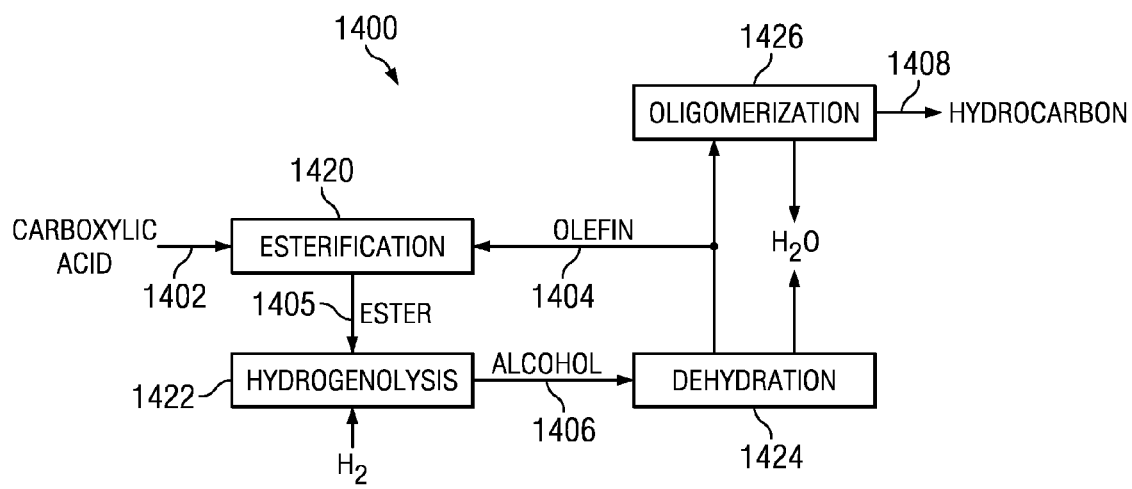
FIG. 14 is a block diagram showing conversion of carboxylic acids to hydrocarbons via olefin and alcohol (Option C), according to an embodiment.

FIG. 14 shows a block diagram of system 1400 ("Option C") for converting carboxylic acids to hydrocarbons, according to another embodiment. Carboxylic acids 1402 react with olefins 1404 in an esterification reactor 1420 to form esters 1405. The esters 1405 are hydrogenolyzed into alcohols 1406 in a hydrogenolysis reactor 1422. The alcohol stream 1406 is sent to a dehydration reactor 1424 to produce water and olefins 1404. The olefins stream 1404 is split in two portions: one stream goes to the esterification reactor 1420, and the other goes to oligomerization reactor 1426, which produces hydrocarbons 1408 and water. Because only olefins 1404 are being fed to oligomerization reactor 1426, no water should be produced during the oligomerization; however, teachings of some embodiments recognize that some alcohol may be expected in the olefin stream going to oligomerization reactor 1426. In the presence of hydrogen (which remains from the hydrogenolysis) and carbon monoxide (which can be formed in dehydration reactor 1424), methanol and other alcohols can be formed in oligomerization reactor 1426; therefore, water may form.

Figure 15:
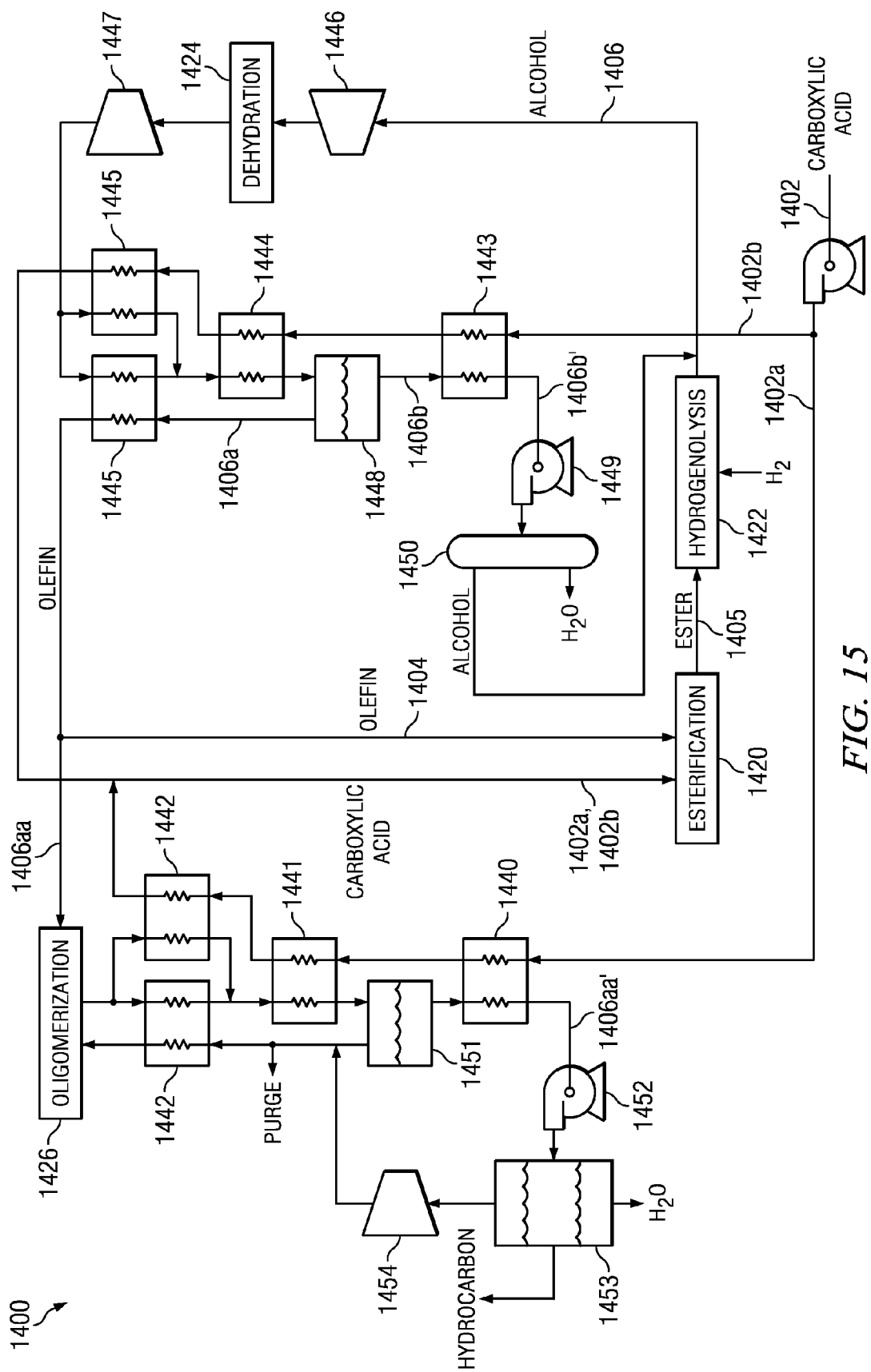
FIG. 15 is a block diagram showing details of a conversion of carboxylic acids to hydrocarbons via olefin and alcohol (Option C), according to an embodiment.

FIG. 15 shows a detailed description of Option C, according to another embodiment. Carboxylic acid stream 1402 is split into two portions, 1402a and 1402b. Stream 1402a is sent to sensible heat exchanger 1440, latent heat exchanger 1441, and sensible heat exchanger 1442, such that stream 1402a becomes superheated vapor. Stream 1402b is sent to sensible heat exchanger 1443, latent heat exchanger 1444, and sensible heat exchanger 1445, such that stream 1402b becomes superheated vapor. The superheated carboxylic acids 1402a and 1402b react with olefins 1404 in esterification reactor 1420 to produce esters 1405. In embodiments, esterification reactor 1420 has its own temperature control system. Esters 1405 are sent to hydrogenolysis reactor 1422 to produce alcohols 1406. In embodiments, hydrogenolysis reactor 1422 has its own temperature control system.

Alcohol product stream 1406 enters expander 1446, where the pressure is reduced. The low-pressure alcohols enter dehydration reactor 1424. In some embodiments, dehydration reactor 1424 has its own temperature control system. The stream 1406 (comprising olefins 1406a and water 1406b)

exiting dehydration reactor 1424 is compressed using compressor 1447 and enters sensible heat exchanger 1445 and latent heat exchanger 1444, which cools the stream 1406 and allows water 1406b to condense. Olefins 1406a and water 1406b are separated in tank 1448. Olefins 1406a are re-heated in sensible heat exchanger 1445. Olefin stream 1406a is split into two portions: 1406aa and 1406ab. Stream 1406aa is sent to oligomerization reactor 1426, and stream 1406ab is sent to esterification reactor 1420. Water 1406b exiting tank 1448 is cooled in sensible heat exchanger 1443. In embodiments, water 1406b flows through a turbine 1449 as part of a high-pressure liquid 1406b'. The liquid 1406b' comprises primarily water, but may also comprise some alcohol because the reaction in dehydration reactor 1424 is reversible. The alcohols in liquid 1406b' are recovered by distillation in column 1450 and are returned to alcohol stream 1406.

The product exiting oligomerization reactor 1426 is cooled through sensible heat exchanger 1442, latent heat exchanger 1441, and sensible heat exchanger 1440. In some embodiments, stream 1406aa flows through a turbine 1452 as part of a high-pressure liquid 1406aa' to recovery energy expansion. The gas space in tank 1451 may contain unreacted species (e.g., low-molecular-weight olefins), which are returned to the oligomerization reactor 1426. Similarly, tank 1453 may contain unreacted species, which are compressed using compressor 1454 and returned to oligomerization reactor 1426.

The recycle stream may contain non-reactive gases, which may be purged to prevent accumulation within the system. The purged gases may be sent to a separator to recover the reactive components, or they may be burned for process heat. Esterification reactor 1420, hydrogenolysis reactor 1422, and/or oligomerization reactor 1426 can operate at a higher pressure (~3000 kPa), whereas the dehydration reactor 1424 operates at a lower pressure (~20 to 500 kPa), according to certain embodiments. In the illustrated embodiment, expander 1446 recovers energy from the pressure reduction and allows it to supplement the energy used by compressor 1447.

Figure 16:
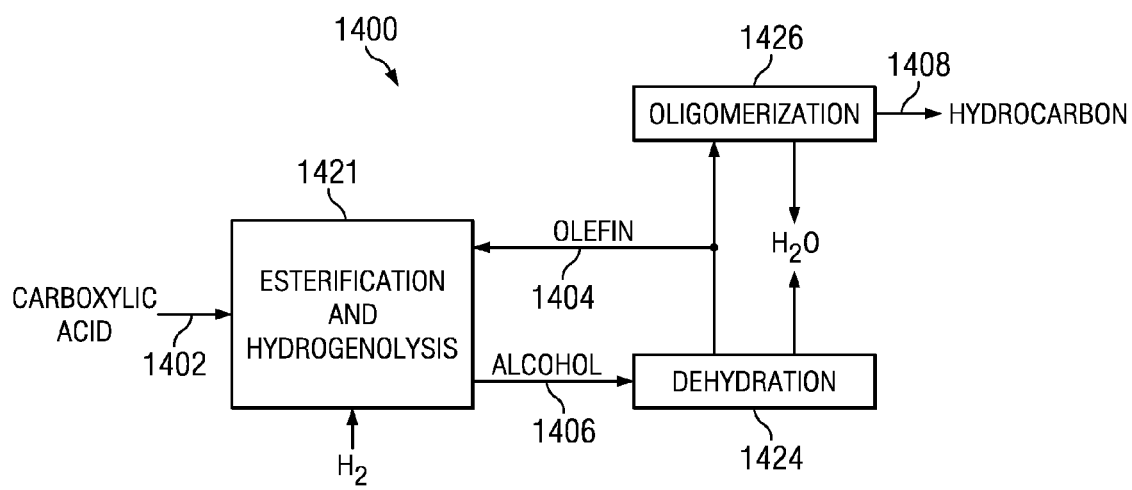
FIG. 16 is a block diagram showing conversion of carboxylic acids to hydrocarbons via olefin and alcohol with the alcohol produced in one single reactor (Option C), according to an embodiment.
Figure 17:
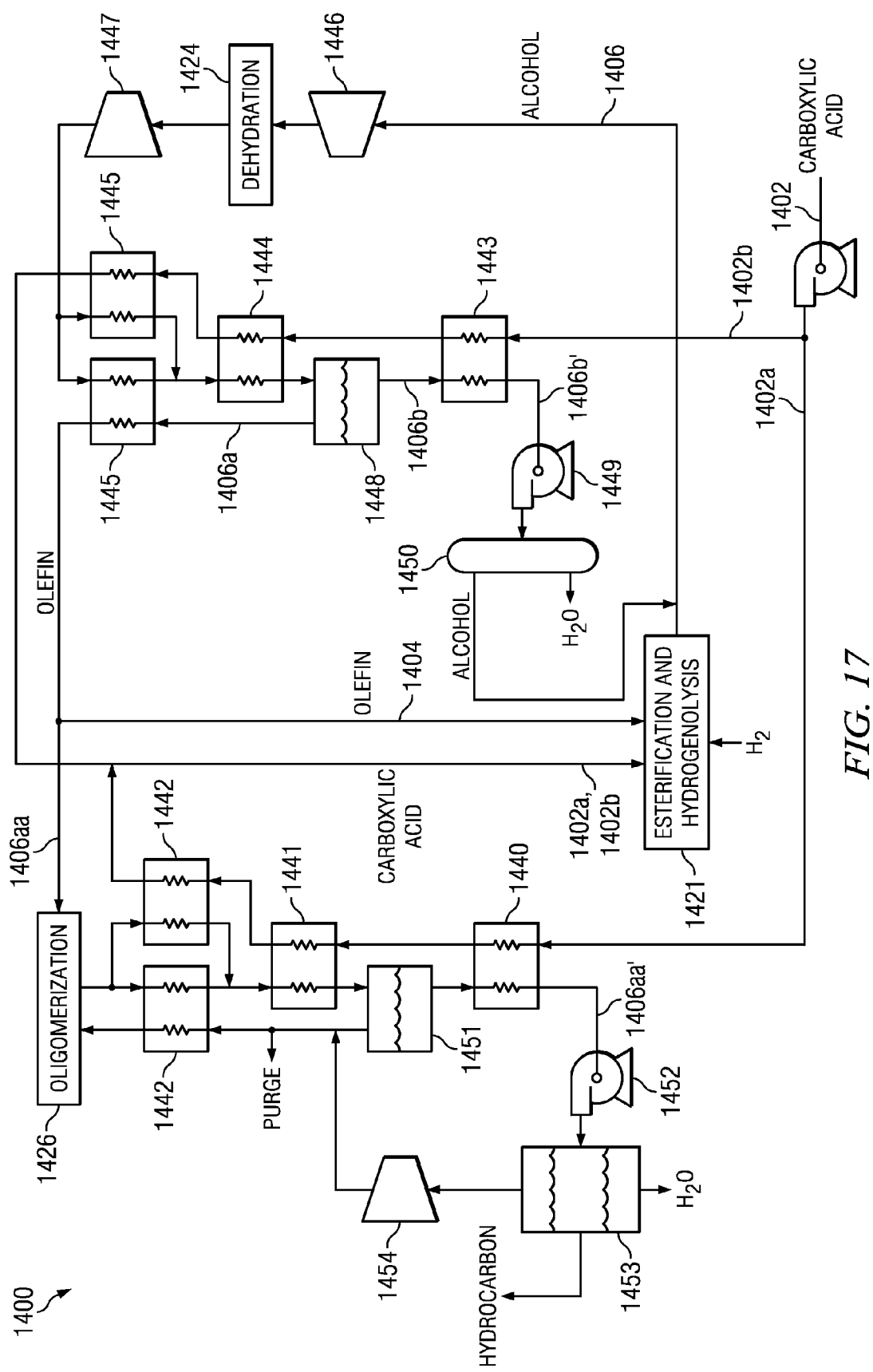
FIG. 17 is a block diagram showing details of a conversion of carboxylic acids to hydrocarbons via olefin and alcohol with the alcohol produced in one single reactor (Option C), according to an embodiment.

FIGS. 16 and 17 show the same configuration as in FIGS. 14 and 15 but using a single reactor 1421 to perform the esterification and hydrogenolysis.

Figure 18:
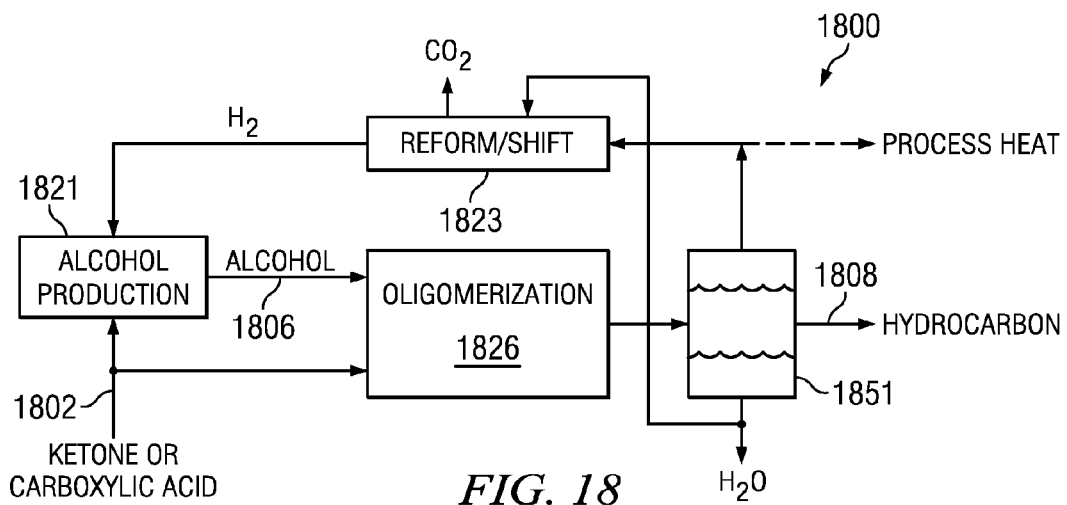
FIG. 18 is a block diagram showing direct conversion of carboxylic acids or ketones to hydrocarbons (Option A1), according to an embodiment.

FIG. 18 shows a block diagram of a system 1800 ("Option A1") for converting ketones or carboxylic acids directly to hydrocarbons in the oligomerization reactor, according to another embodiment. The ketones or carboxylic acids 1802 feed into an oligomerization reactor 1826. The products that exit oligomerization reactor 1826 may be separated in a tank 1851 into water, hydrocarbons 1808, and gaseous products. In some embodiments, gaseous product may represent 30-40% of the products that exit the oligomerization reactor 1826. The gaseous product may be burned for process heat or reformed into hydrogen in a reformer 1823 using standard technology (e.g., steam reforming, partial oxidation, or other suitable systems and methods). The hydrogen may be used to convert a portion of the ketones or carboxylic acids 1802 into alcohols 1806 in an alcohol reactor 1821; these alcohols 1806 may then be sent to the oligomerization reactor 1826.

If ketones are used as the feed, then hydrogenation may be very direct using appropriate hydrogenation catalyst (e.g., Raney nickel, platinum, copper chromite, or other suitable hydrogenation catalyst). If carboxylic acids are used as the feed, then alcohol production 1821 may include one of the processes described in FIGS. 2 through 5. The details of the process may be similar to those described in FIGS. 3, 5, 7, 9, 11, 13, 15 and 17, which use appropriate sensible and latent heat exchangers to heat and cool the process streams, as well as compressors and expanders to manipulate the pressure. These details are not repeated.

Figure 19:
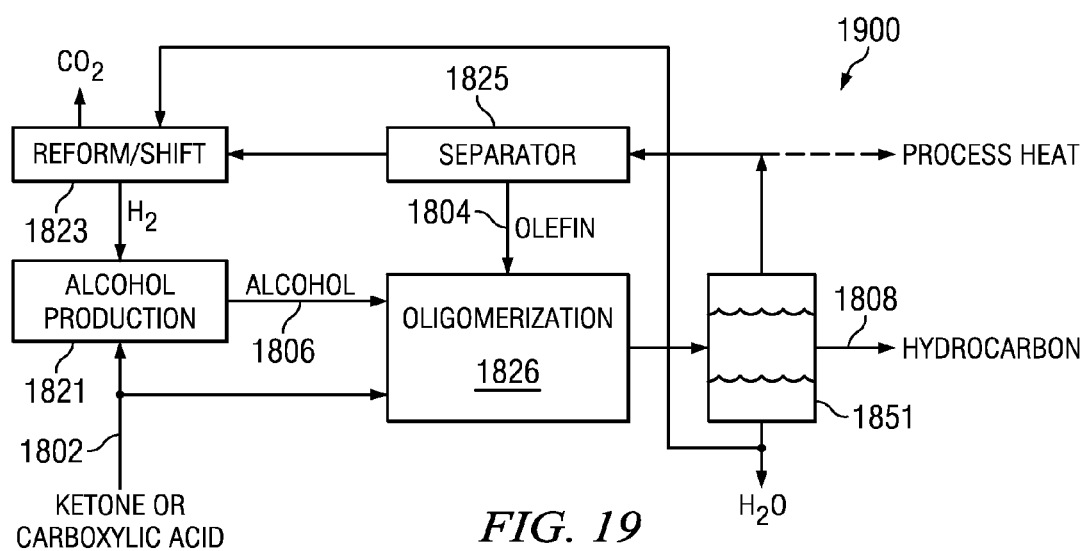
FIG. 19 is a block diagram showing direct conversion of carboxylic acids or ketones to hydrocarbons (Option B1), according to an embodiment.

FIG. 19 shows a block diagram of a system 1900 ("Option B1") for converting ketones or carboxylic acids directly to hydrocarbons in the oligomerization reactor. This embodiment incorporates a separator 1825 (e.g., pressure-swing adsorption, membranes, cryogenic distillation) into Option A1 to recover olefins 1804 from the gaseous stream and return them to oligomerization reactor 1826 rather than sending them to reformer 1823.

Figure 20:
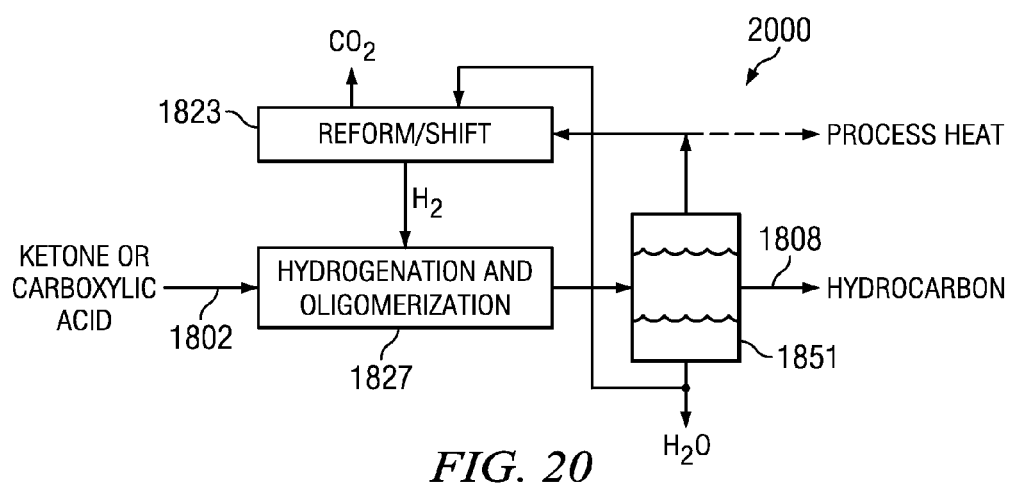
FIG. 20 is a block diagram showing direct conversion of carboxylic acids or ketones to hydrocarbons (Option A2), according to an embodiment.

FIG. 20 shows a block diagram of a system 2000 ("Option A2") for converting ketones or carboxylic acids directly to hydrocarbons. This embodiment modifies Option A1 by incorporating the alcohol production (e.g., hydrogenation) and oligomerization mechanisms into a single reactor 1827. Teachings of certain embodiments recognize that, because the same catalysts employed for oligomerization are known to effect hydrogenation as well (e.g., U.S. Pat. No. 3,894,107 and Minachev, Kh. M., Garanin, V. I., Kharlamov, V. V., Kapustin, M. A., "Hydrogenation of acetone on cationic forms of zeolites," *Russian Chemical Bulletin* 23(7), 1472-1475 (1974)), the ketones or the carboxylic acids and hydrogen may be fed directly to the same reactor, thus avoiding having a separate hydrogenation reactor and other equipment needed for alcohol generation.

Figure 21:
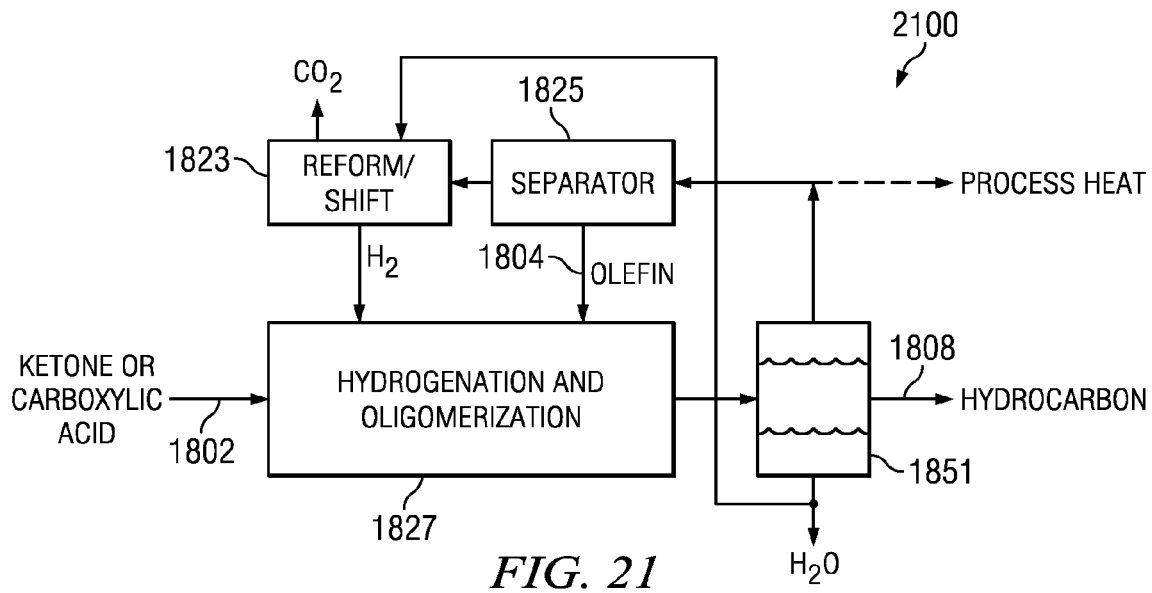
FIG. 21 is a block diagram showing direct conversion of carboxylic acids or ketones to hydrocarbons (Option B2), according to an embodiment.

FIG. 21 shows a block diagram of a system 2100 ("Option B2") for converting ketones or carboxylic acids directly to hydrocarbons. This embodiment modifies Option B1 by incorporating the alcohol production (e.g., hydrogenation) and oligomerization mechanisms into a single reactor 1827. Teachings of certain embodiments recognize that, because the same catalysts employed for oligomerization are known to effect hydrogenation as well, the ketones or the carboxylic acids and hydrogen may be fed directly to the same reactor, thus avoiding having a separate hydrogenation reactor and other equipment needed for alcohol generation.

Figure 22:
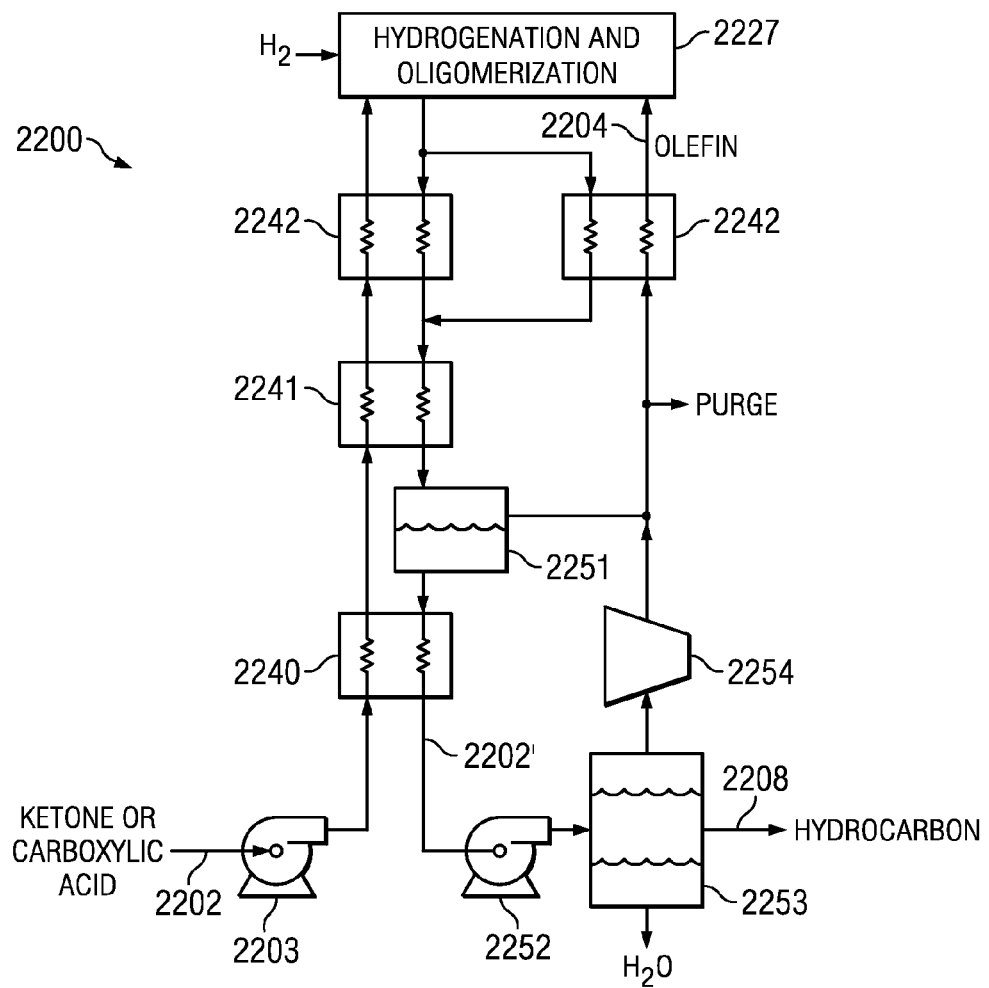
FIG. 22 is a block diagram showing details of conversion of carboxylic acids or ketones to hydrocarbons (Options A2 and B2), according to an embodiment.

FIG. 22 shows a detailed process flow diagram of a system 2200 for the direct conversion of carboxylic acids or ketones to hydrocarbons using a single reactor for both hydrogenation and oligomerization (based on Option A2 of FIG. 20 and Option B2 of FIG. 21) according to one embodiment. The carboxylic acid or ketone stream 2202 is sent (e.g., via feed pump 2203) to sensible heat exchanger 2240, latent heat exchanger 2241, and sensible heat exchanger 2242, such that the stream 2202 becomes superheated vapor. The superheated carboxylic acids or ketones and hydrogen are sent to the hydrogenation/oligomerization reactor 2227. In some embodiments, hydrogenation/oligomerization reactor 2227 has its own temperature control system. The product exiting hydrogenation/oligomerization reactor 2227 is cooled through sensible heat exchanger 2242, latent heat exchanger 2241, and sensible heat exchanger 2240. In some embodiments, this high pressure liquid flows through a turbine 2252 as part of a high-pressure liquid 2202' to recover expansion energy. There may be unreacted species (e.g., low-molecular-weight olefins) in the gas space of tank 2251, which may be recycled to hydrogenation/oligomerization reactor 2227. Similarly, tank 2253 may contain unreacted species, which may be compressed using compressor 2254 and sent back to the hydrogenation/oligomerization reactor 2227. Hydrocarbons 2208 may be removed from tank 2253.

The recycle stream may contain non-reactive gases, which may be purged to prevent accumulation within the system. The purged gases may be sent to a separator to recover the reactive components, or they may be burned for process heat or reformed into hydrogen. Hydrogenation/oligomerization reactor 2227 may operate at a higher pressure (~3000 kPa), according to certain embodiments.

Figure 23:
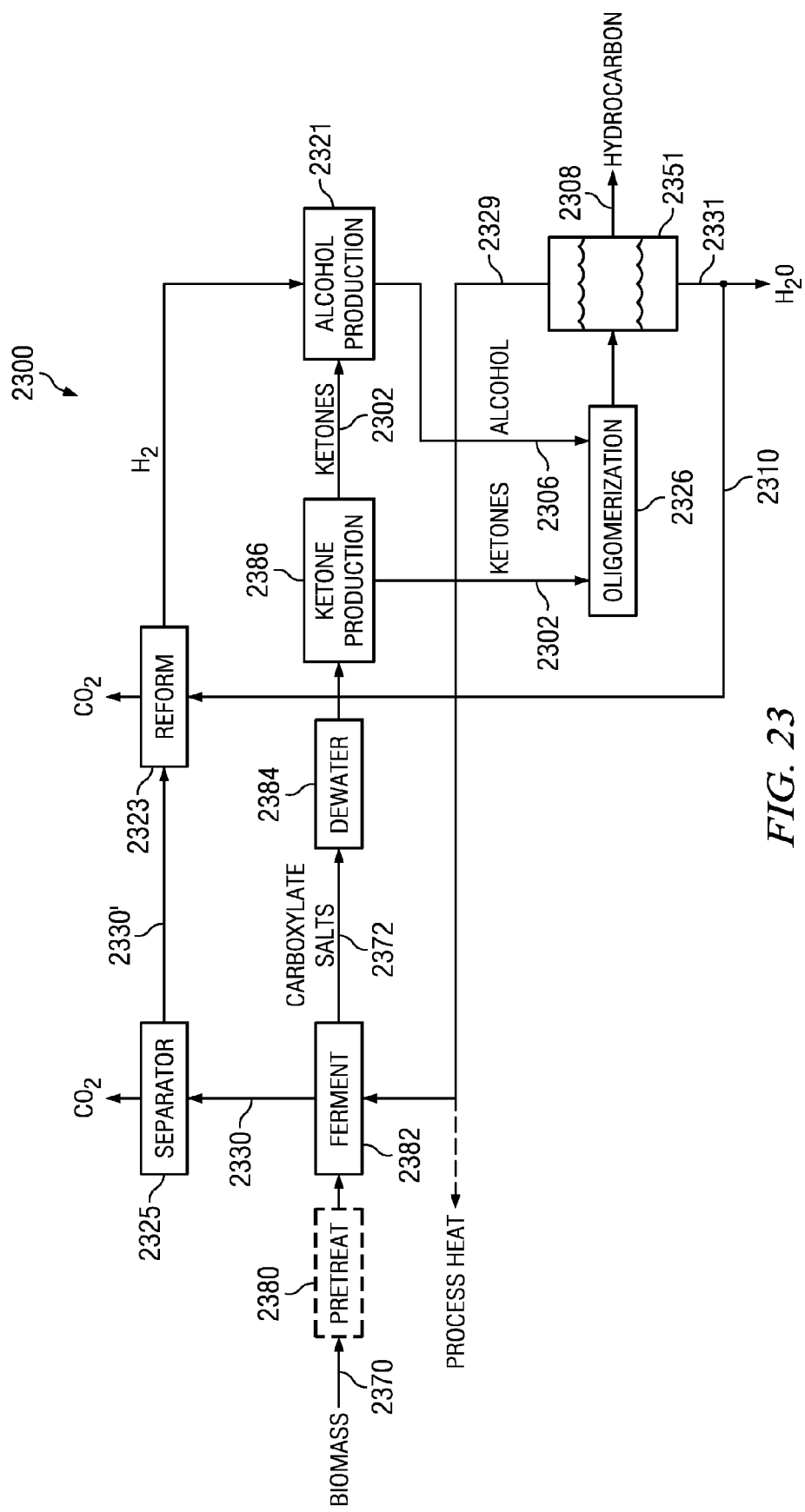
FIG. 23 is a block diagram showing fermentation with direct conversion of ketones to hydrocarbons, according to an embodiment.

FIG. 23 shows a block diagram for an embodiment of a system 2300 that directly converts ketones to hydrocarbons, which corresponds to one of the routes shown in FIG. 1A. In the illustrated embodiment, biomass 2370 is optionally pretreated 2380 to enhance biodegradability using lime (e.g., using, but not limited to, lime pretreatment described in, but not limited to, U.S. Pat. Nos. 5,693,296 and 5,865,898, and U.S. Pat. App. Nos. 60/423,288 and 60/985,059). Then, the pretreated biomass 2370 is directly fermented in the fermenter 2382, creating carboxylate salts 2372 (e.g., as described in, but not limited to, U.S. Pat. No. 5,962,307 and U.S. patent application Ser. Nos. 11/298,983 and 11/456,653). The resulting carboxylate salts 2372 are dewatered and, as a result, concentrated (e.g., using processes or systems described in, but not limited to, U.S. Pat. Nos. 5,986,133, 7,251,944, and 7,328,591 and U.S. Pat. App. No. 60/985,059) in a concentrator 2384. The concentrated salts are converted to ketones 2302 (e.g., using processes or systems described in, but not limited to, U.S. Pat. Nos. 6,043,392 and 6,262,313) at ketone reactor 2386. Ketones 2302 may be directly converted to hydrocarbons 2308 and alcohols 2306 in a manner similar to the processes described in FIGS. 18-22. However, in the illustrated embodiment, the gases 2329 from oligomerization reactor 2326 are directed to the fermenter 2382, for example, through tank 2351. In the fermenter 2382, biologically reactive species (e.g., hydrogen and carbon monoxide) are converted to carboxylate salts 2372. Carbon dioxide is removed from the energetic gases (e.g., hydrogen, methane) 2330' exiting fermenter 2382 in fermenter exit gas 2330 via a separator 2325 using standard methods (e.g., amine adsorption, membranes, cryogenics). Energetic gases 2330' are sent to a reformer 2323 to produce hydrogen for alcohol reactor 2321. All or a portion (2310) of the water 2331 that exits oligomerization reactor 2326 may be used in the reformer 2323, for example after separation in tank 2351.

Figure 24:
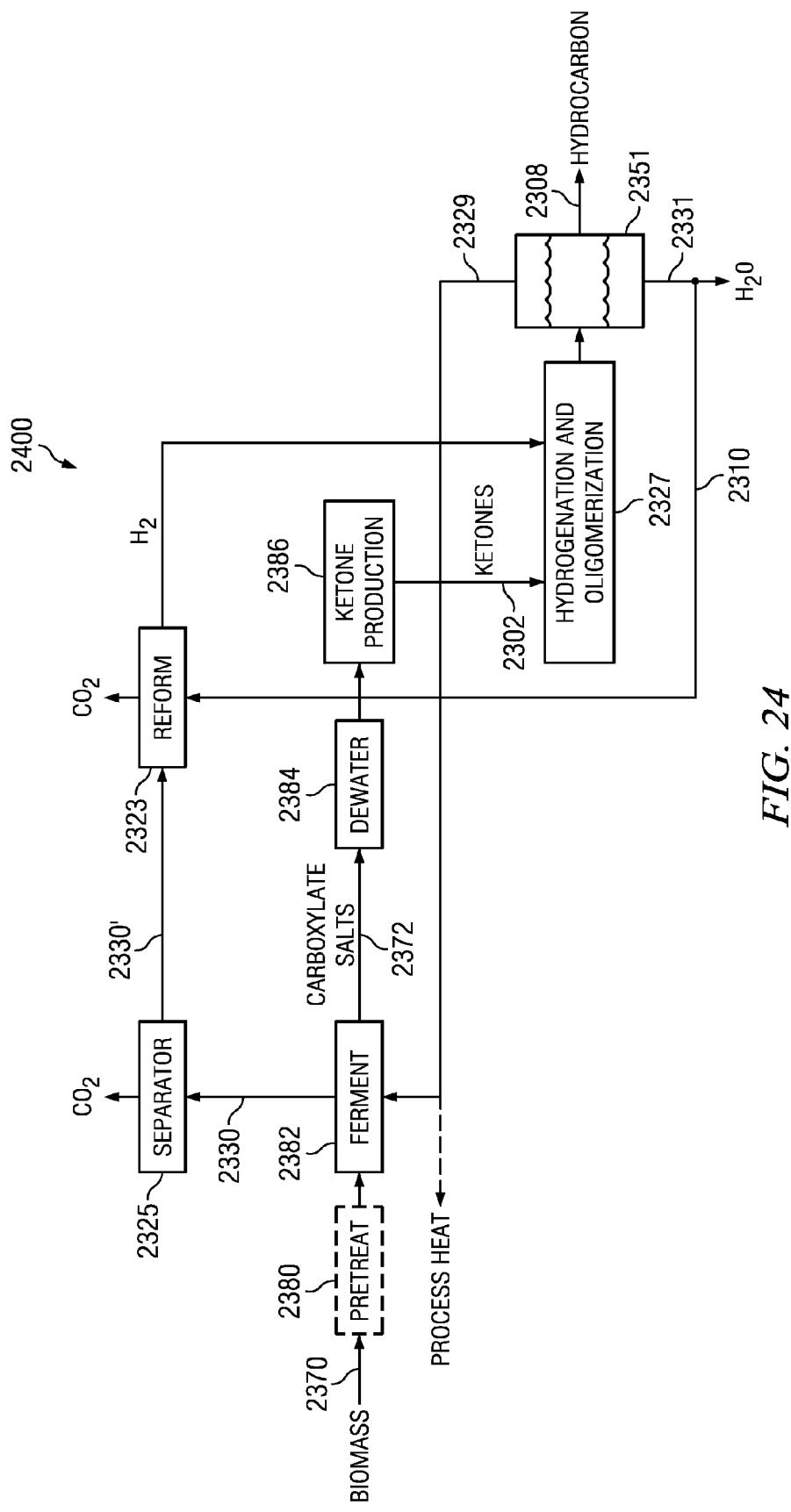
FIG. 24 is a block diagram showing fermentation with direct conversion of ketones to hydrocarbons with hydrogenation and oligomerization occurring in the same reactor, according to an embodiment.

FIG. 24 shows a block diagram of a system 2400 that directly converts ketones to hydrocarbons, which corresponds to one of the routes shown in FIG. 1A, according to one embodiment. This embodiment modifies system 2300 by incorporating the alcohol production (e.g., hydrogenation) and oligomerization mechanisms into a single reactor 2327, with both the ketones and the hydrogen fed to this reactor.

Figure 25:
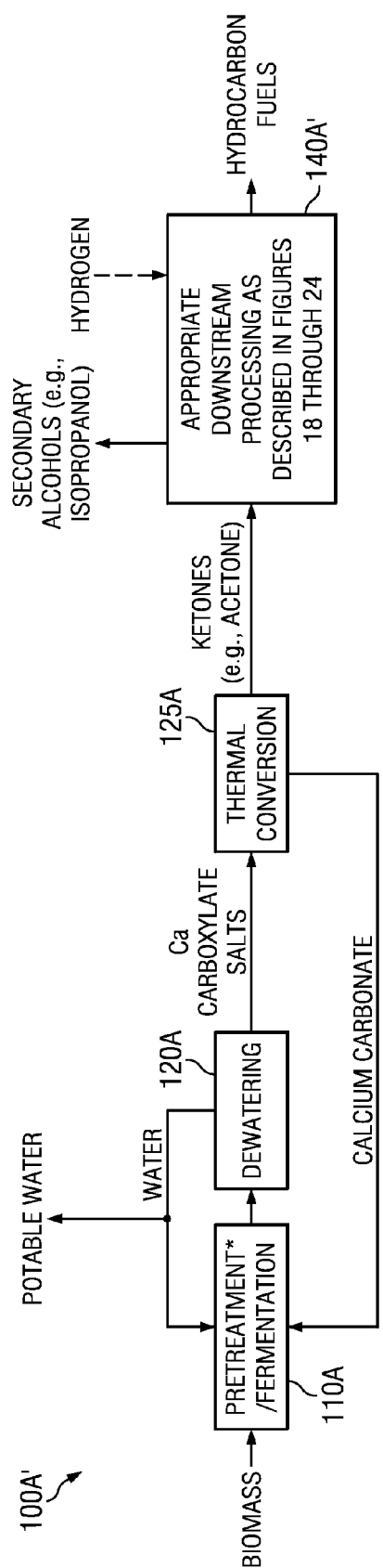
FIG. 25 is a block diagram showing complete biomass conversion for calcium-based systems, according to embodiments.

As mentioned and indicated in FIG. 1, in embodiments, biomass may be converted to hydrocarbons using a calcium-based system. Via this process, ketone production from carboxylate salts is integrated with subsequent conversion of the ketones into alcohols and hydrocarbons. FIG. 25, a subset of FIG. 1, is a block diagram showing complete biomass conversion for calcium-based systems, according to an embodiment. The first step in the process is pretreatment (e.g., but not limited to, lime pretreatment). Such lime pretreatment is described, for example, but not limited to, in U.S. Pat. Nos. 5,693,296 and 5,865,898 as well as in U.S. Pat. App. Nos. 60/423,288 and 60/985,059. Such pretreatment is optional if the raw biomass is sufficiently digestible. The digestible biomass is then directly fermented to carboxylate salts. Such fermentation may be performed as described, for example, but not limited to, in U.S. Pat. No. 5,962,307 and U.S. patent application Ser. Nos. 11/298,983 and 11/456,653. From the fermentation, a liquid fermentation broth is obtained, which comprises mostly water and the carboxylate salts. For further treatment, the carboxylate salts may be concentrated, for example, but not limited to, via dewatering 120A as described in U.S. Pat. Nos. 5,986,133, 7,251,944 and 7,328,591 and U.S. Pat. App. No. 60/985,059. In the case currently being considered, where calcium carboxylate salts have been created, such calcium carboxylate salts may be thermally converted 125A into ketones. Such thermal conversion may be performed, for example, but not limited to, as described in U.S. Pat. No. 6,262,313. Ketones may also be generated by passing carboxylic acids through a catalytic bed of, for example, zirconium oxide. The resulting ketones may be sent downstream to be processed as described hereinabove with respect to FIGS. 18-24. Thus, in such embodiments, appropriate downstream processing 140A' may be performed as described in FIGS. 18-24.

Ketones produced in a ketone reactor by the dry distillation of carboxylate salts must be removed and cooled down quickly to avoid degradation. Prior art methods utilize a vacuum to reduce residence time in the ketone reactor, requiring vacuum and chilling equipment. For example, in U.S. Pat. No. 6,262,313, carboxylate salts are thermally converted to ketones, by heating under vacuum and subsequent condensation and recovery. As mentioned, the vacuum and condensation help increase yields by quickly removing ketones from the hot reaction zone, thus avoiding degradation, however, avoidance of such vacuum conditions may be more economically desirable.

Figure 26:
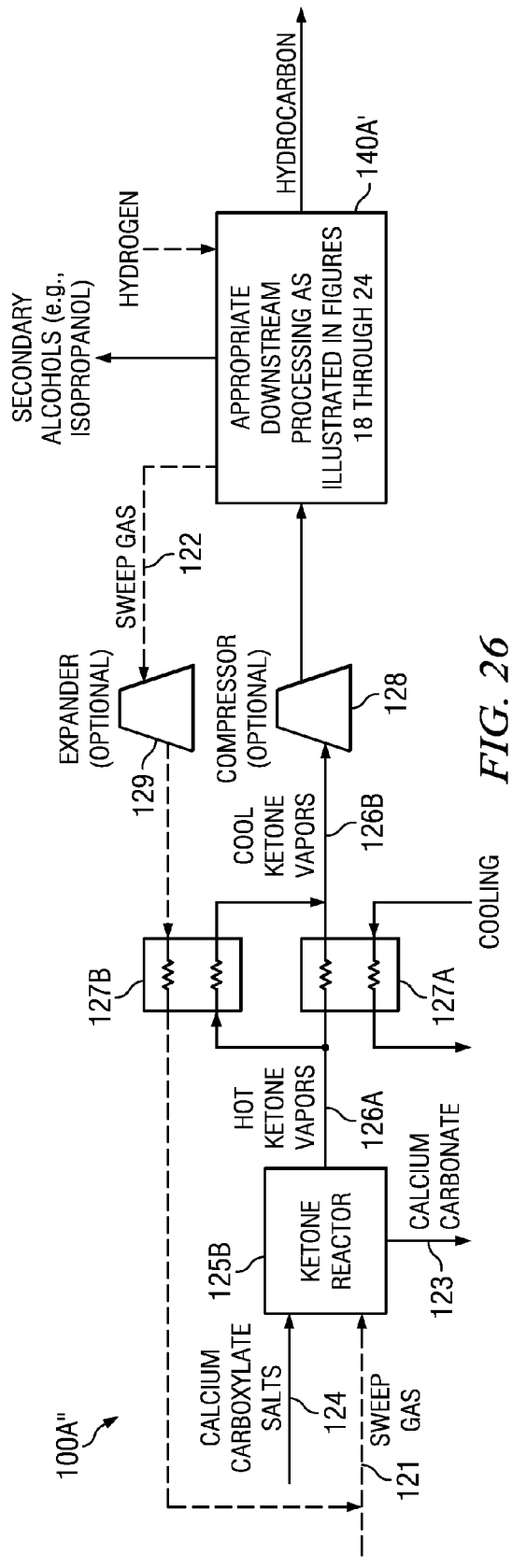
FIG. 26 is a block diagram showing the use of sweep gas and the direct introduction of ketone vapors from a ketone reactor to downstream unit operations, according to an embodiment.

This same goal to avoid ketone degradation can be accomplished by using a sweep gas, which eliminates the capital associated with maintaining a vacuum and oversizing chillers. In embodiments, a ketone reactor is integrated with downstream unit operations for producing alcohols and hydrocarbons (e.g., as described in FIGS. 18-24) utilizing a sweep gas. FIG. 26 is a block diagram showing a system 100A" incorporating the use of sweep gas and the direct introduction of ketone vapors from the ketone reactor to downstream unit operations, according to an embodiment;

As shown in FIG. 26, costly vacuum and oversized chillers can be avoided by introducing a sweep gas 121. In this embodiment, calcium carboxylate salts 124 are introduced into ketone reactor 125B along with sweep gas 121. Condensing ketones may be avoided if the hot ketone vapors 126A exiting ketone reactor 125B are cooled, for example via heat exchanger 127A to avoid degradation and cooled ketone vapors 126B are sent to the next unit operation 140', as described in FIGS. 18-24 hereinabove. In this manner, ketones produced from dry distillation of carboxylate salts may be directly sent to alcohol or gasoline conversion without the need for condensation, thus saving capital on the downstream condensation, heating, and vaporization equipment. Because sweep gas rapidly removes ketones formed in ketone reactor 125B, substantial capital savings are expected by eliminating vacuum and chilling equipment needed to remove and condense low-pressure ketones, which were required by the previous vacuum schemes.

It should be noted that the use of the sweep gas and the direct introduction of the ketone vapors from the ketone reactor to the unit operations downstream can be used together or may be employed independently. When the ketone vapors from ketone reactor 125B are sent directly to downstream conversion 140', with or without the aid from a sweep gas, the feed pump 2203, sensible heat exchanger 2240, and latent heat exchanger 2241 shown in FIG. 22 may no longer be utilized or needed. Because ketone vapors from ketone reactor 125B directly react in downstream unit operations 140', substantial capital saving may be realized by eliminating the condensing equipment, peripherals, and downstream equipment needed to re-vaporize ketones, which were required by prior art vacuum processes. Reacting ketone vapors directly into hydrocarbon or alcohols may also reduce material losses typical when separate unit operations are employed, such as condensing. In addition, avoiding liquid heating or cooling may allow for higher energy efficiencies.

Other than oxidants (e.g., oxygen), many gases may be employed as sweep gas. If the sweep gas option is practiced and it is desired to condense the ketones, a condensing sweep gas can be employed, to minimize/avoid the loss of ketones vapors that may occur with a non-condensing sweep gas, such as nitrogen. An example of such a condensing sweep gas is steam. Simulations with HYSYS suggest that virtually no ketones are lost when steam is used as the sweep gas. Steam has the added advantage that, when hydrocarbons are the final product, when the steam condenses, it is immiscible with hydrocarbons and is easily separated therefrom.

As mentioned, the sweep gas may be any gas other than oxidants (e.g., oxygen), but the use of hydrogen may be desired in instances where hydrogen is used downstream to hydrogenate some or all the ketones. Thus, when producing alcohols or hydrocarbons, hydrogen is a desirable sweep gas because it is also a reactant. To maintain a low partial pressure of ketones in the ketone reactor 125B, it may be desirable to recycle substantial quantities of hydrogen. In such embodiments, gas 122 from downstream processing 140A' may be recycled to ketone reactor 125B. The recycle gas 122 may be passed through countercurrent heat exchanger 127B for recycle to ketone reactor 125B.

The literature describes the use of nitrogen sweep gas (Ardagh, E. G. R., Barbour, A. D., McClellan, G. E., and McBride, E. W. (1924). Distillation of acetate of lime, Industrial and Engineering Chemistry, 16, 1133-1139). However, nitrogen is both inert and noncondensable. According to this disclosure, a reactive (e.g., hydrogen) or condensable (e.g., steam) sweep gas is utilized.

When sweep gas is employed, an important consideration is whether hydrocarbon conversion occurs at the same pressure as the ketone reactor, i.e., pressures from vacuum to 1 atm. Experiments have shown that hydrocarbon conversion of ketones and secondary alcohols over H-ZSM-5 zeolite is feasible at 1 atm. In such case, vapors are sent directly to the downstream unit operation after sufficient cooling and heating. If, however, the pressure desired in downstream processing 140A' is higher, a compressor 128 may be used. If sweep gas is being recycled, an expander 129 and/or a countercurrent heat exchanger 127B may be used, for example, to improve energy efficiency.

If the pressure and temperature of the ketone conversion and hydrocarbon conversion reactions are similar, a simpler method may be implemented. In this case, the catalyst can be placed in the exhaust ports of ketone reactor 125B so that the ketones react when exiting ketone reactor 125B.

In some of these embodiments and some downstream unit operations for converting ketones into hydrocarbons, a dual-catalyst bed can be employed, where a hydrogenation catalyst (e.g., copper chromite) is loaded in the first part of the reactor, followed by the dehydration/oligomerization catalyst (e.g., H-ZSM-5 zeolite). This dual-catalyst bed may serve to allow conversion of all or most of the ketones to alcohols, thus increasing yields and allowing for production of more desirable hydrocarbons. A dual-catalyst bed can thus be employed where a hydrogenation catalyst is first used that converts all or part of the ketones to alcohols, and is followed by a dehydration/oligomerization catalyst that converts the alcohols and/or ketones to hydrocarbons. Alternatively, a zeolite catalyst can be modified to incorporate hydrogenation catalyst (e.g., platinum) directly in its pores. Employing two different catalysts in the same bed may reduce capital equipment costs and, by combining two reactions into one reactor, may also minimize material losses.

In many cases, the hydrocarbon products exiting the oligomerization reactor contain significant quantities of olefins. In embodiments, these condensed products, which are substantially free of water, are sent to another oligomerization reactor (or recycled to the oligomerization reactor) thereby increasing the chain length of the final hydrocarbon product.

Figure 27:
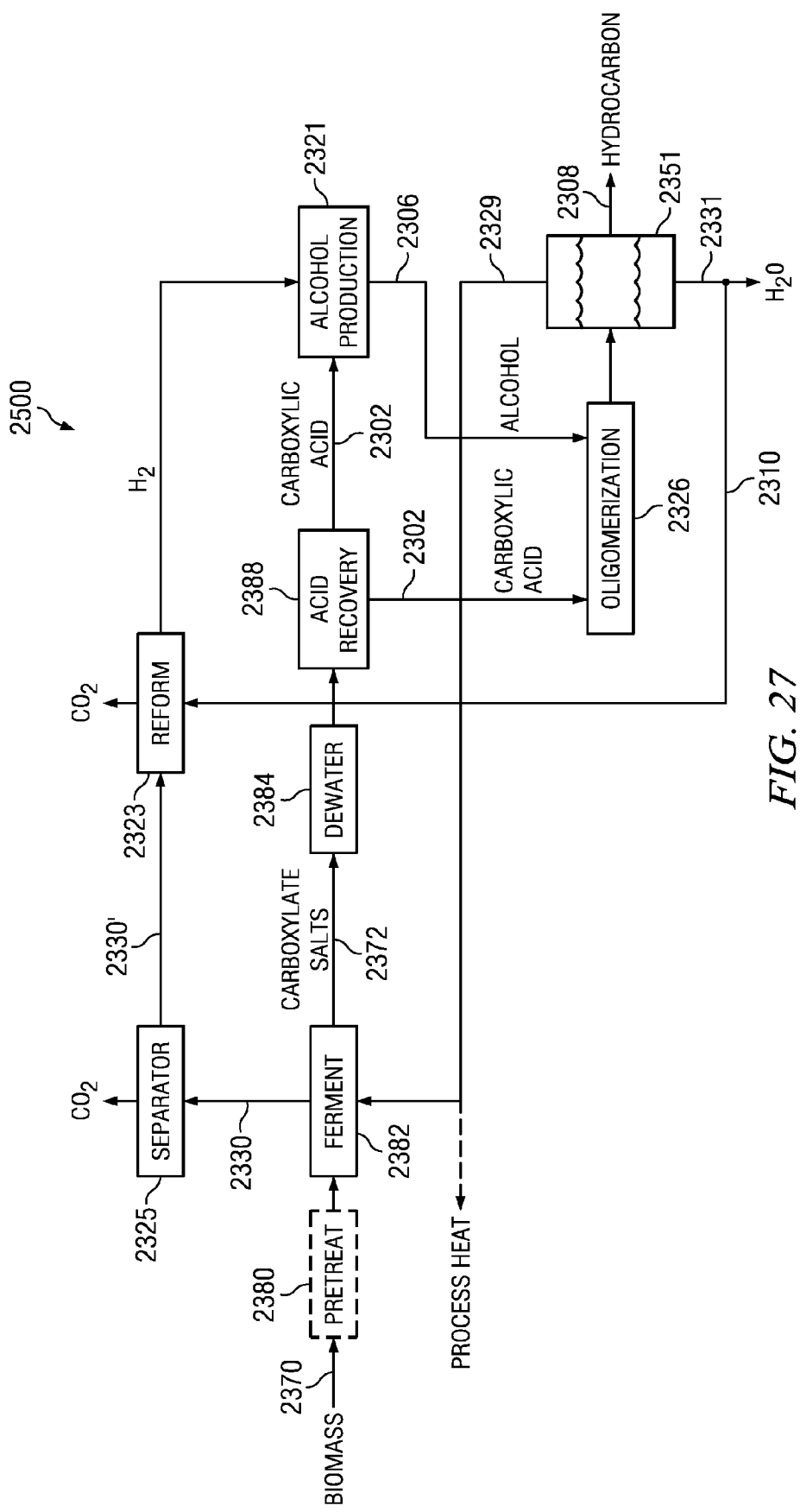
FIG. 27 is a block diagram showing fermentation with direct conversion of carboxylic acids to hydrocarbons, according to an embodiment.

FIG. 27 shows a block diagram of a system 2500 that directly converts carboxylic acids to hydrocarbons, which corresponds to one of the routes shown in FIGS. 1A and 1B, according to one embodiment. This embodiment modifies system 2300 of FIG. 23 by converting carboxylic acids 2302 (instead of ketones) directly into hydrocarbons 2308. The process steps are similar to those described in system 2300, except that the carboxylate salts are converted to carboxylic acids (e.g., via "acid springing," described in, but not limited to, U.S. Pat. No. 6,395,926 or U.S. patent application Ser. No. 11/456,653) using an acid recovery system 2388.

Figure 28:
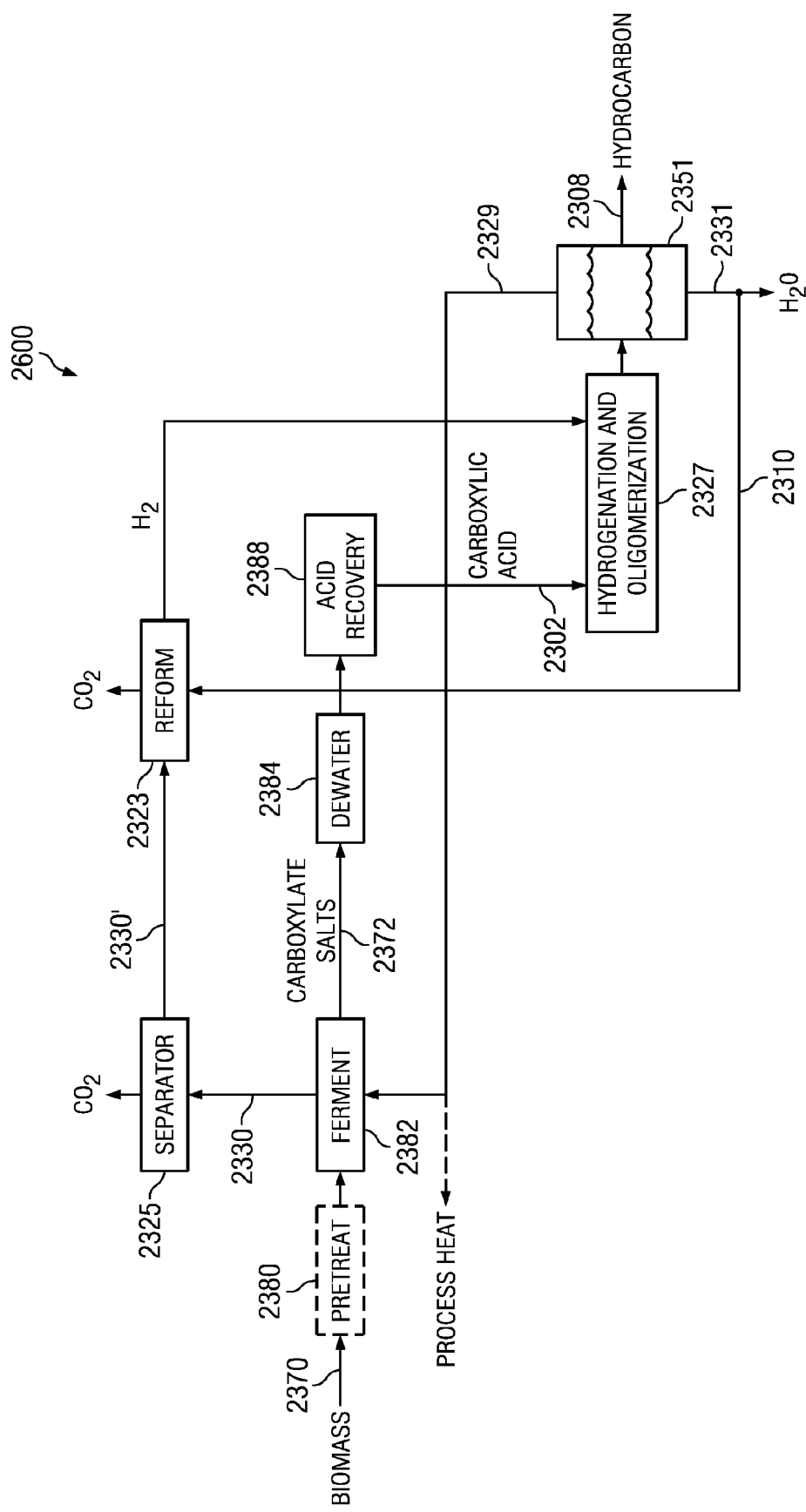
FIG. 28 is a block diagram showing fermentation with direct conversion of carboxylic acids to hydrocarbons with hydrogenation and oligomerization occurring in the same reactor, according to an embodiment.

FIG. 28 shows a block diagram of a system 2600 that directly converts carboxylic acids to hydrocarbons, which corresponds to one of the routes shown in FIGS. 1A and 1B, according to one embodiment. This embodiment modifies system 2500 of FIG. 27 by incorporating the alcohol production (e.g., hydrogenation) and oligomerization mechanisms into a single reactor 2327, with both the carboxylic acids and the hydrogen being fed to this reactor.

Figure 29:
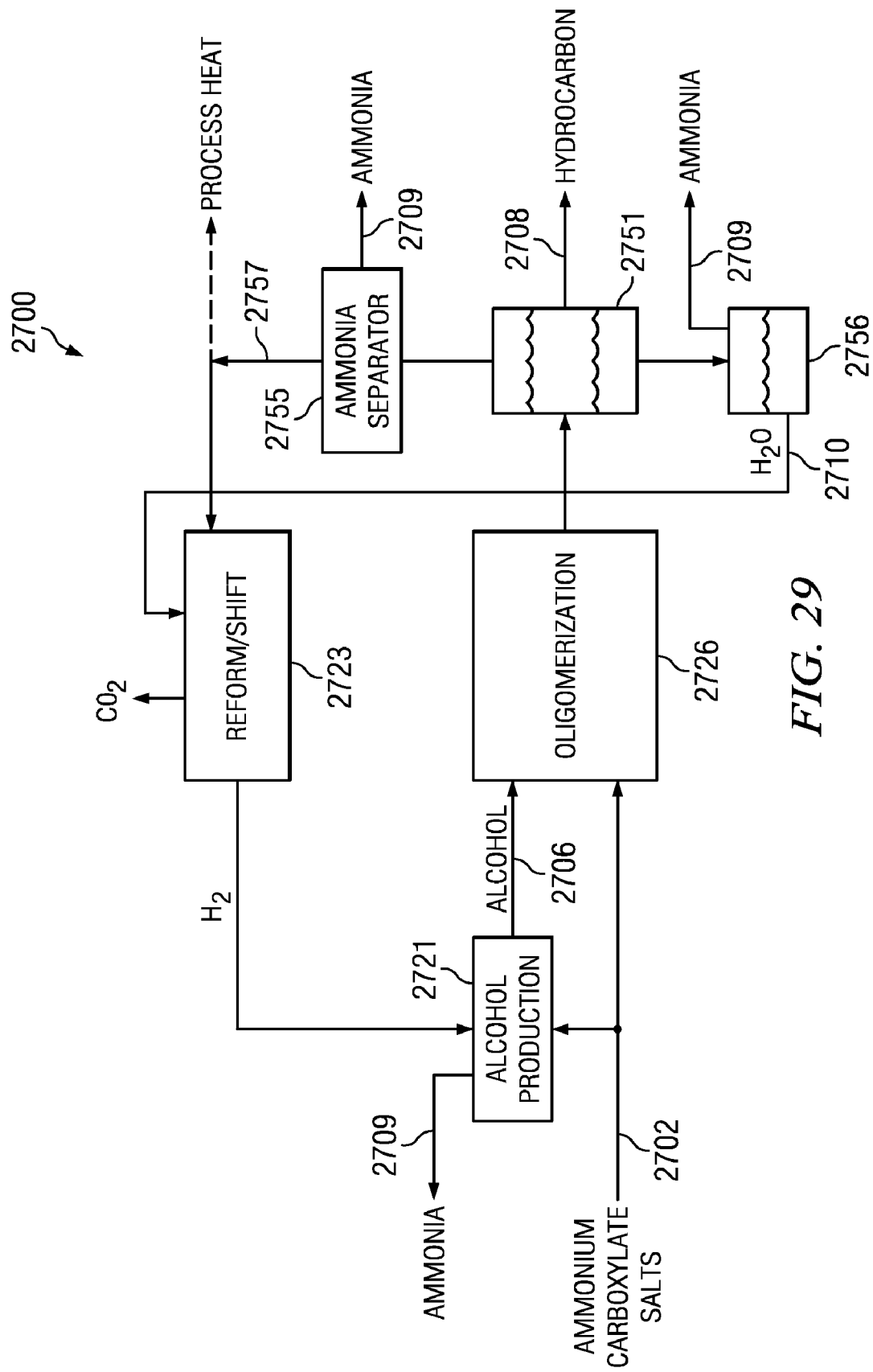
FIG. 29 is a block diagram showing direct conversion of ammonium carboxylate salts to hydrocarbons (Option A1), according to an embodiment.

FIG. 29 shows a block diagram of a system 2700 for direct conversion of ammonium carboxylate salts to hydrocarbons according to an embodiment. The embodiment modifies Option A1 of FIG. 18 by feeding ammonium carboxylate salts 2702 (solids, as a slurry and/or in solution) to the system 2700. Ammonium carboxylate salts 2702 are volatile salts, which when completely vaporized are decomposed into ammonia and carboxylic acids. Some other products, such as amides, might also form. In FIG. 29, a portion of the ammonium carboxylate salts 2702 may be sent to an alcohol reactor 2721, which converts the ammonium carboxylate salts 2702 into alcohols 2706. Teachings of certain embodiments recognize that converting some of the ammonium carboxylate salts 2702 may allow the system 2700 to take advantage of available hydrogen from reformer 2723. Such conversion to alcohols can be done, for example, by using the process described in, but not limited to, U.S. patent application Ser. No. 11/456,653; in another embodiment, they may be converted to carboxylic acids first (e.g., as described in, but not limited to, patent application Ser. No. 11/456,653) and then converted to alcohols (e.g., as described in FIGS. 2-5). The details of the process are similar to those described in FIGS. 3, 5, 7, 9, 11, 13, 15 and 17, which used appropriate sensible and latent heat exchangers to heat and cool the process streams, as well as compressors and expanders to manipulate the pressure. These details are not repeated.

After the ammonium carboxylate salts are vaporized and enter oligomerization reactor 2726, only the carboxylic acid is converted into hydrocarbons 2708. The ammonia 2709 passes unreacted. Such observation was seen by Butter et al. (U.S. Pat. No. 3,894,107), who passed nitrogen-containing compounds through an H-ZSM-5 zeolite catalyst and obtained hydrocarbons and unreacted ammonia as products. Under certain conditions, such as those demonstrated in some of the examples accompanying FIGS. 43-50, ammonia may react to form other valuable compounds, such as acetonitrile.

In system 2700, ammonia 2709 is to be recovered from the products. First, some of the ammonia 2709 will go into solution in the water generated; therefore, a separator 2756 (e.g., a flash tank) may be employed to separate the water 2710 from ammonia 2709. In addition, some ammonia may end up in the gases that exit oligomerization reactor 2726. To remove the ammonia from the gas stream, an ammonia separator 2755 may be employed. For example, a bed packed with solid acid absorbent that will bind the ammonia reversibly, followed by desorption of the ammonia once the bed is saturated (by having two or more of these units operating in parallel, the process can swing from the absorption cycle to the desorption cycle thus continuously removing the ammonia from the stream). The ammonia-free gases 2757 can then be sent to be burned for process heat and/or they may be sent to the reformer 2723 to produce hydrogen, as shown in FIG. 29. The hydrogen produced may be employed in the alcohol reactor 2721. In embodiments, ammonia 2709 is also released and recovered in alcohol production unit 2721.

Figure 30:
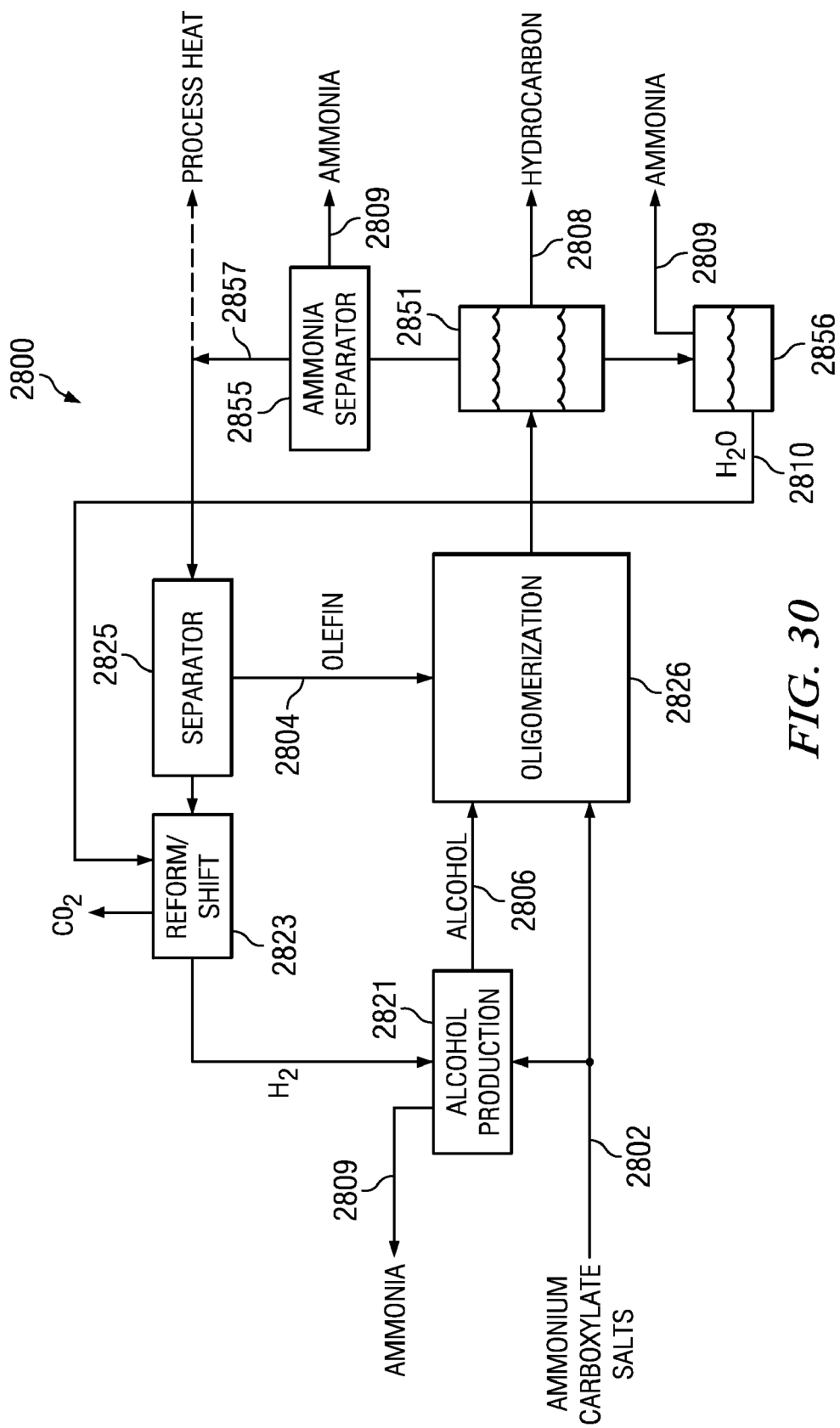
FIG. 30 is a block diagram showing direct conversion of ammonium carboxylate salts to hydrocarbons (Option B1), according to an embodiment.

FIG. 30 shows a block diagram of a system 2800 for converting ammonium carboxylate salts directly to hydrocarbons in the oligomerization reactor. The embodiment modifies Option B1 of FIG. 19 by feeding ammonium carboxylate salts 2802 to the system 2800, as well as incorporates a separator 2825 (e.g., pressure-swing adsorption, membranes, cryogenic distillation) into the system 2700 of FIG. 29 to recover olefins 2804 from the gaseous stream and return them to oligomerization reactor 2826 rather than sending them to reformer 2823.

Figure 31:
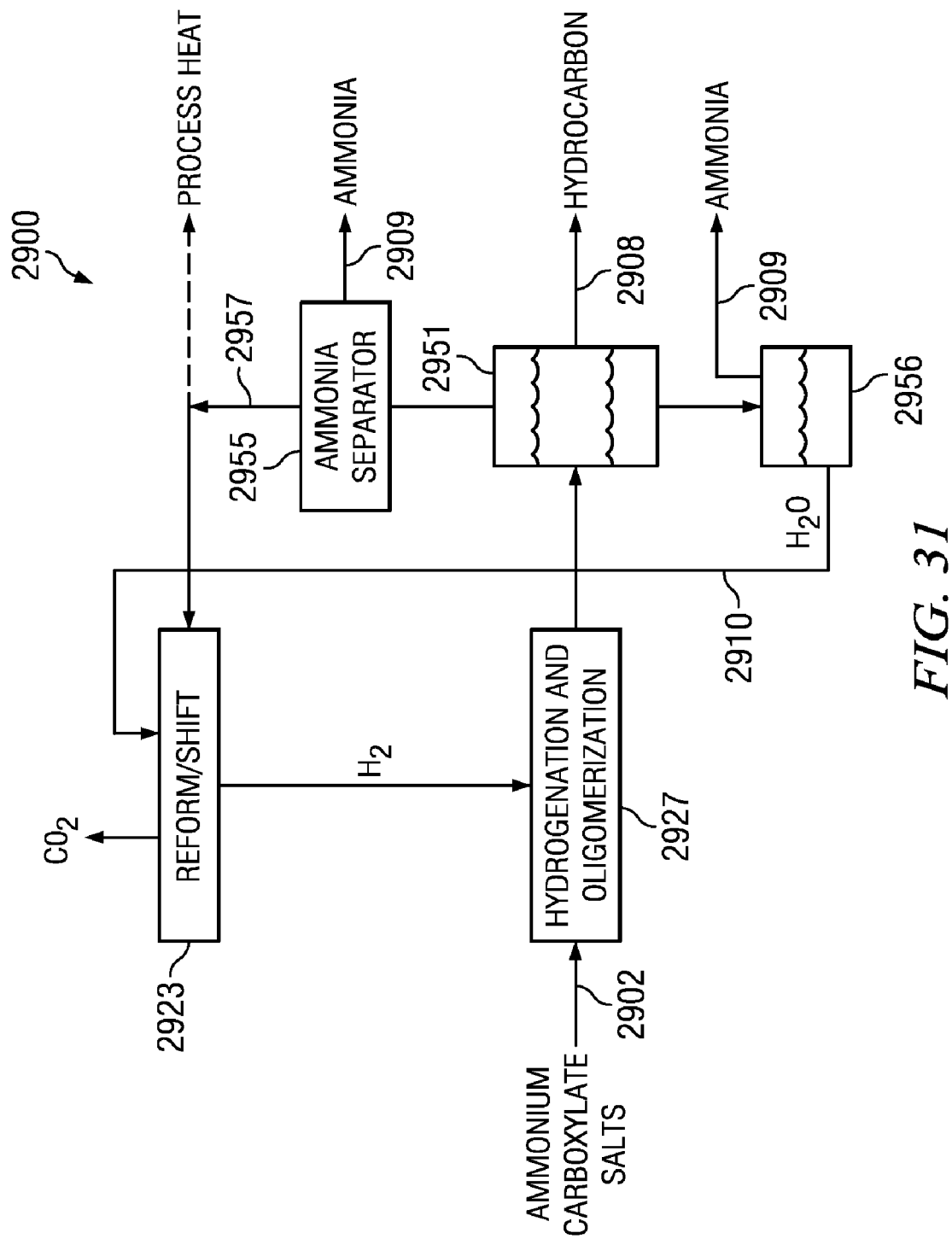
FIG. 31 is a block diagram showing direct conversion of ammonium carboxylate salts to hydrocarbons (Option A2), according to an embodiment.

FIG. 31 shows a block diagram of a system 2900 for converting ammonium carboxylate salts directly to hydrocarbons. The embodiment modifies Option A2 of FIG. 20 by feeding ammonium carboxylate salts 2902 to system 2900, as well as incorporates the oligomerization and hydrogenation processes of system 2700 into a single reactor 2927. Teachings of certain embodiments recognize that, because the same catalysts employed for oligomerization are known to effect hydrogenation as well (e.g., U.S. Pat. No. 3,894,107, Minachev, Kh. M., Garanin, V. I., Kharlamov, V. V., Kapustin, M. A., "Hydrogenation of acetone on cationic forms of zeolites," Russian Chemical Bulletin 23(7), 1472-1475 (1974), ammonium carboxylate salts and hydrogen may be fed directly to the same reactor, thus avoiding the need for a separate hydrogenation reactor and other equipment used for alcohol generation.

Figure 32:
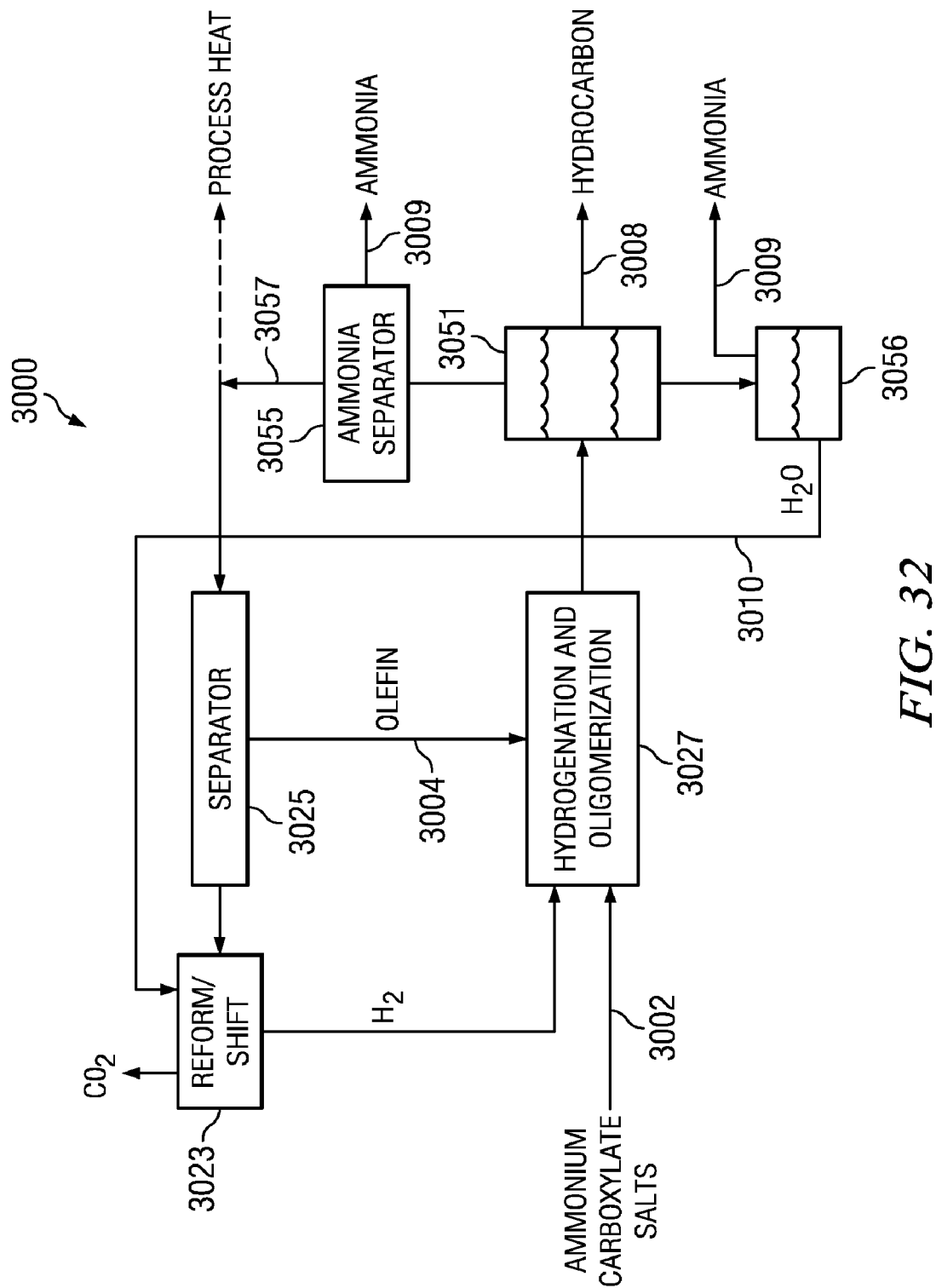
FIG. 32 is a block diagram showing direct conversion of ammonium carboxylate salts to hydrocarbons (Option B2), according to an embodiment.

FIG. 32 shows a block diagram of a system 3000 for converting ammonium carboxylate salts directly to hydrocarbons. The embodiment modifies Option B2 of FIG. 21 by feeding ammonium carboxylate salts 3002 to system 3000, as well as incorporates the oligomerization and hydrogenation processes of system 2800 into a single reactor 3027. Teachings of certain embodiments recognize that, because the same catalysts employed for oligomerization are known to effect hydrogenation as well, the carboxylate salts and hydrogen may be fed directly to the same reactor, thus avoiding the need for a separate hydrogenation reactor and other equipment used for alcohol generation.

Figure 33:
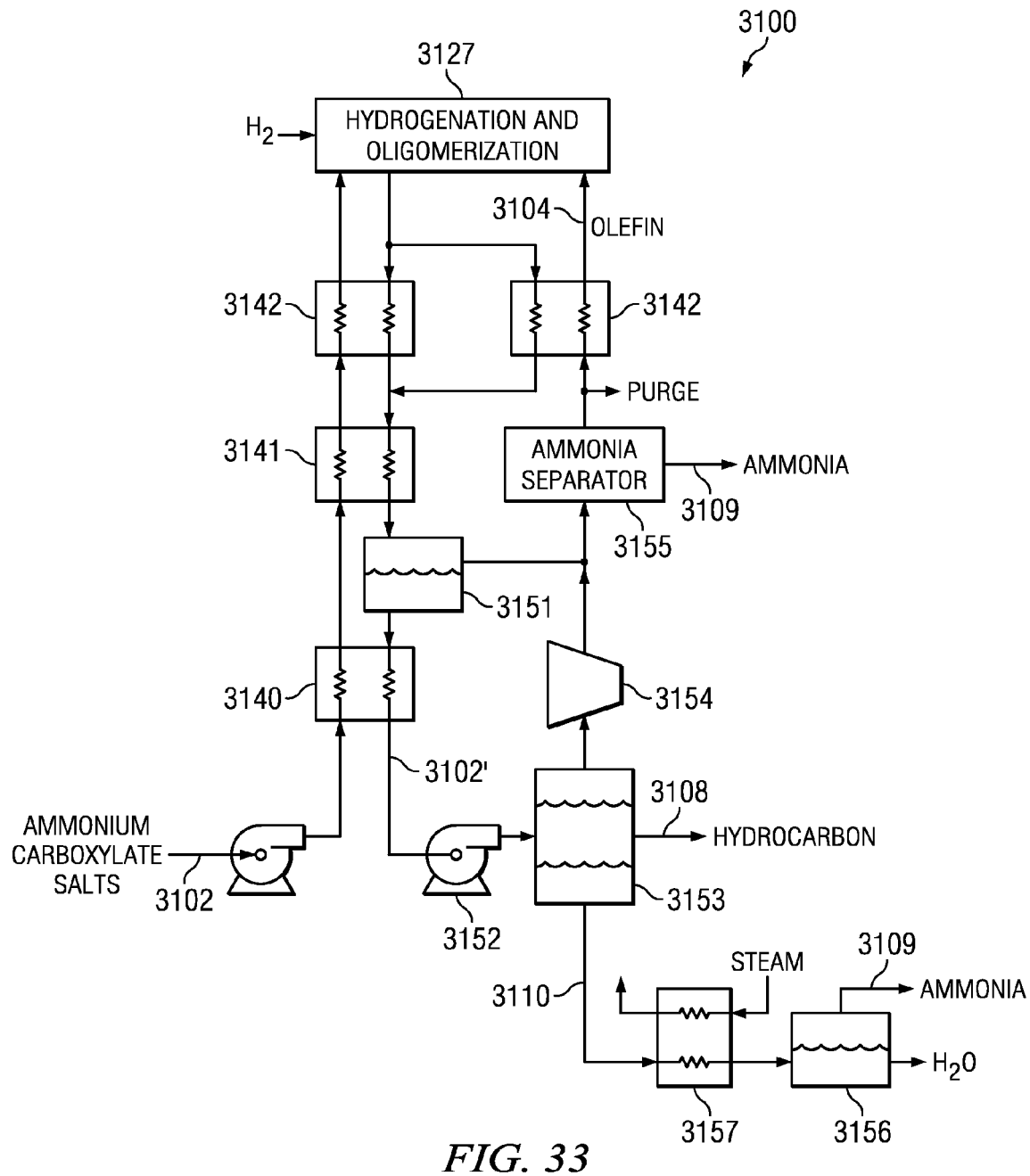
FIG. 33 is a block diagram showing details of a conversion of ammonium carboxylate salts to hydrocarbons (Option A2 and B2), according to an embodiment.

FIG. 33 shows a detailed process flow diagram of a system 3100 for the direct conversion of ammonium carboxylate salts (solid, as a slurry and/or in solution) to hydrocarbons using a single reactor for both hydrogenation and oligomerization (based on Options A2 and B2 illustrated in FIGS. 31 and 32) according to one embodiment. The ammonium carboxylate stream 3102 is sent to sensible heat exchanger 3140, latent heat exchanger 3141, and sensible heat exchanger 3142, such that that the stream 3102 becomes superheated vapor. This superheated stream and hydrogen are sent to hydrogenation/oligomerization reactor 3127. In some embodiments, hydrogenation/oligomerization reactor 3127 has its own temperature control system. The product exiting hydrogenation/oligomerization reactor 3127 is cooled through sensible heat exchanger 3142, latent heat exchanger 3141, and sensible heat exchanger 3140. In some embodiments, this high pressure liquid flows through a turbine 3152 as part of a high-pressure liquid 3102' to recover expansion energy. There may be unreacted species (e.g., low-molecular-weight olefins) in the gas space of tank 3151, which may be then recycled to hydrogenation/oligomerization reactor 3127. Similarly, tank 3153 may contain unreacted species, which may be compressed using compressor 3154 and sent back to hydrogenation/oligomerization reactor 3127.

The recycle stream may contain non-reactive gases, which may be purged to prevent accumulation within the system. The purged gases may be sent to a separator to recover the reactive components, or they may be burned for process heat or reformed into hydrogen. Hydrogenation/oligomerization reactor 3127 can operate at a higher pressure (~3000 kPa), according to certain embodiments.

Before the gas stream from tanks 3151 and 3153 is returned to hydrogenation/oligomerization reactor 3127, or before some of it is purged, ammonia 3109 may be removed therefrom by passing it through an ammonia separator 3155. For example, a bed packed with solid acid absorbent that will reversibly bind the ammonia may be employed, followed by desorption of the ammonia once the bed is saturated; in some embodiments, by having two or more of these units operating in parallel, the process can swing from the absorption cycle to the desorption cycle, thus continuously removing the ammonia from the stream. In addition, the water 3110 that is separated from the hydrocarbon 3108 and gas stream in tank 3153 may contain some ammonia, which is separated from the water, for example, by increasing its temperature using steam in sensible heat exchanger 3157 and then sending the stream to tank 3156 (e.g., flash tank), allowing ammonia 3109 to be recovered in the vapor phase, while ammonia-free water is recovered in the liquid phase. Alternatively, a steam stripper can also be used to strip the ammonia from the water.

Figure 34:
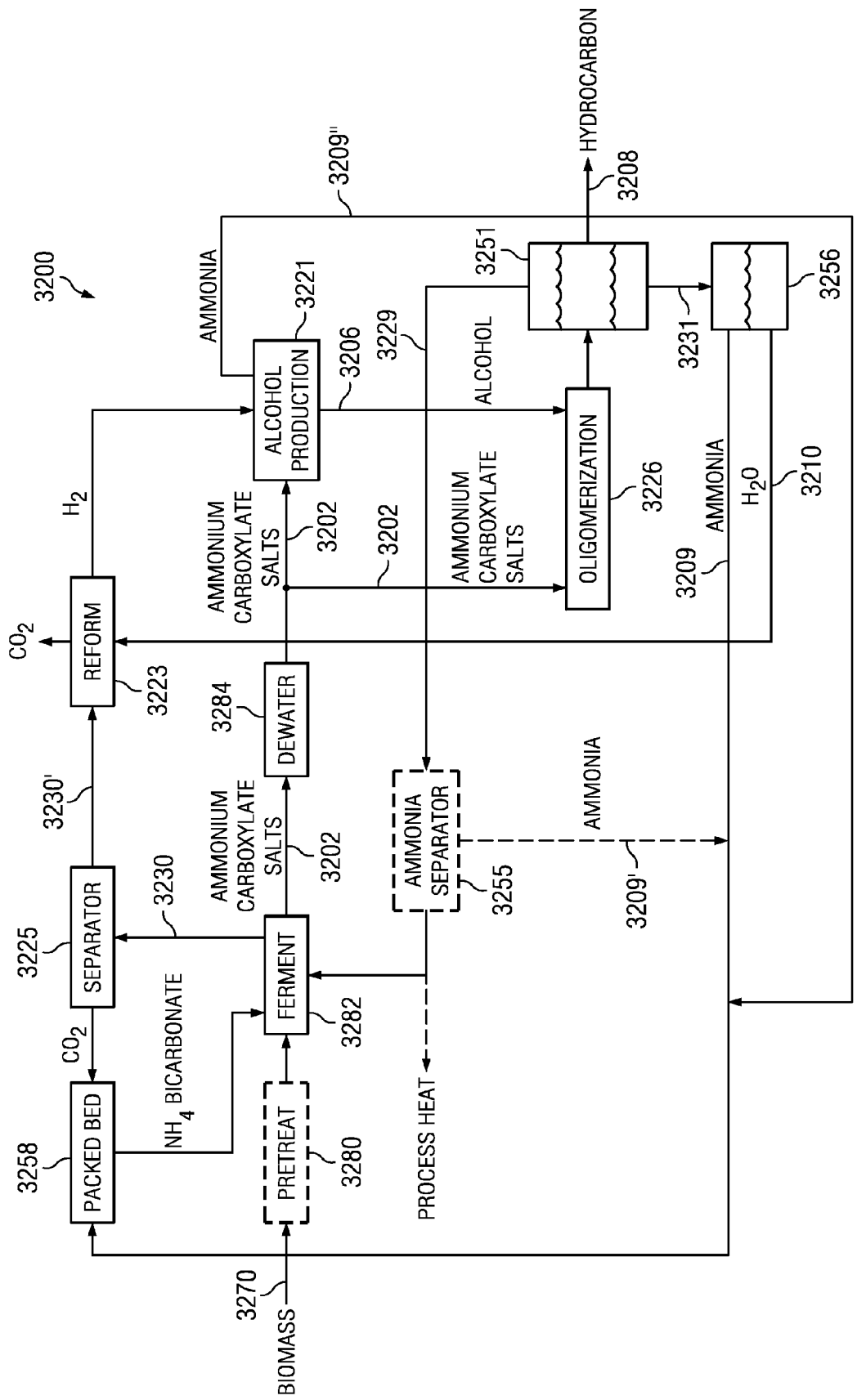
FIG. 34 is a block diagram showing fermentation with direct conversion of ammonium carboxylate salts to hydrocarbons, according to an embodiment.

FIG. 34 shows a block diagram of an embodiment of a system 3200 for a process that directly converts ammonium carboxylate salts to hydrocarbons, which corresponds to one of the routes shown in FIG. 1B. In the illustrated embodiment, the biomass 3270 is optionally pretreated at 3280 to enhance biodegradability (e.g., using, but not limited to, lime pretreatment described in, but not limited to, U.S. Pat. Nos. 5,693,296 and 5,865,898, and U.S. Pat. App. Nos. 60/423,288 and 60/985,059). Subsequently, the pretreated biomass 3270 is directly fermented at 3282 to ammonium carboxylate salts 3202 (e.g., as described in, but not limited to, U.S. patent application Ser. Nos. 11/298,983 and 11/456,653). The resulting ammonium carboxylate salts 3202 are dewatered at a dewatering unit 3284. As a result, the carboxylate salts 3202 are concentrated (e.g., using processes or systems described in, but not limited to, U.S. Pat. Nos. 5,986,133, 7,251,944, and 7,328,591 and U.S. Pat. App. No. 60/985,059). The ammonium carboxylate salts 3202 may be directly converted to hydrocarbons 3208 and alcohols 3206, in a manner similar to the processes described in FIGS. 29-33. However, in this embodiment, the gases 3229 exiting oligomerization reactor 3226 are directed to the fermenter 3282, after separation from hydrocarbons 3208 and water 3231 in tank 3251. In fermenter 3282, biologically reactive species (e.g., hydrogen and carbon monoxide) and buffering species (e.g., the ammonia) are converted to ammonium carboxylate salts 3202. Energetic gases 3230' (e.g., hydrogen and/or methane) exiting fermenter 3282 are separated from carbon dioxide in fermenter exit gas 3230 using standard methods (e.g., amine adsorption, membranes, cryogenics). Energetic gases 3230' are sent to a reformer 3223 to produce hydrogen for alcohol producer 3221. Ammonia 3209 recovered from the water exiting the oligomerization reaction 3226 (e.g., using a tank 3256) and from alcohol producer 3221 is sent back to the fermenter 3282, via a packed bed 3258 wherein it is contacted with carbon dioxide from separator 3225. This produces ammonium bicarbonate, which allows easier pH control in fermenter 3282. Shown in dotted lines, it might be desired to remove the ammonia present in the gas stream 3229 that is generated from the oligomerization reactor 3226 (e.g., to allow better pH control in the fermentation); thus, an ammonia separator 3255 (e.g., beds packed with a solid acid absorbent) may be employed. The ammonia 3209' recovered from this gas joins the ammonia 3209 from the water 3231 that exits oligomerization reactor 3255 and the ammonia 3209" from alcohol reactor 3221 and is sent to packed bed 3258' to be converted into ammonium bicarbonate to control the pH in the fermentation. Water 3210 that exits oligomerization reactor 3226 may be used in reformer 3223 after ammonia 3209 has been removed therefrom.

Figure 35:
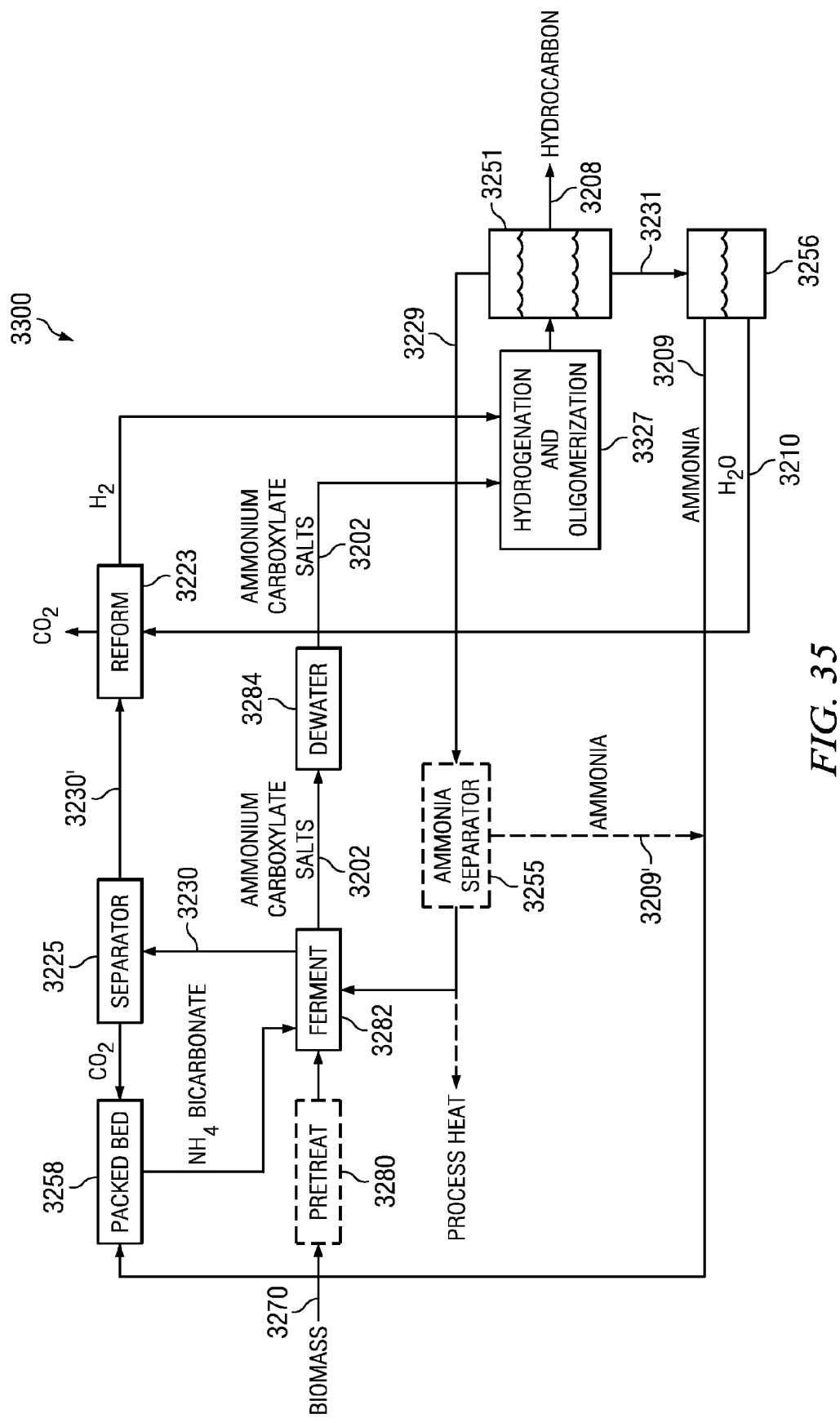
FIG. 35 is a block diagram showing fermentation with direct conversion of ammonium carboxylate salts to hydrocarbons with hydrogenation and oligomerization occurring in the same reactor, according to an embodiment.
Figure 36:
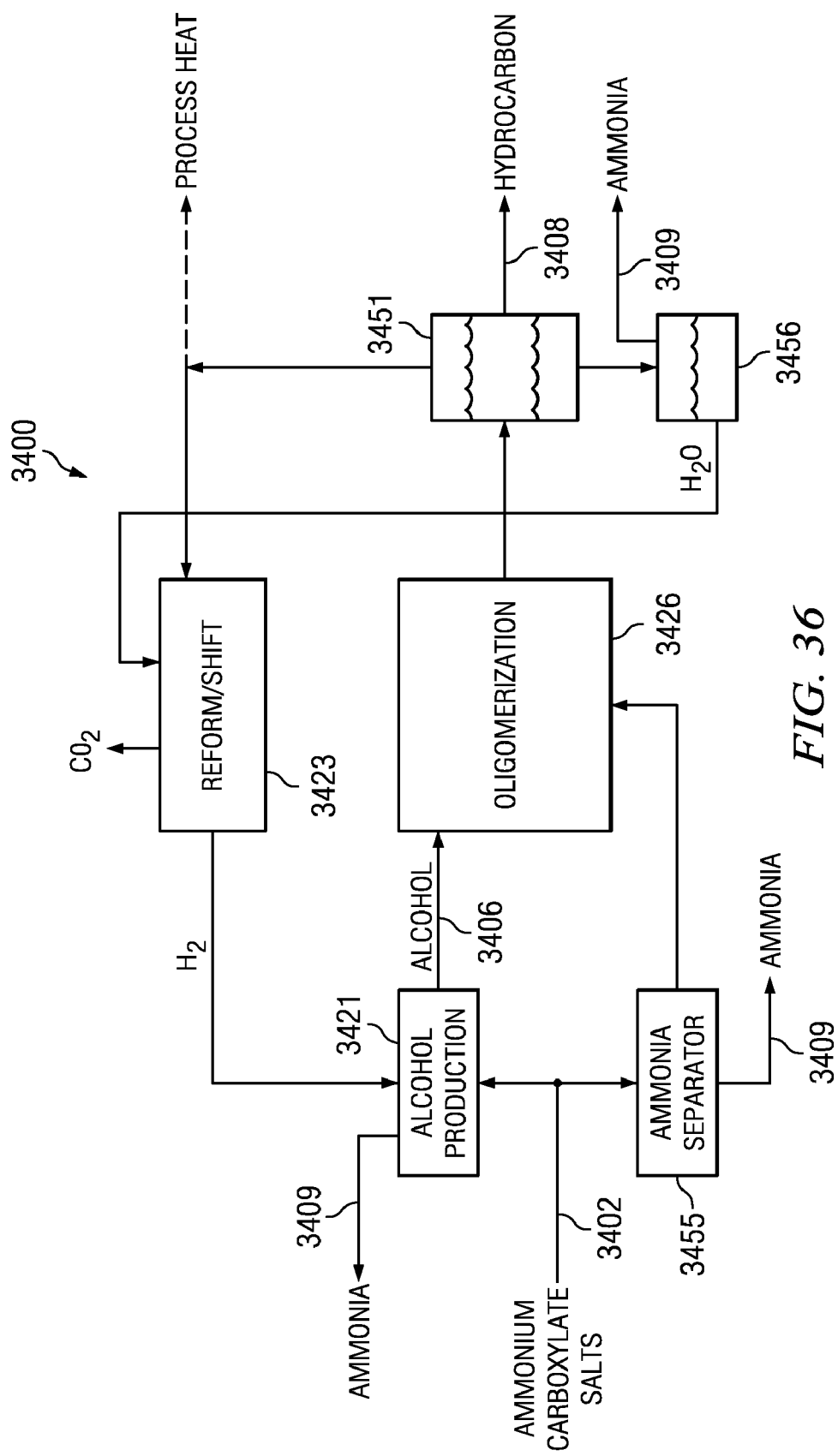
FIG. 36 is a block diagram showing direct conversion of ammonium carboxylate salts to hydrocarbons with prior removal of ammonia (Option A1), according to an embodiment.
Figure 37:
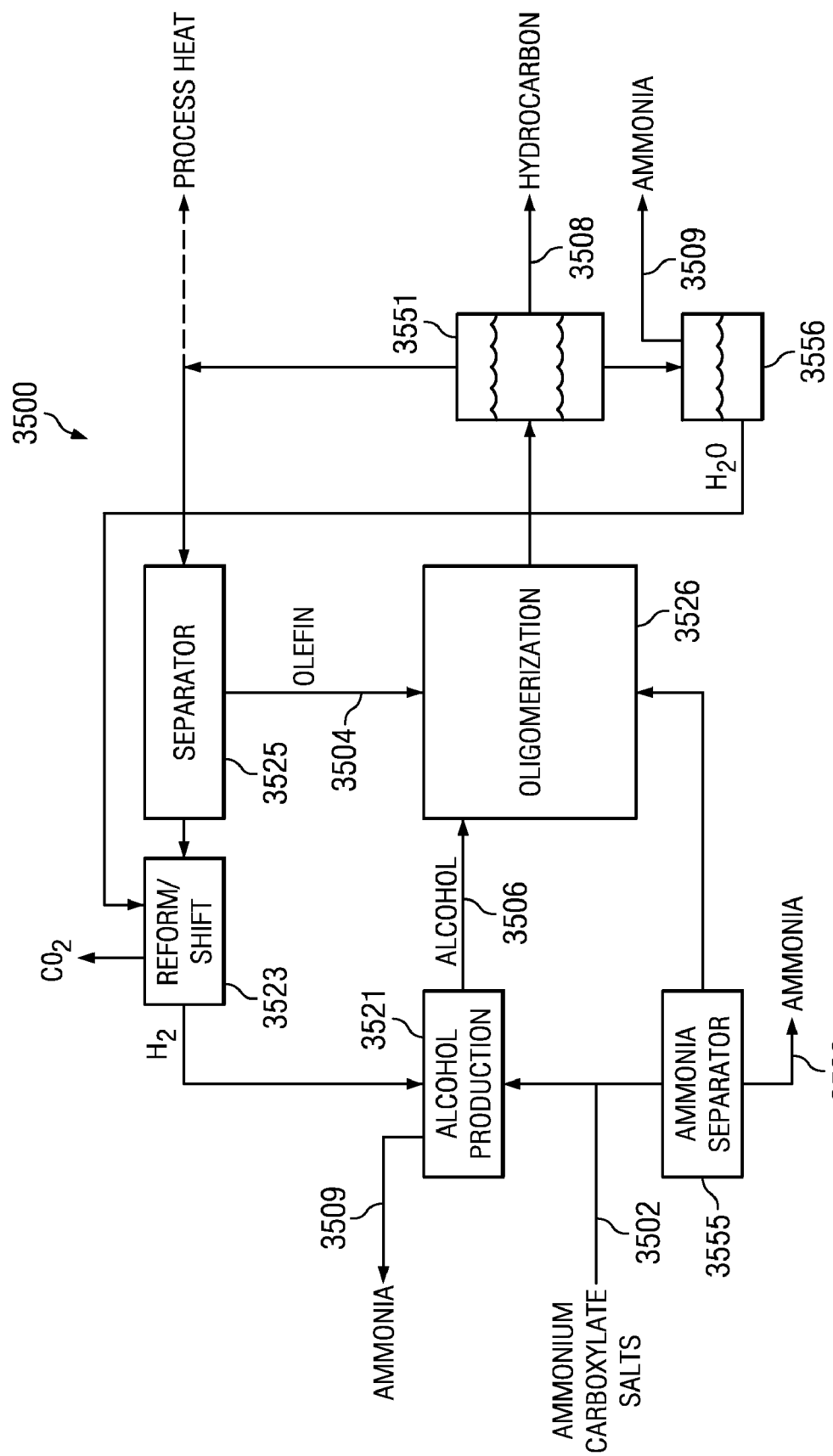
FIG. 37 is a block diagram showing direct conversion of ammonium carboxylate salts to hydrocarbons with prior removal of ammonia (Option B1), according to an embodiment.
Figure 38:
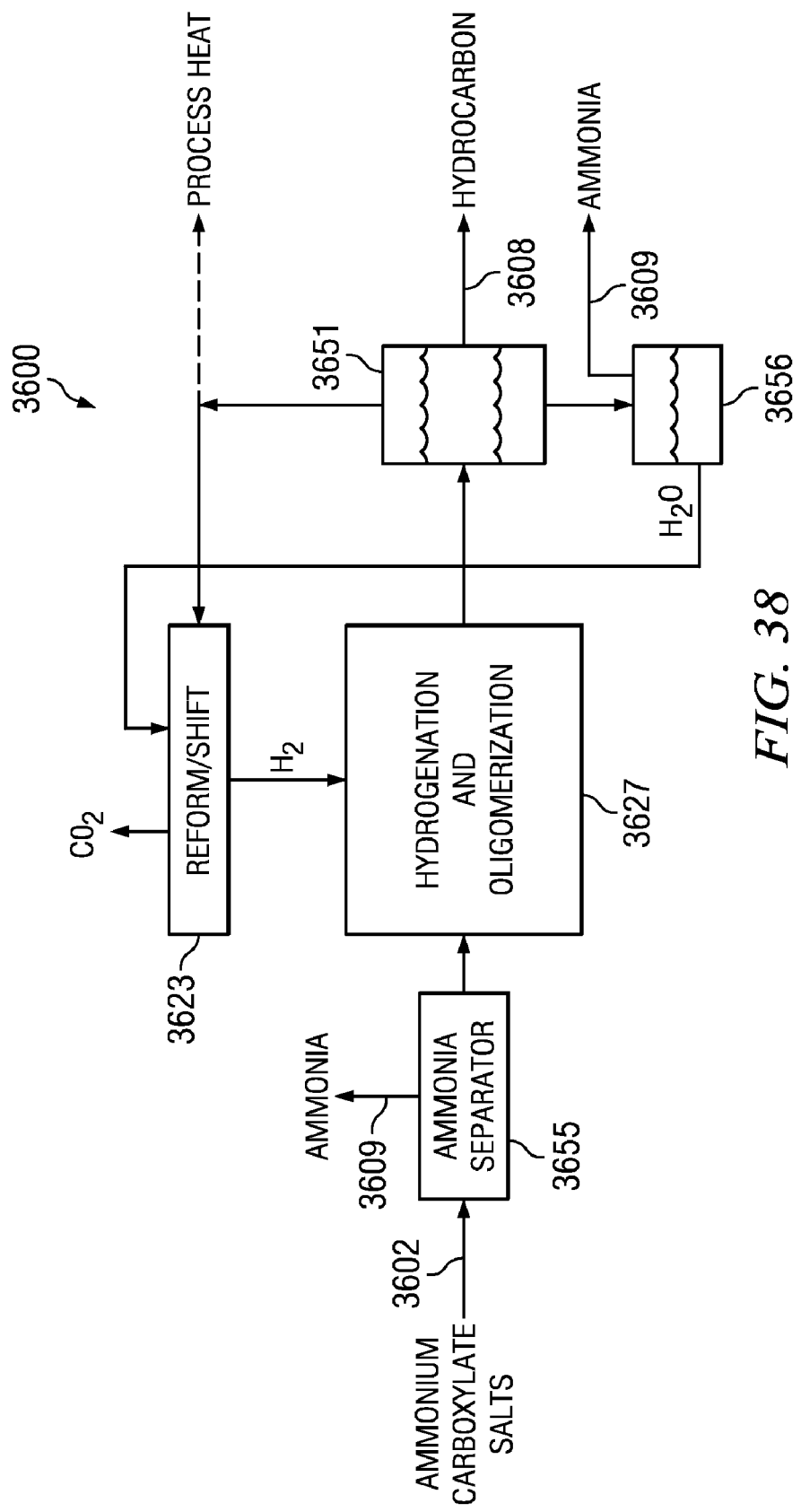
FIG. 38 is a block diagram showing direct conversion of ammonium carboxylate salts to hydrocarbons with prior removal of ammonia (Option A2), according to an embodiment.
Figure 39:
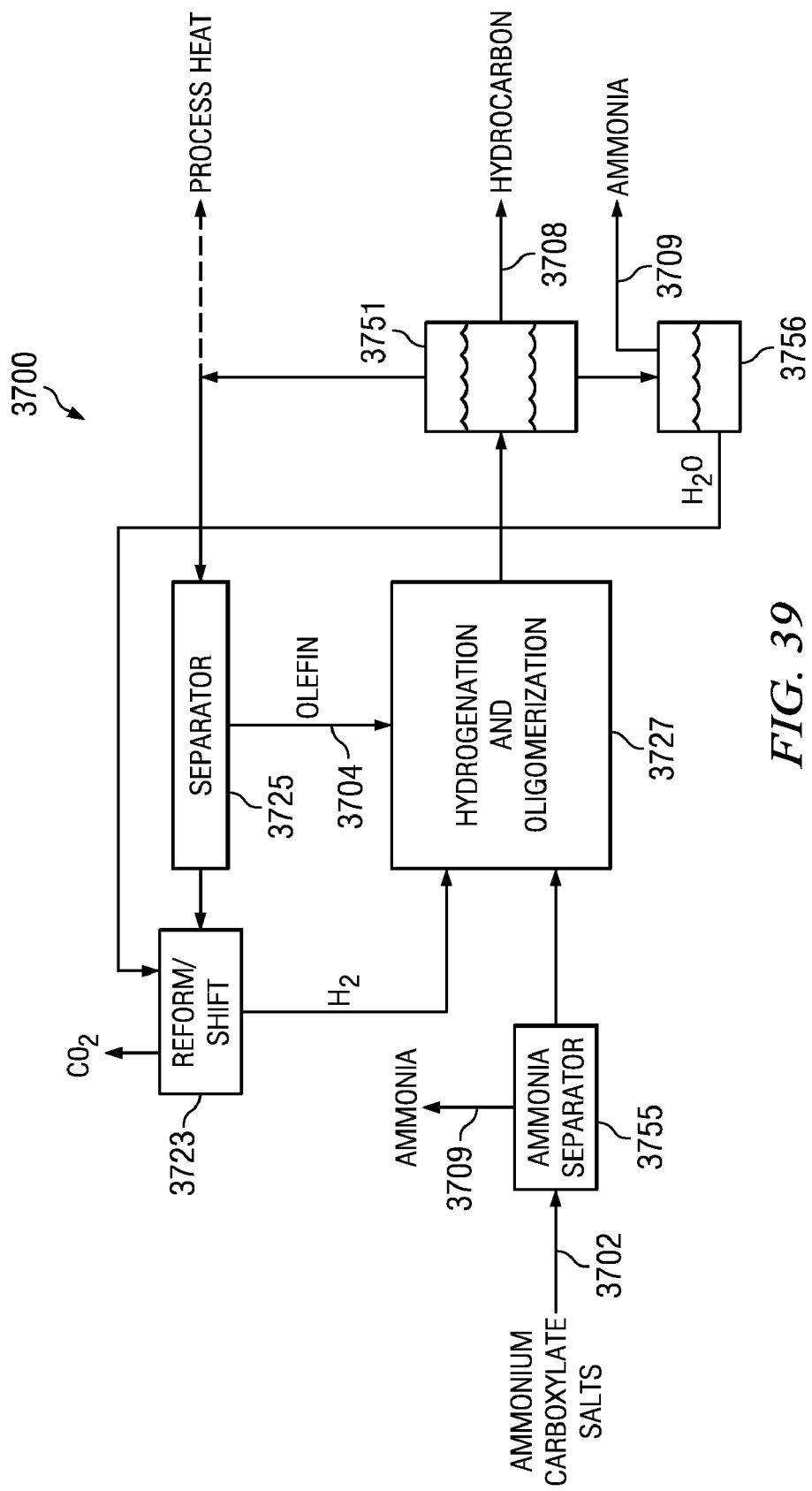
FIG. 39 is a block diagram showing direct conversion of ammonium carboxylate salts to hydrocarbons with prior removal of ammonia (Option B2), according to an embodiment.
Figure 40:
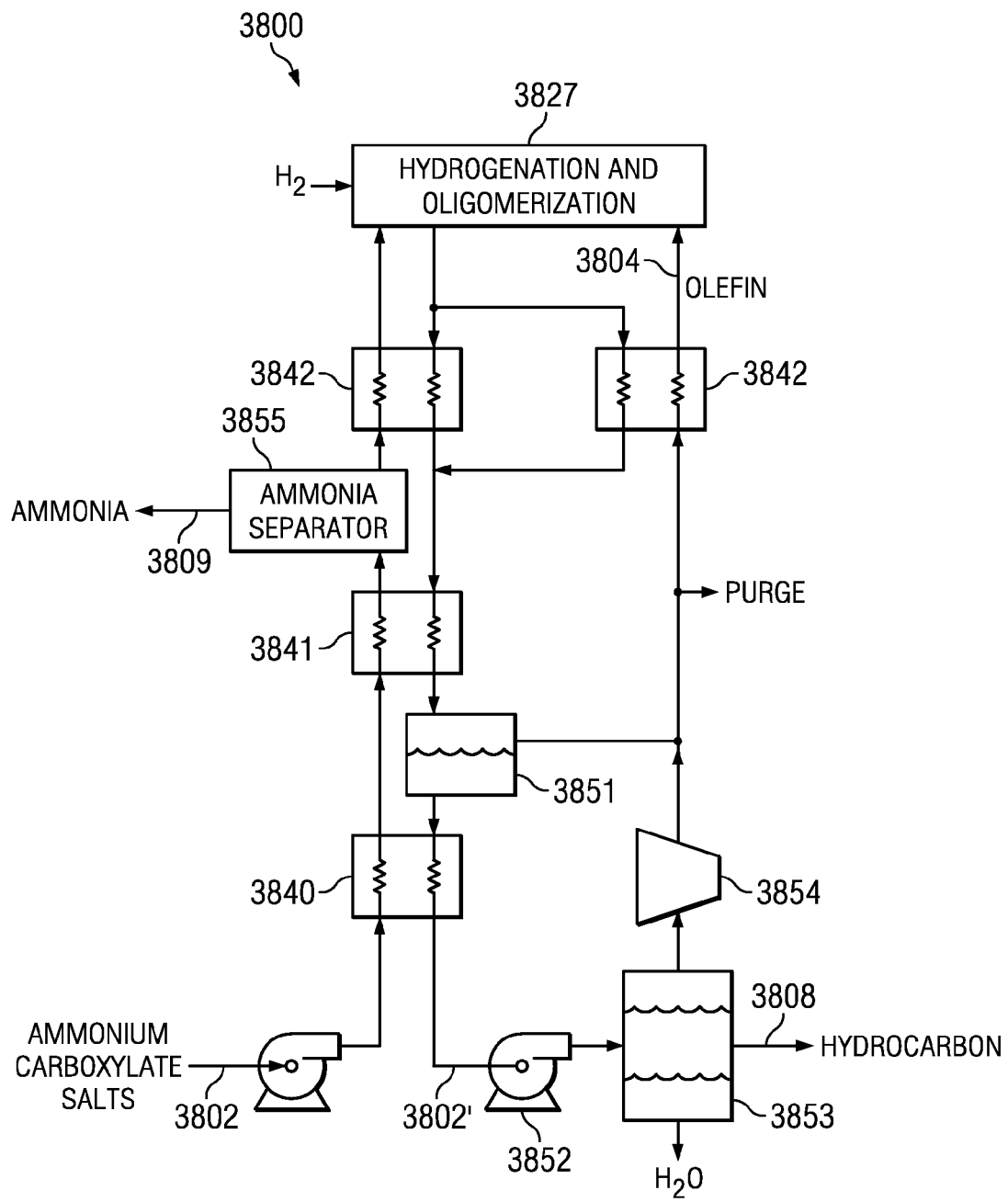
FIG. 40 is a block diagram showing details of a conversion of ammonium carboxylate salts to hydrocarbons with prior removal of ammonia (Option A2 and B2), according to an embodiment.
Figure 41:
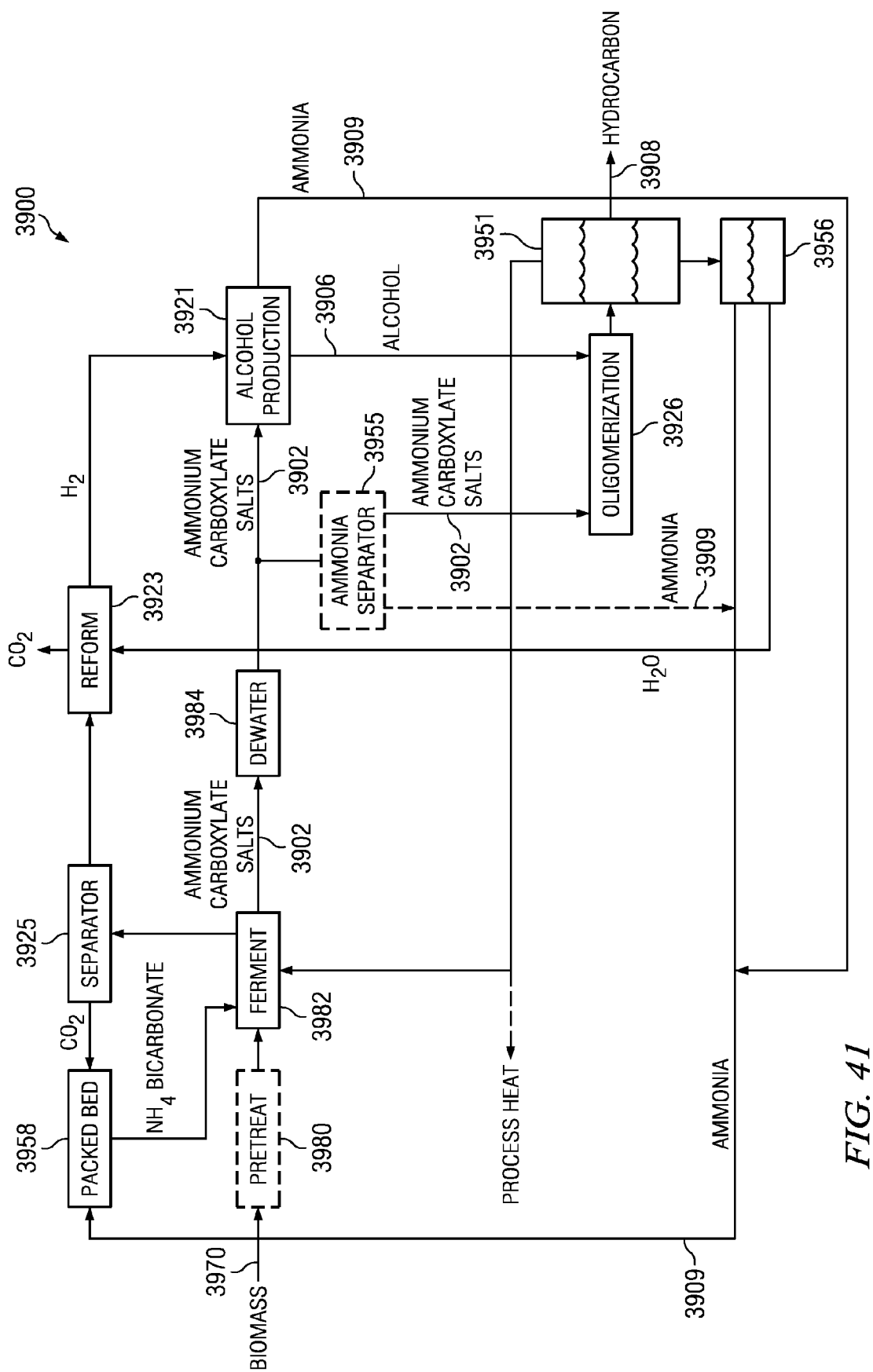
FIG. 41 is block diagram showing fermentation with direct conversion of ammonium carboxylate salts to hydrocarbons with ammonia removal prior to oligomerization, according to an embodiment.
Figure 42:
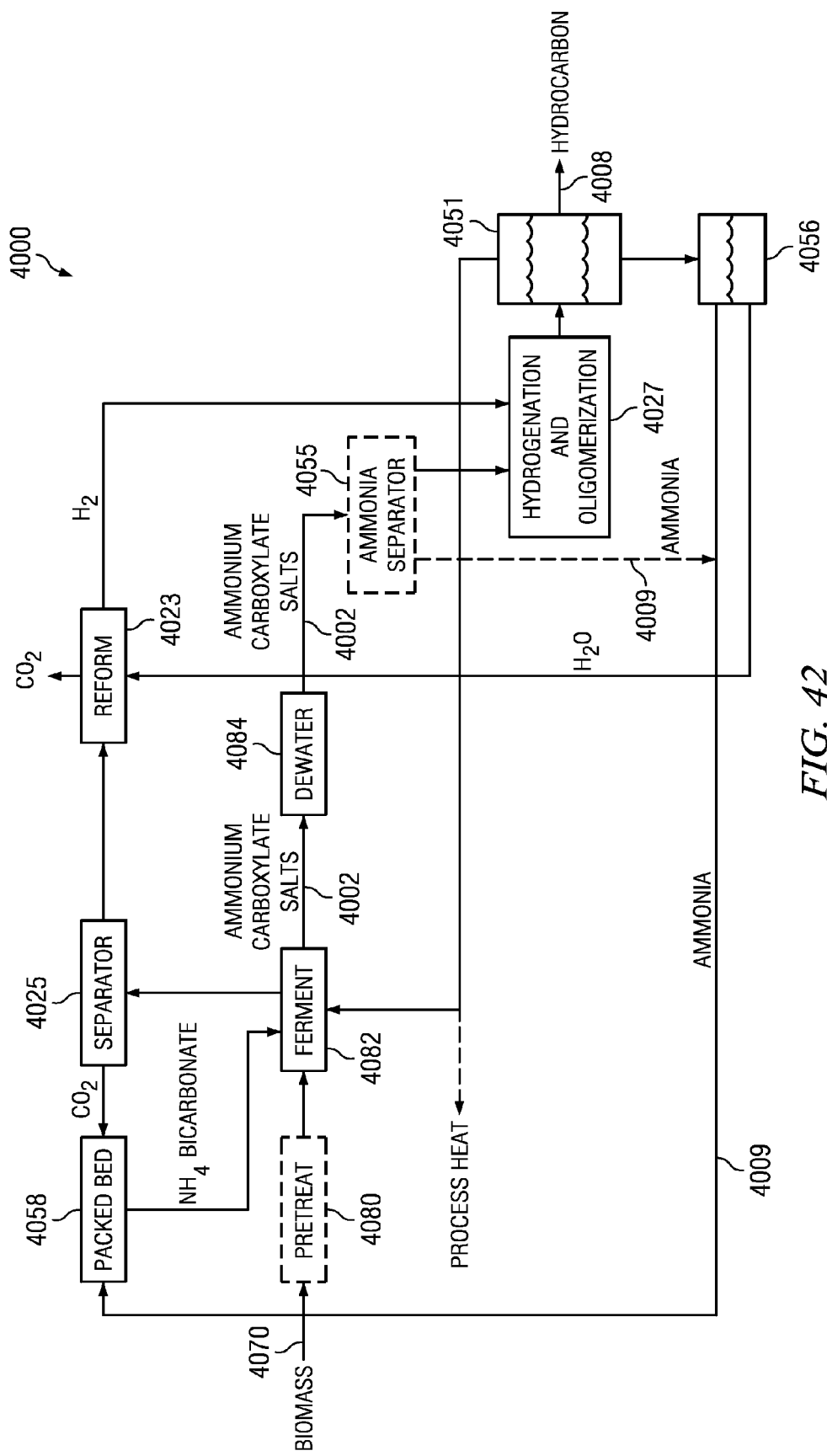
FIG. 42 is a block diagram showing fermentation with direct conversion of ammonium carboxylate salts to hydrocarbons with hydrogenation and oligomerization occurring in the same reactor with removal of ammonia prior to the oligomerization, according to an embodiment.

FIG. 35 shows a system 3300 that directly converts ammonium carboxylate salts to hydrocarbons, which corresponds to one of the routes shown in FIG. 1B, according to one embodiment. This embodiment modifies system 3200 by incorporating the alcohol production (e.g., hydrogenation) and oligomerization mechanisms into a single reactor 3327, with both the ammonium carboxylate salts and the hydrogen being fed to this reactor.

FIGS. 36 through 42 show systems 3400-4000 for direct conversion of ammonium carboxylate salts to hydrocarbons according to several embodiments. Systems 3400-4000 modify the systems 2700-3300 of FIGS. 29-35 by removing and recovering the ammonia from the ammonium carboxylate stream prior to entering the oligomerization unit. To remove the ammonia from the gas stream, an ammonia separator 3455/3555/3655/3755/3855/3955/4055 may be employed. For example, a bed packed with solid-acid absorbent may be used to bind the ammonia reversibly. Then, once the bed is saturated, the ammonia is desorbed. In some embodiments, by having two or more of these units operating in parallel, the process can swing from the absorption to the desorption cycle, thus continuously removing the ammonia from the stream.

Esterification, hydrogenolysis, and oligomerization reactions are exothermic; therefore, it is possible that some trim cooling might be utilized in some or all of the above configurations. In all cases, in a given reactor, it is possible that the reaction will be incomplete or that byproducts will be produced. In these cases, unreacted reactant or byproducts can be separated and further processed.

Features. Certain embodiments may include, some, none, or all of the following features. The reaction of an olefin with a carboxylic acid to form an ester is irreversible, so the reaction goes to high conversions easily. In contrast, the reaction of a carboxylic acid with an alcohol to form an ester (the more standard technology) is reversible. It requires that the ester products be removed during the reaction to drive the reaction to completion, which is difficult.

The alcohol dehydration reaction is reversible, but it is made more favorable by operating at low pressures. Pressure reduction is accomplished with an expander, which recovers energy for use during the recompression of the gases exiting the dehydration reactor.

The capability of the esterification catalyst to also hydrogenolyze the esters formed from the reaction of the olefin and carboxylic acids avoids expenditures for the implementation of a separate unit for hydrogenolysis, as the carboxylic acids, the olefin and the hydrogen may be fed directly into the same reactor to produce alcohols.

The direct conversion of ketones or carboxylic acids or ammonium carboxylate salts to hydrocarbons (FIGS. 18-24 and 27-35) reduces hydrogen requirements compared to the conversion of ketones, carboxylic acids or ammonium carboxylate salts to alcohols first and then to hydrocarbons (FIGS. 6-17). Combining both of these steps together (direct ketone/carboxylic acid/ammonium carboxylate conversion plus alcohol conversion) allows the process to be "tuned" to match the availability of hydrogen. If hydrogen is readily available, then the alcohol route is favored. If hydrogen is scarce, then the direct ketone/carboxylic acid/ammonium carboxylate route is favored.

The capability of oligomerization catalysts to also hydrogenate the feed avoids expenditures for the implementation of a separate unit for producing alcohols, as the ketones, carboxylic acids and/or the ammonium carboxylate salts may be fed directly with the available hydrogen into the same reactor to produce hydrocarbons.

The processes that integrate with the fermentation (FIGS. 24 and 27-28 and FIGS. 34-35) reduce loads on separators and reformers because biologically reactive gases and ammonia are converted to carboxylate salts and do not have to be separated prior to being sent to the reformer or converted to hydrogen in the reformer.

EXAMPLES

The following section provides further details regarding examples of various embodiments.

Example 1

Isopropanol to Hydrocarbons (Si/Al 30)

Materials and Methods: Liquid isopropanol was vaporized and added to the reactor operated using the conditions shown in Table 1.1. The product exiting the reactor was separated into two fractions: liquid and gas. The total mass of each product was measured and the composition was determined by gas chromatography/mass spectroscopy (GC/MS).

Results: Table 1.2 shows the product distribution. Of the total product, the liquid fraction (gasoline) was 68.89% and the gases were 31.13%. Table 1.3 shows the classes of products in the liquid fraction.

TABLE 1.1

Example 1 Reaction Conditions-
Isopropanol-to-Hydrocarbon Reactor

| | |
|---|---|
| Isopropanol Flow Rate | 10 mL liquid/h |
| Catalyst Mass | 6 g |
| Weight Hourly Space Velocity (WHSV) | 1.31 g reactant/(g catalyst · h) |
| Temperature (Max.) | 325° C. |
| Pressure | 1 atm (abs) |
| Catalyst | H-ZSM-5 (Si/Al 30) |

TABLE 1.2

Product Distribution (wt %)

| Gas | | Liquid | |
|---|---|---|---|
| $CH_4$ | 0.00% | C5s | 13.45% |
| $CO_2$ | 0.03% | C6s | 11.28% |
| $C_2H_4$ | 0.52% | C7s | 8.99% |
| $C_2H_6$ | 0.03% | C8s | 18.43% |
| $C_3H_6$ | 1.10% | C9s | 10.64% |
| $C_3H_8$ | 7.13% | C10s | 3.95% |
| CO | 0.00% | C11+ | 2.13% |
| C4s | 22.33% | Total | 68.87% |
| Total | 31.13% | | |

TABLE 1.3

Hydrocarbon Distribution
in the Liquid (Gasoline) Fraction (wt %)

| Paraffins | Olefins | Isomeric Compounds | Naphthenes | Naphthene Olefinics | Aromatics |
|---|---|---|---|---|---|
| 4.502 | 4.601 | 17.872 | 27.679 | 3.91 | 39.234 |

Example 2

Isopropanol to Hydrocarbons (Si/Al 280)

Materials and Methods: Liquid isopropanol was vaporized and added to the reactor operated using the conditions shown in Table 2.1. The product exiting the reactor was separated into two fractions: liquid and gas. The total mass of each product was measured and the composition was determined by gas chromatography/mass spectroscopy (GC/MS).

Figure 43:
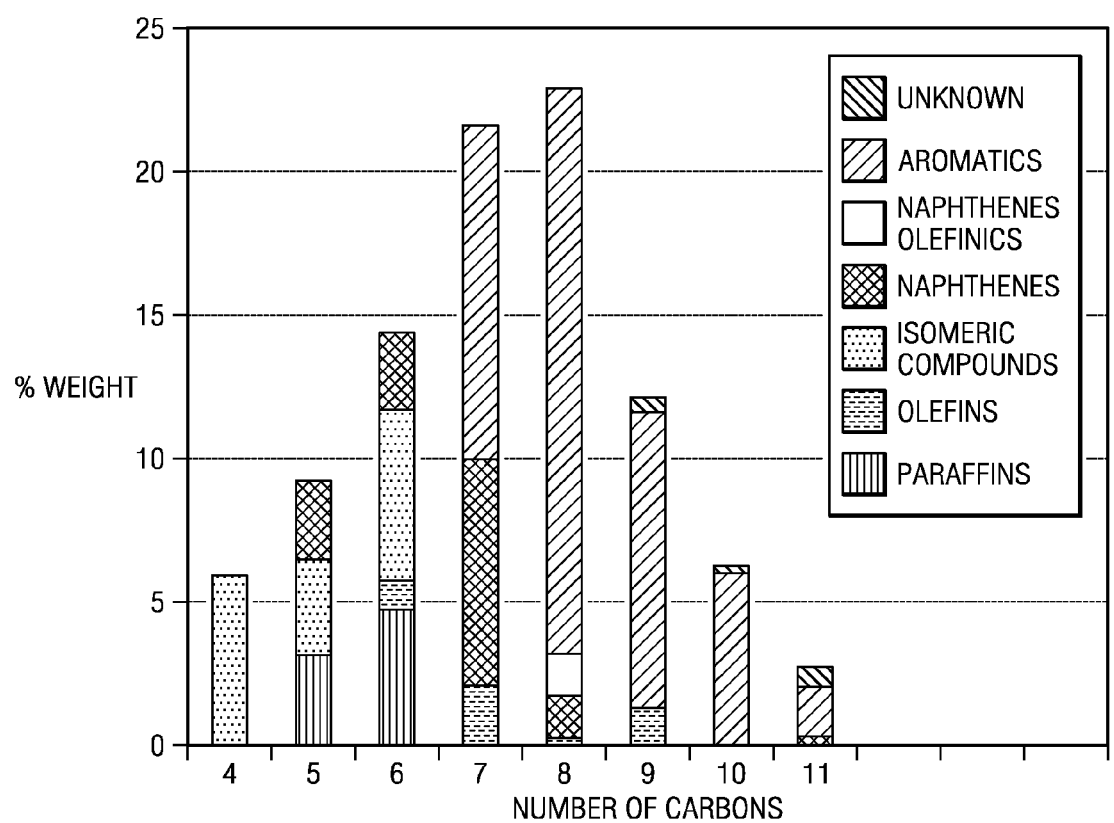
FIG. 43 illustrates the liquid-phase product distribution as a function of hydrocarbon type and number of carbons for isopropanol oligomerization over H-ZSM-5 zeolite (Si/Al ratio 280), according to one example embodiment.

Results: Table 2.2 shows the product distribution. Of the total product, the liquid fraction (gasoline) was 63.23% and the gases were 36.77%. Table 2.3 shows the classes of products in the liquid fraction. Tables 1.3 and 2.3 report identical conditions, except for the catalyst (H-ZSM-5 Si/Al 280 versus Si/Al 30). The product distribution is similar; however, Si/Al 280 has less coking and more paraffins in the product, which is important for a good fuel. FIG. 43 illustrates the liquid-phase product distribution as a function of hydrocarbon type and number of carbons for isopropanol oligomerization over H-ZSM-5 zeolite (Si/Al ratio 280).

TABLE 2.1

Example 2 Reaction Conditions-
Isopropanol-to-Hydrocarbon Reactor

| | |
|---|---|
| Isopropanol Flow Rate | 10 mL liquid/h |
| Catalyst Mass | 6 g |
| Weight Hourly Space Velocity (WHSV) | 1.31 g reactant/(g catalyst · h) |
| Temperature (Max.) | 330° C. |
| Pressure | 1 atm (abs) |
| Catalyst | H-ZSM-5 (Si/Al 280) |

TABLE 2.2

Product Distribution (wt %)

| Gas | | Liquid | |
|---|---|---|---|
| $CH_4$ | 0.00% | C5s | 13.17% |
| $CO_2$ | 0.00% | C6s | 16.01% |
| $C_2H_4$ | 1.09% | C7s | 6.98% |
| $C_2H_6$ | 0.00% | C8s | 14.95% |
| $C_3H_6$ | 3.13% | C9s | 6.36% |
| $C_3H_8$ | 6.50% | C10s | 4.46% |
| CO | 0.33% | C11+ | 1.30% |
| C4s | 25.72% | Total | 63.23% |
| Total | 36.77% | | |

TABLE 2.3

Hydrocarbon Distribution in the Liquid (Gasoline) Fraction (wt %)

| Paraffins | Olefins | Isomeric Compounds | Naphthenes | Naphthene Olefinics | Aromatics |
|---|---|---|---|---|---|
| 7.869 | 4.661 | 15.215 | 15.037 | 1.472 | 49.349 |

Example 3

Acetone to Hydrocarbons (Si/Al 30)

Materials and Methods: Liquid acetone was vaporized and added to the reactor operated using the conditions shown in Table 3.1. The product exiting the reactor was separated into two fractions: liquid and gas. The total mass of each product was measured and the composition was determined by gas chromatography/mass spectroscopy (GC/MS).

Figure 44:
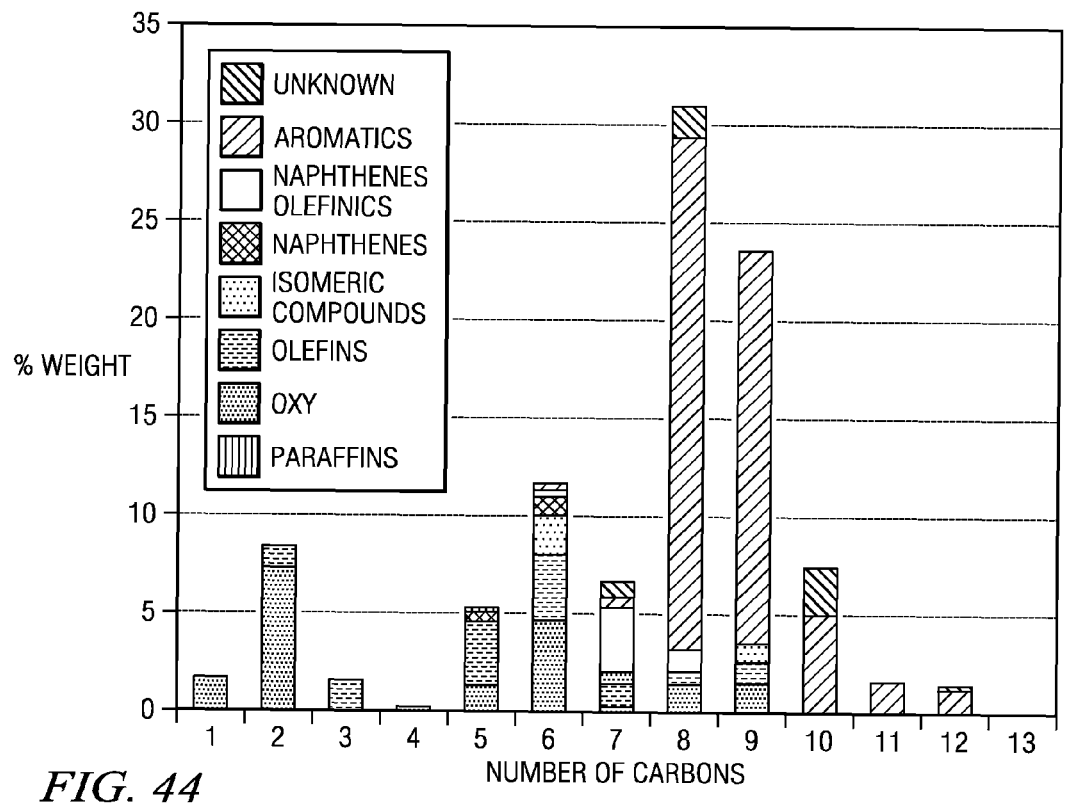
FIG. 44 illustrates the liquid-phase product distribution as a function of hydrocarbon type and number of carbons for acetone oligomerization over H-ZSM-5 zeolite (Si/Al ratio 30), according to one example embodiment.

Results: Table 3.2 shows the product distribution. Of the total product, the liquid fraction (gasoline) was 67.16% and the gases were 32.86%. Table 3.3 shows the classes of products in the liquid fraction. FIG. 44 illustrates the liquid-phase product distribution as a function of hydrocarbon type and number of carbons for acetone oligomerization over H-ZSM-5 zeolite (Si/Al ratio 30). Under these conditions, the reaction did not quite go to completion; however, other conditions have shown near-complete conversion is possible (see Example 5).

TABLE 3.1

Example 3 Reaction Conditions-
Acetone-to-Hydrocarbon Reactor

| | |
|---|---|
| Acetone Flow Rate | 10 mL liquid/h |
| Catalyst Mass | 6 g |
| Weight Hourly Space Velocity (WHSV) | 1.31 g reactant/(g catalyst · h) |
| Pressure | 1 atm (abs) |
| Temperature (Max.) | 330° C. |
| Catalyst | H-ZSM-5 (Si/Al 30) |

TABLE 3.2

Product Distribution (wt %)

| Gas | | Liquid | |
|---|---|---|---|
| $CH_4$ | 0.22% | C5s | 0.92% |
| $CO_2$ | 1.62% | Acetone | 8.06% |
| $C_2H_4$ | 2.76% | C6s | 8.58% |
| $C_2H_6$ | 0.04% | C7s | 6.52% |
| $C_3H_6$ | 1.19% | C8s | 18.13% |
| $C_3H_8$ | 1.40% | C9s | 14.01% |
| CO | 0.43% | C10s | 6.41% |
| C4s | 25.20% | C11+ | 4.53% |
| Total | 32.86% | Total | 67.16% |

TABLE 3.3

Hydrocarbon Distribution in the Liquid (Gasoline) Fraction (wt %)

| Paraffins | Oxygenates | Olefins | Isomeric compounds | Naphthenes | Naphthene Olefinics | Aromatics | Unknown |
|---|---|---|---|---|---|---|---|
| 0 | 9.351 | 9.428 | 2.971 | 1.88 | 4.769 | 54.912 | 5.033 |

Example 4

Acetone to Hydrocarbons (Si/Al 280)

Materials and Methods: Liquid acetone was vaporized and added to the reactor operated using the conditions shown in Table 4.1. The product exiting the reactor was separated into two fractions: liquid and gas. The total mass of each product was measured and the composition was determined by gas chromatography/mass spectroscopy (GC/MS).

Figure 45:
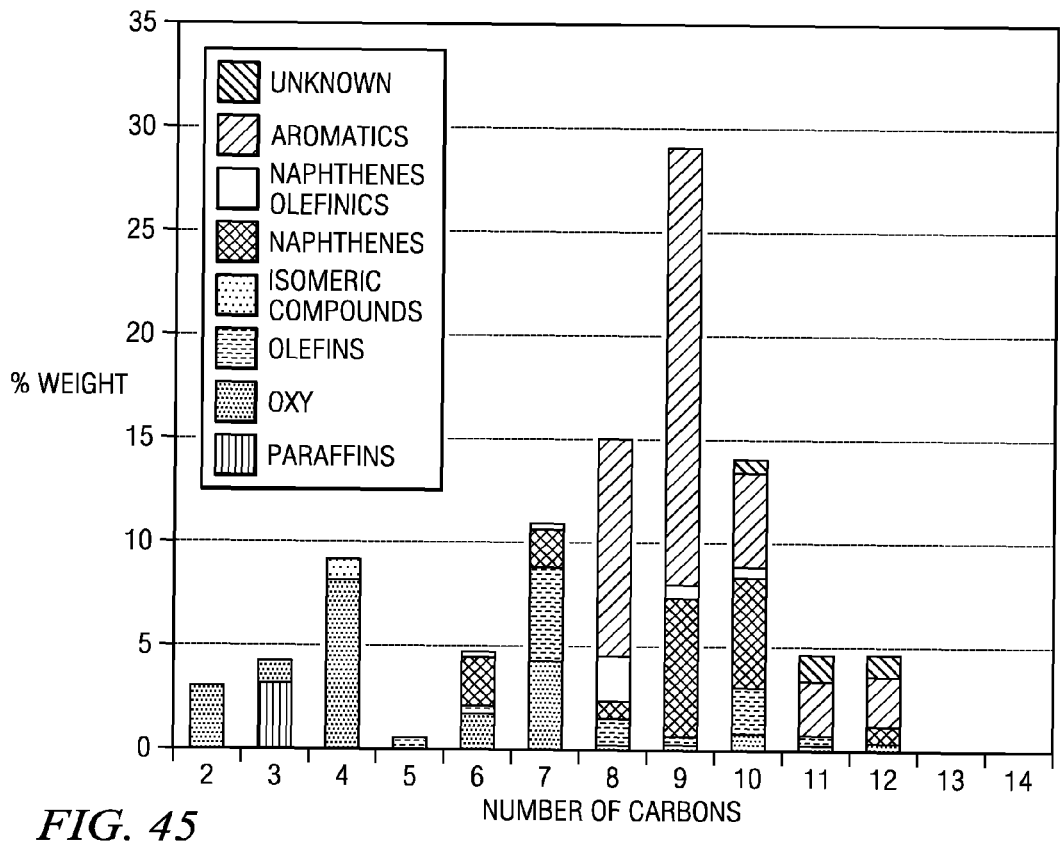
FIG. 45 illustrates the liquid-phase product distribution as a function of hydrocarbon type and number of carbons for acetone oligomerization over H-ZSM-5 zeolite (Si/Al ratio 280) at 330° C., according to one example embodiment.

Results: Table 4.2 shows the product distribution. Of the total product, the liquid fraction (gasoline) was 74.03% and the gases were 25.97%. Table 4.3 shows the classes of products in the liquid fraction. Tables 3.3 and 4.3 report identical conditions, except for the catalyst. The Si/Al 30 catalyst is more acidic than the Si/Al 280 catalyst. The Si/Al 280 catalyst produced more oxygenates and naphthenes, and less aromatics. FIG. 45 illustrates the liquid-phase product distribution as a function of hydrocarbon type and number of carbons for acetone oligomerization over H-ZSM-5 zeolite (Si/Al ratio 280). Under these conditions, the reaction did not quite go to completion; however, other conditions have shown near-complete conversion is possible (see Example 5).

TABLE 4.1

Example 4 Reaction Conditions-
Acetone-to-Hydrocarbon Reactor

| | |
|---|---|
| Acetone Flow Rate | 10 mL liquid/h |
| Catalyst Mass | 6 g |
| Weight Hourly Space Velocity (WHSV) | 1.31 g reactant/(g catalyst · h) |
| Pressure | 1 atm (abs) |
| Temperature (Max.) | 330° C. |
| Catalyst | H-ZSM-5 (Si/Al 280) |

TABLE 4.2

Product Distribution (wt %)

| Gas | | Liquid | |
|---|---|---|---|
| $CH_4$ | 0.15% | C5s | 0.40% |
| $CO_2$ | 0.74% | Acetone | 23.33% |
| $C_2H_4$ | 1.19% | C6s | 11.54% |
| $C_2H_6$ | 0.00% | C7s | 5.95% |
| $C_3H_6$ | 2.27% | C8s | 8.16% |
| $C_3H_8$ | 0.31% | C9s | 13.88% |
| CO | 0.05% | C10s | 6.85% |
| C4s | 21.26% | C11+ | 3.92% |
| Total | 25.97 | Total | 74.03% |

TABLE 4.3

Hydrocarbon Distribution in the Liquid (Gasoline) Fraction (wt %)

| Paraffins | Oxygenates | Olefins | Isomeric Compounds | Naphthenes | Naphthene Olefinics | Aromatics | Unknown |
|---|---|---|---|---|---|---|---|
| 0 | 15.894 | 9.374 | 1.01 | 17.865 | 3.862 | 41.26 | 2.942 |

Example 5

Acetone to Hydrocarbons (Si/Al 280)

Materials and Methods: Liquid acetone was vaporized and added to the reactor operated using the conditions shown in Table 5.1. The product exiting the reactor was separated into two fractions: liquid and gas. The total mass of each product was measured and the composition was determined by gas chromatography/mass spectroscopy (GC/MS).

Figure 46:
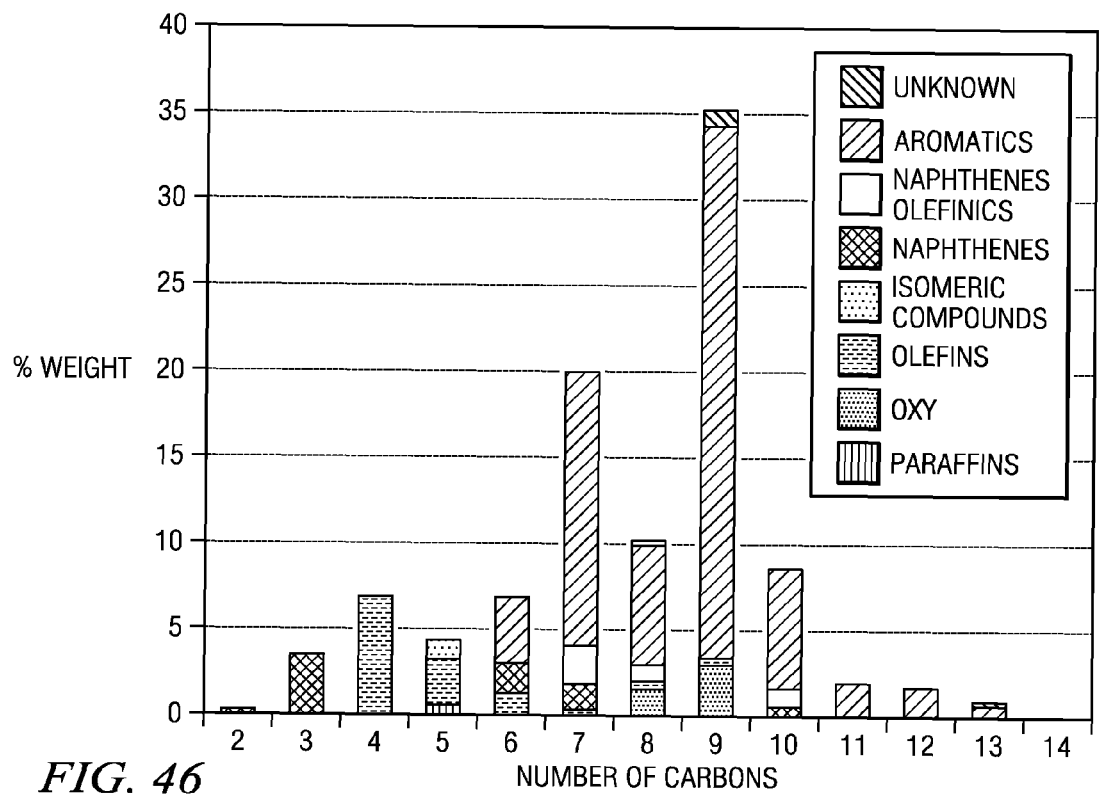
FIG. 46 illustrates the liquid-phase product distribution as a function of hydrocarbon type and number of carbons for acetone oligomerization over H-ZSM-5 zeolite (Si/Al ratio 280) at 400° C., according to one example embodiment.

Results: Table 5.2 shows the product distribution. Of the total product, the liquid fraction (gasoline) was 86.16% and the gases were 13.82%. Table 5.3 shows the classes of products in the liquid fraction. Tables 4.3 and 5.3 report identical conditions, except for temperature. The higher temperature reduces the oxygenates and naphthenes, and increases the aromatics. FIG. 46 illustrates the liquid-phase product distribution as a function of hydrocarbon type and number of carbons for acetone oligomerization over H-ZSM-5 zeolite (Si/Al ratio 280). In this example, the reaction went nearly to completion.

TABLE 5.1

Example 5 Reaction Conditions-
Acetone-to-Hydrocarbon Reactor

| | |
|---|---|
| Acetone Flow Rate | 10 mL liquid/h |
| Catalyst Mass | 6 g |
| Weight Hourly Space Velocity (WHSV) | 1.31 g reactant/(g catalyst · h) |
| Pressure | 1 atm (abs) |
| Temperature (Max.) | 400° C. |
| Catalyst | H-ZSM-5 (Si/Al 280) |

TABLE 5.2

Product Distribution (wt %)

| Gas | | Liquid | |
|---|---|---|---|
| $CH_4$ | 0.11% | C5s | 1.39% |
| $CO_2$ | 1.63% | Acetone | 0.72% |
| $C_2H_4$ | 1.49% | C6s | 8.94% |
| $C_2H_6$ | 0.00% | C7s | 13.92% |
| $C_3H_6$ | 1.63% | C8s | 30.54% |
| $C_3H_8$ | 1.00% | C9s | 17.18% |
| CO | 0.28% | C10s | 9.29% |
| C4s | 7.68% | C11+ | 4.18% |
| Total | 13.82 | Total | 86.16% |

TABLE 5.3

Hydrocarbon Distribution in the Liquid (Gasoline) Fraction (wt %)

| Paraffins | Oxygenates | Olefins | Isomeric Compounds | Naphthenes | Naphthene Olefinics | Aromatics | Unknown |
|---|---|---|---|---|---|---|---|
| 0.548 | 4.583 | 2.26 | 1.083 | 3.772 | 4.359 | 68.983 | 1.255 |

Example 6

Acetone and Hydrogen to Hydrocarbons (Si/Al 280)

Materials and Methods: Hydrogen and vaporized acetone were added to the reactor operated using the conditions shown in Table 6.1. The product exiting the reactor was separated into two fractions: liquid and gas. The total mass of each product was measured and the composition was determined by gas chromatography/mass spectroscopy (GC/MS).

Figure 47:
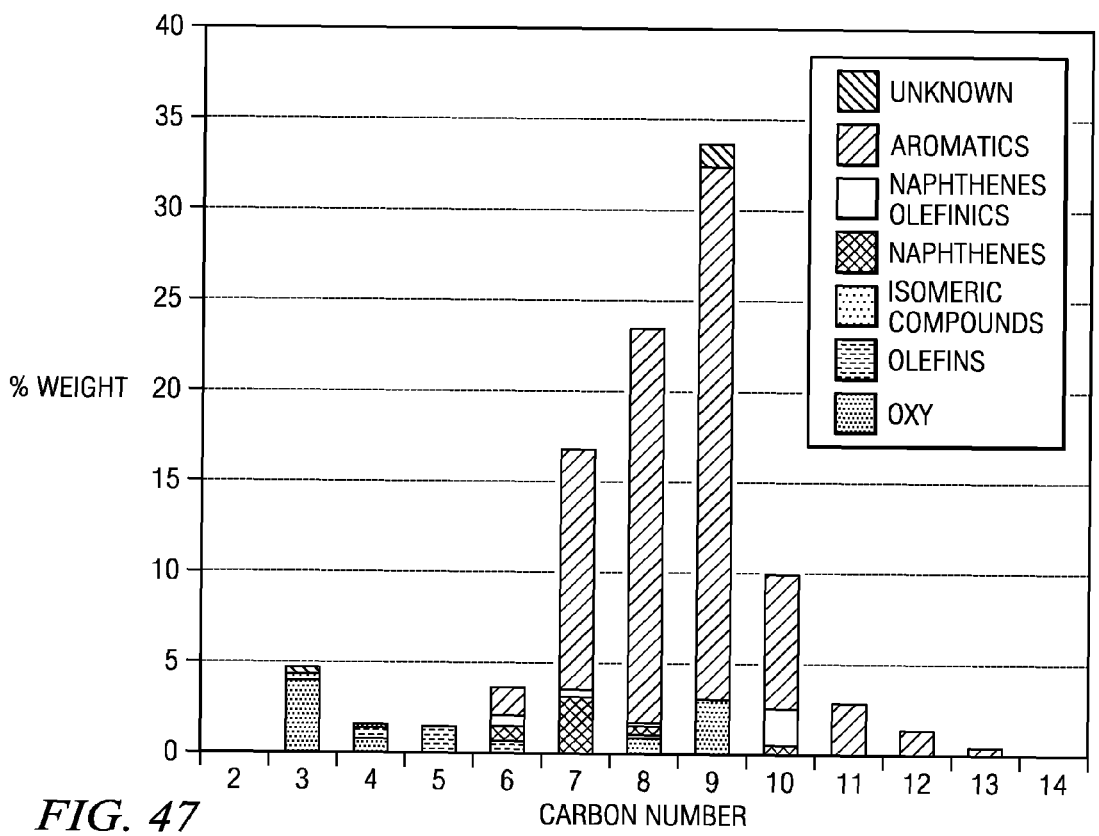
FIG. 47 illustrates the liquid-phase product distribution as a function of hydrocarbon type and number of carbons for acetone and hydrogen oligomerization over H-ZSM-5 zeolite (Si/Al ratio 280), according to one example embodiment.

Results: Table 6.2 shows the product distribution. Of the total product, the liquid fraction (gasoline) was 80.63% and the gases were 19.38%. The per-pass hydrogen conversion was 44.25%. Table 6.3 shows the classes of products in the liquid fraction. Tables 5.3 and 6.3 report identical conditions, except for the presence of hydrogen, which increases aromatics. FIG. 47 illustrates the liquid-phase product distribution as a function of hydrocarbon type and number of carbons for acetone and hydrogen oligomerization over H-ZSM-5 zeolite (Si/Al ratio 280). In this example, the reaction went nearly to completion.

TABLE 6.1

Example 6 Reaction Conditions-
Acetone-plus-Hydrogen-to-Hydrocarbon Reactor

| | |
|---|---|
| Acetone Flow Rate | 10 mL liquid/h |
| | 0.13 mol/h |
| Water Flow | 0 |
| Hydrogen | 53 mL/min 0.13 mol/h |
| Ratio $H_2$/Acetone | 1 molar ratio |
| Pressure | 1 atm (abs) |
| Temperature (Max.) | 400° C. |
| Catalyst | H-ZSM-5 (Si/Al 280) |

TABLE 6.2

Product Distribution (wt %)

| Gas | | Liquid | |
|---|---|---|---|
| $CH_4$ | 0.14% | C5s | 0.84% |
| $CO_2$ | 2.72% | Acetone | 4.05% |
| $C_2H_4$ | 2.31% | C6s | 11.54% |
| $C_2H_6$ | 0.00% | C7s | 15.81% |
| $C_3H_6$ | 2.56% | C8s | 18.71% |
| $C_3H_8$ | 1.00% | C9s | 11.39% |
| CO | 0.41% | C10s | 9.79% |
| C4s | 10.24% | C11+ | 8.50% |
| Total | 19.38% | Total | 80.63% |

TABLE 6.3

Hydrocarbon Distribution in the Liquid (Gasoline) Fraction (wt %)

| Paraffins | Oxygenates | Olefins | Isomeric Compounds | Naphthenes | Naphthene Olefinics | Aromatics | Unknown |
|---|---|---|---|---|---|---|---|
| 0 | 8.688 | 3.103 | 0.295 | 4.853 | 3.209 | 77.83 | 1.582 |

Example 7

Acetic Acid To Hydrocarbons (Si/Al 280)

Materials and Methods: Liquid acetic acid was vaporized and added to the reactor operated using the conditions shown in Table 7.1. The product exiting the reactor was separated into two fractions: liquid and gas. The total mass of each product was measured and the composition was determined by gas chromatography/mass spectroscopy (GC/MS).

Figure 48:
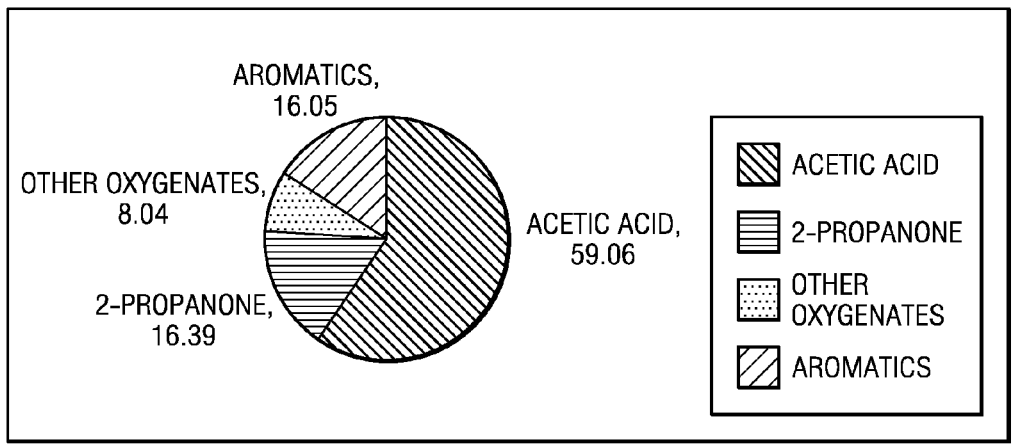
FIG. 48 illustrates the liquid-phase product distribution for acetic acid oligomerization over H-ZSM-5 zeolite (Si/Al ratio 280), according to one example embodiment.

Results: Table 7.2 shows the product distribution. Of the total product, the liquid fraction was 49.77% and the gases were 51.76%. FIG. 48 illustrates the liquid-phase product distribution as a function of hydrocarbon type and number of carbons for acetic acid oligomerization over H-ZSM-5 zeolite (Si/Al ratio 280).

TABLE 7.1

Example 7 Reaction Conditions-
Acetic-Acid-to-Hydrocarbon Reactor

| | |
|---|---|
| Acetic Acid Flow Rate | 10 mL liquid/h |
| Catalyst Mass | 6 g |
| Weight Hourly Space Velocity (WHSV) | 1.31 g reactant/(g catalyst · h) |
| Pressure | 1 atm (abs) |
| Temperature (Max.) | 400° C. |
| Catalyst | H-ZSM-5 (Si/Al 280) |

TABLE 7.2

Product Distribution (wt %)

| Gas | | Liquid | |
|---|---|---|---|
| $CH_4$ | 0.13% | Acetic acid | 29.53% |
| $CO_2$ | 33.99% | 2-Propanone | 8.195% |
| $C_2H_4$ | 0.23% | Other Oxygenates | 4.02% |
| $C_2H_6$ | 0.00% | Aromatics | 8.025% |
| $O_2$ | 0.00% | Total | 49.77% |
| $N_2$ | 0.00% | | |
| $H_2O$ | 0.00% | | |
| $C_3H_6$ | 0.66% | | |
| $C_3H_8$ | 0.00% | | |
| CO | 0.66% | | |
| C4s | 16.09% | | |
| Total | 51.76% | | |

Example 8

Acetic Acid and Hydrogen to Hydrocarbons (Si/Al 280)

Materials and Methods: Hydrogen and vaporized acetic acid were added to the reactor operated using the conditions shown in Table 8.1. The product exiting the reactor was separated into two fractions: liquid and gas. The total mass of each product was measured and the composition was determined by gas chromatography/mass spectroscopy (GC/MS).

Figure 49:
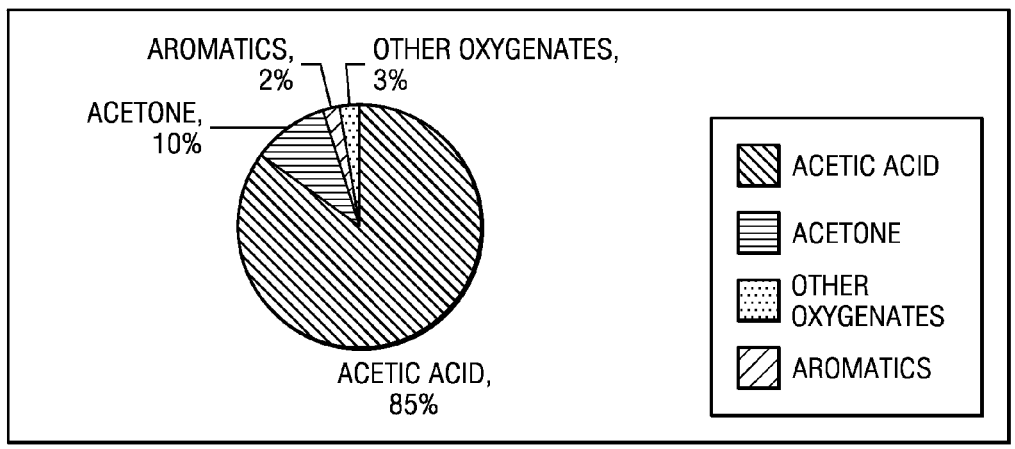
FIG. 49 illustrates the liquid-phase distribution for acetic acid and hydrogen oligomerization over H-ZSM-5 zeolite (Si/Al ratio 280), according to one example embodiment.

Results: Table 8.2 shows the product distribution. Of the total product, the liquid fraction was 47.59% and the gases were 52.34%. The hydrogen conversion was 19.17%. FIG. 49 illustrates the liquid-phase distribution for acetic acid and hydrogen oligomerization over H-ZSM-5 zeolite (Si/Al ratio 280). In this example, a substantial portion of the acetic acid was unreacted, so a longer residence time is needed.

TABLE 8.1

Example 8 Reaction Conditions-
Acetic-Acid-plus-Hydrogen-to-Hydrocarbon Reactor

| | |
|---|---|
| Acetic Acid Flow Rate | 10 mL liquid/h |
| Hydrogen Flow Rate | 36 cm$^3$/min |
| Ratio Acid/H$_2$ | 2 molar ratio |
| Catalyst Mass | 6 g |
| Temperature (Max.) | 410° C. |
| Pressure | 1 atm (abs) |
| Catalyst | H-ZSM-5 (Si/Al 280) |

TABLE 8.2

Product distribution (wt %)

| Gas | | Liquid | |
|---|---|---|---|
| CH$_4$ | 0.24% | Acetic Acid | 40.48% |
| CO$_2$ | 30.52% | 2-Propanone | 4.90% |
| C$_2$H$_4$ | 0.00% | Other Oxygenates | 0.90% |
| C$_2$H$_6$ | 0.00% | Aromatics | 1.31% |
| C$_3$H$_6$ | 3.17% | Total | 47.59 |
| C$_3$H$_8$ | 0.00% | | |
| CO | 0.37% | | |
| Isobutane | 0.00% | | |
| Butane | 18.04% | | |
| Isobutylene | 0.00% | | |
| 1-Butene | 0.00% | | |
| Total | 52.34 | | |

Example 9

Ammonium Acetate to Hydrocarbons (Si/Al 280)

Materials and Methods: An aqueous solution of 20% ammonium was vaporized and added to the reactor operated using the conditions shown in Table 9.1. The product exiting the reactor was separated into two fractions: liquid and gas. The total mass of each product was measured and the composition was determined by gas chromatography/mass spectroscopy (GC/MS).

Figure 50:
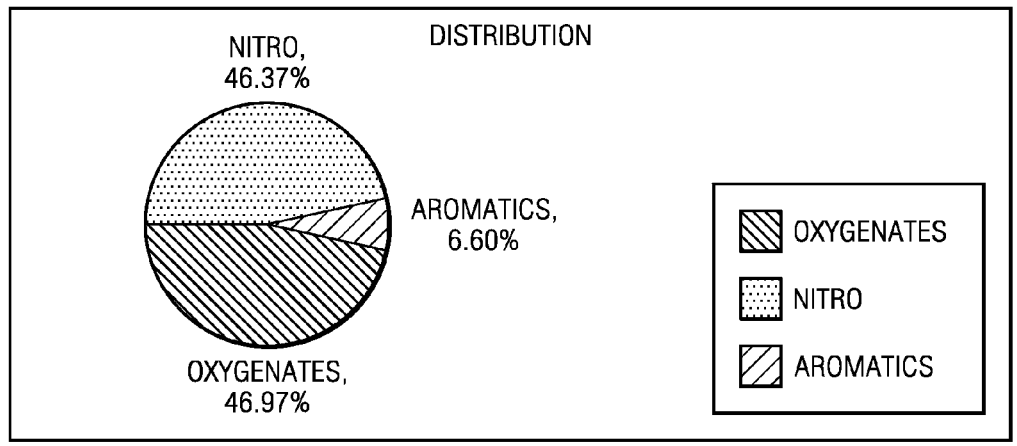
FIG. 50 illustrates the liquid-phase distribution for ammonium acetate oligomerization over H-ZSM-5 zeolite (Si/Al ratio 280), according to one example embodiment.

Results: Table 9.2 shows the dominant liquid-phase products. FIG. 50 illustrates the liquid-phase distribution as for ammonium acetate oligomerization over H-ZSM-5 zeolite (Si/Al ratio 280). The aromatics are molecules with 8 and 12 carbons.

TABLE 9.1

Example 9 Reaction Conditions-
Ammonium-Acetate-to-Hydrocarbon Reactor

| | |
|---|---|
| Ammonium Acetate Solution | 50 mL/h |
| Ammonium Acetate Concentration | 20% (w/w) |
| Ammonium Acetate Addition Rate | 10 g/h |
| Catalyst Mass | 6 g |
| Weight Hourly Space Velocity (WHSV) | 1.66 g reactant/(g catalyst · h) |
| Temperature (Max.) | 400° C. |
| Pressure | 1 atm (abs) |
| Catalyst | H-ZSM-5 (Si/Al 280) |

TABLE 9.2

Dominant Compounds in Liquid Phase

| | |
|---|---|
| Acetonitrile | 42.70 |
| Acetic acid | 21.29 |
| Acetone | 16.80 |
| Total | 80.79 |

While preferred embodiments of the invention have been shown and described, modifications thereof can be made by one skilled in the art without departing from the spirit and teachings of the invention. The embodiments described herein are exemplary only, and are not intended to be limiting. Many variations and modifications of the invention disclosed herein are possible and are within the scope of the invention. Where numerical ranges or limitations are expressly stated, such express ranges or limitations should be understood to include iterative ranges or limitations of like magnitude falling within the expressly stated ranges or limitations (e.g., from about 1 to about 10 includes, 2, 3, 4, etc.; greater than 0.10 includes 0.11, 0.12, 0.13, and so forth). Use of the term "optionally" with respect to any element of a claim is intended to mean that the subject element is required, or alternatively, is not required. Both alternatives are intended to be within the scope of the claim. Use of broader terms such as comprises, includes, having, etc. should be understood to provide support for narrower terms such as consisting of, consisting essentially of, comprised substantially of, and the like.

Modifications, additions, or omissions may be made to the systems and apparatuses described herein without departing from the scope of the invention. The components of the systems and apparatuses may be integrated or separated. Moreover, the operations of the systems and apparatuses may be performed by more, fewer, or other components. The methods may include more, fewer, or other steps. Additionally, steps may be performed in any suitable order.

Accordingly, the scope of protection is not limited by the description set out above but is only limited by the claims which follow, that scope including all equivalents of the subject matter of the claims. Each and every claim is incorporated into the specification as an embodiment of the present invention. Thus, the claims are a further description and are an addition to the preferred embodiments of the present invention. The disclosures of all patents, patent applications, and publications cited herein are hereby incorporated by reference, to the extent they provide exemplary, procedural or other details supplementary to those set forth herein.

We claim:

1. A method of producing hydrocarbons from biomass, the method comprising:
converting at least a portion of the biomass into a carboxylic acid, a ketone, or an ammonium carboxylate salt; reacting at least one of a portion of the carboxylic acid, a portion of the ketone, or a portion of the ammonium carboxylate salt in an oligomerization reactor as at least part of a process that produces an oligomerization product; and separating hydrocarbons from the oligomerization product.

2. The method of claim 1, further comprising: converting another portion of the carboxylic acid, another portion of the ketone, or another portion of the ammonium carboxylate salt to alcohol; and providing at least a portion of the alcohol to the oligomerization reactor for the process that produces the oligomerization product.

3. The method of claim 2, wherein converting the another portion of the carboxylic acid into alcohol comprises: reacting the another portion of the carboxylic acid with an olefin to produce an ester; and hydrogenolyzing the ester to produce the alcohol.

4. The method of claim 2, wherein reacting at least one of the portion of the carboxylic acid, the portion of the ketone, or the portion of the ammonium carboxylate salt in the oligomerization reactor as at least part of the process that produces the oligomerization product and converting the another portion of the carboxylic acid, the another portion of the ketone, or the another portion of the ammonium carboxylate salt to alcohol are carried out in the oligomerization reactor.

5. The method of claim 4, wherein reacting at least one of the portion of the carboxylic acid, the portion of the ketone, or the portion of the ammonium carboxylate salt in the oligomerization reactor as at least part of the process that produces the oligomerization product and converting the another portion of the carboxylic acid, the another portion of the ketone, or the another portion of the ammonium carboxylate salt to alcohol are carried out with one catalyst.

6. The method of claim 2, further comprising: separating a recycle stream from the oligomerization product; processing the recycle stream in a reformer to produce hydrogen; and providing a least a portion of the produced hydrogen for the process of converting the another portion of the carboxylic acid, the another portion of the ketone, or the another portion of the ammonium carboxylate salt to alcohol.

7. The method of claim 6, wherein at least a portion of the biomass is converted to the ammonium carboxylate salt, the method further comprising: separating ammonia from the recycle stream prior to processing the recycle stream in a reformer to produce hydrogen.

8. The method of claim 6, further comprising: separating olefins from the recycle stream prior to processing the recycle stream in a reformer to produce hydrogen; and providing the olefins to the oligomerization reactor for the process that produces the oligomerization product.

9. The method of claim 8, wherein at least a portion of the biomass is converted to an ammonium carboxylate salt, the method further comprising: separating ammonia from the recycle stream prior to processing the recycle stream in a reformer to produce hydrogen.

10. The method of claim 2, further comprising: separating a recycle stream from the oligomerization product; separating olefins from the recycle stream; and providing the olefins to the oligomerization reactor for the process that produces the oligomerization product.

11. The method of claim 1, wherein at least a portion of the biomass is converted into a carboxylic acid.

12. The method of claim 1, wherein converting at least a portion of the biomass into a carboxylic acid comprises: fermenting the biomass to produce a carboxylate salt; and converting the carboxylate salt to carboxylic acid using an acid recovery process.

13. The method of claim 1, wherein at least a portion of the biomass is converted into a ketone.

14. The method of claim 13, wherein converting at least a portion of the biomass into a ketone comprises: fermenting the biomass to produce a carboxylate salt; and thermally converting the carboxylate salt into the ketone.

15. The method of claim 13, wherein converting at least a portion of the biomass into a ketone comprises: fermenting the biomass to produce a carboxylate salt; converting the carboxylate salt to carboxylic acid using an acid recovery process, and catalytically converting carboxylic acid into ketone.

16. The method of claim 13, further comprising converting another portion of the ketone into alcohol by hydrogenating the another portion of the ketone.

17. The method of claim 1, wherein converting at least a portion of the biomass into a ketone comprises: fermenting the biomass to produce a carboxylate salt; and producing hot ketone vapors and carbonate in a ketone reactor operated with a sweep gas.

18. The method of claim 17 wherein the sweep gas is reactive, condensable or both.

19. The method of claim 18 wherein the sweep gas comprises hydrogen or steam.

20. The method of claim 18 wherein the sweep gas comprises steam.

21. The method of claim 1, wherein at least a portion of the biomass is converted into the ammonium carboxylate salt.

22. The method of claim 21, wherein the conversion to ammonium carboxylate salt further comprises converting another portion of the ammonium carboxylate salt to alcohol; and providing the alcohol to the oligomerization reactor for the process that produces the oligomerization product, wherein converting the another portion of the ammonium carboxylate salt into alcohol comprises: converting the another portion of the ammonium carboxylate salt into a second carboxylic acid; reacting the second carboxylic acid with an olefin to produce an ester; and hydrogenolyzing the ester to produce the alcohol.

23. The method of claim 21, further comprising: separating ammonia from the ammonium carboxylate salt prior to reacting the portion of the ammonium carboxylate salt in the oligomerization reactor as at least part of the process that produces the oligomerization product.

24. The method of claim 1, wherein converting at least a portion of the biomass into a carboxylic acid, a ketone, or an ammonium carboxylate salt comprises a fermentation process in a fermenter, the method further comprising: separating a gaseous recycle stream from the oligomerization product; and providing at least a portion of the gaseous recycle stream to the fermenter.

25. The method of claim 24, further comprising: converting another portion of the carboxylic acid, another portion of the ketone, or another portion of the ammonium carboxylate salt to alcohol; and providing the alcohol to the oligomerization reactor.

26. The method of claim 25, wherein at least a portion of the biomass is converted into a carboxylic acid.

27. The method of claim 25, wherein at least a portion of the biomass is converted into a ketone.

28. The method of claim 25, wherein at least a portion of the biomass is converted into an ammonium carboxylate salt.

29. The method of claim 28, further comprising: separating ammonia from the gaseous recycle stream prior to providing the at least a portion of the gaseous recycle stream to the fermenter.

30. The method of claim 25, wherein reacting at least one of the portion of the carboxylic acid, the portion of the ketone, or the portion of the ammonium carboxylate salt in the oligomerization reactor as at least part of the process that produces the oligomerization product and converting the another portion of the carboxylic acid, the another portion of the ketone, or the another portion of the ammonium carboxylate salt to alcohol are carried out in the oligomerization reactor.

31. The method of claim 30, wherein reacting at least one of the portion of the carboxylic acid, the portion of the ketone, or the portion of the ammonium carboxylate salt in the oligomerization reactor as at least part of the process that produces the oligomerization product and converting the another portion of the carboxylic acid, the another portion of the ketone, or the another portion of the ammonium carboxylate salt to alcohol are carried out with one catalyst.

32. The method of claim 25, further comprising: separating fermenter gases exiting the fermenter; processing the fermenter gases in a reformer to produce hydrogen; and providing a least a portion of the produced hydrogen for the process of converting the another portion of the carboxylic acid, the another portion of the ketone, or the another portion of the ammonium carboxylate salt to alcohol.

\* \* \* \* \*